United States Patent
Rothberg et al.

(10) Patent No.: US 10,266,401 B2
(45) Date of Patent: Apr. 23, 2019

(54) COMPLEMENTARY METAL OXIDE SEMICONDUCTOR (CMOS) ULTRASONIC TRANSDUCERS AND METHODS FOR FORMING THE SAME

(71) Applicant: Butterfly Network, Inc., Guilford, CT (US)

(72) Inventors: Jonathan M. Rothberg, Guilford, CT (US); Keith G. Fife, Palo Alto, CA (US); Tyler S. Ralston, Clinton, CT (US); Gregory L. Charvat, Guilford, CT (US); Nevada J. Sanchez, Guilford, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 15/910,776

(22) Filed: Mar. 2, 2018

(65) Prior Publication Data
US 2018/0186628 A1    Jul. 5, 2018

Related U.S. Application Data

(63) Continuation of application No. 15/626,801, filed on Jun. 19, 2017, now Pat. No. 9,944,514, which is a
(Continued)

(51) Int. Cl.
*H01L 29/84*    (2006.01)
*B81C 1/00*    (2006.01)
(Continued)

(52) U.S. Cl.
CPC ............ *B81C 1/00301* (2013.01); *B06B 1/02* (2013.01); *B06B 1/0292* (2013.01); *B81B 7/007* (2013.01);
(Continued)

(58) Field of Classification Search
CPC ... H01L 29/84; B06B 1/0292; B81C 1/00158; G01N 29/2406; H04R 19/005
(Continued)

(56) References Cited

U.S. PATENT DOCUMENTS

| | | |
|---|---|---|
| 5,286,671 A | 2/1994 | Kurtz et al. |
| 6,430,109 B1 | 8/2002 | Khuri-Yakub et al. |

(Continued)

FOREIGN PATENT DOCUMENTS

| | | |
|---|---|---|
| CN | 101640834 A | 2/2010 |
| EP | 2 441 530 A2 | 4/2012 |

(Continued)

OTHER PUBLICATIONS

U.S. Appl. No. 15/581,511, filed Apr. 28, 2017, Rothberg et al.
(Continued)

*Primary Examiner* — Stephen W Smoot
(74) *Attorney, Agent, or Firm* — Wolf, Greenfield & Sacks, P.C.

(57) ABSTRACT

Complementary metal oxide semiconductor (CMOS) ultrasonic transducers (CUTs) and methods for forming CUTs are described. The CUTs may include monolithically integrated ultrasonic transducers and integrated circuits for operating in connection with the transducers. The CUTs may be used in ultrasound devices such as ultrasound imaging devices and/or high intensity focused ultrasound (HIFU) devices.

17 Claims, 35 Drawing Sheets

Related U.S. Application Data continuation of application No. 15/291,697, filed on Oct. 12, 2016, now Pat. No. 9,738,514, which is a continuation of application No. 15/042,931, filed on Feb. 12, 2016, now Pat. No. 9,499,395, which is a continuation of application No. 14/711,145, filed on May 13, 2015, now Pat. No. 9,290,375, which is a continuation of application No. 14/561,384, filed on Dec. 5, 2014, now Pat. No. 9,061,318, which is a continuation of application No. 14/208,351, filed on Mar. 13, 2014, now Pat. No. 9,242,275.

(60) Provisional application No. 61/794,744, filed on Mar. 15, 2013.

(51) Int. Cl.
*B06B 1/02* (2006.01)
*G01N 29/24* (2006.01)
*H04R 19/00* (2006.01)
*B81B 7/00* (2006.01)

(52) U.S. Cl.
CPC ...... *B81C 1/00158* (2013.01); *B81C 1/00246* (2013.01); *G01N 29/2406* (2013.01); *H01L 29/84* (2013.01); *H04R 19/005* (2013.01); *B81C 1/00134* (2013.01); *B81C 2201/0195* (2013.01); *B81C 2203/0735* (2013.01); *B81C 2203/0771* (2013.01)

(58) Field of Classification Search
USPC ............................................. 257/416, 419
See application file for complete search history.

(56) References Cited

U.S. PATENT DOCUMENTS

| | | |
|---|---|---|
| 6,443,901 B1 | 9/2002 | Fraser |
| 6,645,145 B1 | 11/2003 | Dreschel et al. |
| 6,659,954 B2 | 12/2003 | Robinson |
| 6,694,817 B2 | 2/2004 | Degertekin et al. |
| 6,779,387 B2 | 8/2004 | Degertekin |
| 6,795,374 B2 | 9/2004 | Barnes et al. |
| 6,831,394 B2 | 12/2004 | Baumgartner et al. |
| 6,865,140 B2 | 3/2005 | Thomenius et al. |
| 6,958,255 B2 | 10/2005 | Khuri-Yakub et al. |
| 7,030,536 B2 | 4/2006 | Smith et al. |
| 7,037,746 B1 | 5/2006 | Smith et al. |
| 7,052,464 B2 | 5/2006 | Wodnicki |
| 7,104,129 B2 | 9/2006 | Nasiri et al. |
| 7,125,383 B2 | 10/2006 | Hoctor et al. |
| 7,247,246 B2 | 7/2007 | Nasiri et al. |
| 7,250,353 B2 | 7/2007 | Nasiri et al. |
| 7,257,051 B2 | 8/2007 | Thomenius et al. |
| 7,285,897 B2 | 10/2007 | Fisher et al. |
| 7,312,440 B2 | 12/2007 | Degertekin et al. |
| 7,313,053 B2 | 12/2007 | Wodnicki |
| 7,375,420 B2 | 5/2008 | Fisher et al. |
| 7,441,321 B2 | 10/2008 | Baumgartner et al. |
| 7,441,447 B2 | 10/2008 | Degertekin et al. |
| 7,442,570 B2 | 10/2008 | Nasiri et al. |
| 7,451,651 B2 | 11/2008 | Woychik et al. |
| 7,518,251 B2 | 4/2009 | Fisher et al. |
| 7,530,952 B2 | 5/2009 | Huang et al. |
| 7,545,012 B2 | 6/2009 | Smith et al. |
| 7,557,342 B2 | 7/2009 | Fedorov et al. |
| 7,564,172 B1 | 7/2009 | Huang |
| 7,612,483 B2 | 11/2009 | Degertekin |
| 7,612,635 B2 | 11/2009 | Huang |
| 7,615,834 B2 | 11/2009 | Khuri-Yakub et al. |
| 7,622,848 B2 | 11/2009 | Lee et al. |
| 7,637,149 B2 | 12/2009 | Degertekin et al. |
| 7,646,133 B2 | 1/2010 | Degertekin |
| 7,687,976 B2 | 3/2010 | Haider et al. |
| 7,745,248 B2 | 6/2010 | Park et al. |
| 7,759,839 B2 | 7/2010 | Huang |
| 7,764,003 B2 | 7/2010 | Huang |
| 7,779,696 B2 | 8/2010 | Huang |
| 7,846,102 B2 | 12/2010 | Kupnik et al. |
| 7,878,977 B2 | 2/2011 | Mo et al. |
| 7,880,565 B2 | 2/2011 | Huang |
| 7,888,709 B2 | 2/2011 | Lemmerhirt et al. |
| 7,892,176 B2 | 2/2011 | Wodnicki et al. |
| 7,956,510 B2 | 6/2011 | Huang |
| 8,004,373 B2 | 8/2011 | Huang |
| 8,008,105 B2 | 8/2011 | Huang |
| 8,008,835 B2 | 8/2011 | Degertekin |
| 8,018,301 B2 | 9/2011 | Huang |
| 8,076,821 B2 | 12/2011 | Degertekin |
| 8,105,941 B2 | 1/2012 | Huang |
| 8,120,229 B2 | 2/2012 | Huang |
| 8,203,912 B2 | 6/2012 | Roest et al. |
| 8,222,065 B1 | 7/2012 | Smeys et al. |
| 8,241,931 B1 | 8/2012 | Antoine et al. |
| 8,247,945 B2 | 8/2012 | Huang |
| 8,277,380 B2 | 10/2012 | Daft et al. |
| 8,309,428 B2 | 11/2012 | Lemmerhirt et al. |
| 8,315,125 B2 | 11/2012 | Lemmerhirt et al. |
| 8,327,521 B2 | 12/2012 | Dirksen et al. |
| 8,334,133 B2 | 12/2012 | Fedorov et al. |
| 8,345,508 B2 | 1/2013 | Wodnicki et al. |
| 8,345,513 B2 | 1/2013 | Huang |
| 8,363,514 B2 | 1/2013 | Huang |
| 8,372,011 B2 | 2/2013 | Degertekin |
| 8,398,554 B2 | 3/2013 | Degertekin |
| 8,399,278 B2 | 3/2013 | Lemmerhirt et al. |
| 8,402,831 B2 | 3/2013 | Kupnik et al. |
| 8,429,808 B2 | 4/2013 | Huang |
| 8,451,693 B2 | 5/2013 | Nikoozadeh et al. |
| 8,483,014 B2 | 7/2013 | Huang |
| 8,526,271 B2 | 9/2013 | Huang |
| 8,559,274 B2 | 10/2013 | Huang |
| 8,563,345 B2 | 10/2013 | Adler et al. |
| 8,564,076 B1 | 10/2013 | Huang et al. |
| 8,587,078 B2 | 11/2013 | Huang et al. |
| 8,647,279 B2 | 2/2014 | Daft et al. |
| 8,658,453 B2 | 2/2014 | Lemmerhirt et al. |
| 8,665,672 B2 | 3/2014 | Soeda et al. |
| 8,957,564 B1 | 2/2015 | Hiroe et al. |
| 9,061,318 B2 | 6/2015 | Rothberg et al. |
| 9,067,779 B1 | 6/2015 | Rothberg et al. |
| 9,242,275 B2 | 1/2016 | Rothberg et al. |
| 9,290,375 B2 | 3/2016 | Rothberg et al. |
| 9,394,162 B2 | 7/2016 | Rothberg et al. |
| 9,499,392 B2 | 11/2016 | Rothberg et al. |
| 9,499,395 B2 | 11/2016 | Rothberg et al. |
| 9,505,030 B2 | 11/2016 | Rothberg et al. |
| 9,533,873 B2 | 1/2017 | Rothberg et al. |
| 9,718,098 B2 | 8/2017 | Rothberg et al. |
| 9,738,514 B2 | 8/2017 | Rothberg et al. |
| 9,895,718 B2 | 2/2018 | Rothberg et al. |
| 9,899,371 B2 | 2/2018 | Rothberg et al. |
| 9,910,017 B2 | 3/2018 | Rothberg et al. |
| 9,910,018 B2 | 3/2018 | Rothberg et al. |
| 9,944,514 B2 | 4/2018 | Rothberg et al. |
| 2005/0075572 A1 | 4/2005 | Mills et al. |
| 2005/0121734 A1 | 6/2005 | Degertekin et al. |
| 2005/0177045 A1 | 8/2005 | Degertekin et al. |
| 2005/0203397 A1 | 9/2005 | Degertekin |
| 2005/0248232 A1 | 11/2005 | Itaya et al. |
| 2006/0116585 A1 | 6/2006 | Nguyen et al. |
| 2006/0179640 A1 | 8/2006 | Machida et al. |
| 2006/0230605 A1 | 10/2006 | Schlote-Holubek et al. |
| 2006/0238067 A1 | 10/2006 | Dausch |
| 2007/0167811 A1 | 7/2007 | Lemmerhirt et al. |
| 2007/0167812 A1 | 7/2007 | Lemmerhirt et al. |
| 2007/0180916 A1 | 8/2007 | Tian et al. |
| 2007/0190680 A1 | 8/2007 | Fukuda et al. |
| 2007/0215964 A1 | 9/2007 | Khuri-Yakub et al. |
| 2007/0262436 A1 | 11/2007 | Kweon et al. |
| 2008/0138922 A1 | 6/2008 | Wan |
| 2008/0194053 A1 | 8/2008 | Huang |
| 2008/0290756 A1 | 11/2008 | Huang |

(56) References Cited

U.S. PATENT DOCUMENTS

| | | | |
|---|---|---|---|
| 2008/0296708 | A1 | 12/2008 | Wodnicki et al. |
| 2008/0308920 | A1 | 12/2008 | Wan |
| 2009/0122651 | A1 | 5/2009 | Kupnik et al. |
| 2009/0134497 | A1 | 5/2009 | Barth et al. |
| 2009/0148967 | A1 | 6/2009 | Wodnicki et al. |
| 2009/0176375 | A1 | 7/2009 | Benson et al. |
| 2009/0250729 | A1 | 10/2009 | Lemmerhirt et al. |
| 2010/0027830 | A1 | 2/2010 | Hsu et al. |
| 2010/0171153 | A1 | 7/2010 | Yang |
| 2010/0225200 | A1 | 9/2010 | Kupnik et al. |
| 2010/0254222 | A1 | 10/2010 | Huang |
| 2011/0055447 | A1 | 3/2011 | Costa |
| 2011/0084570 | A1 | 4/2011 | Soeda et al. |
| 2011/0115333 | A1 | 5/2011 | Ezaki |
| 2011/0140224 | A1 | 6/2011 | Kropelnicki et al. |
| 2011/0272693 | A1 | 11/2011 | Kobayashi et al. |
| 2012/0074509 | A1 | 3/2012 | Berg et al. |
| 2012/0091543 | A1 | 4/2012 | Torashima et al. |
| 2012/0129301 | A1 | 5/2012 | Or-Bach et al. |
| 2012/0187508 | A1 | 7/2012 | Adler et al. |
| 2012/0248554 | A1 | 10/2012 | Klein et al. |
| 2013/0087867 | A1 | 4/2013 | Ho et al. |
| 2013/0096433 | A1 | 4/2013 | Lemmerhirt et al. |
| 2013/0116561 | A1 | 5/2013 | Rothberg et al. |
| 2013/0161702 | A1 | 6/2013 | Chen |
| 2013/0169110 | A1 | 7/2013 | Jeong et al. |
| 2014/0057382 | A1 | 2/2014 | Supino et al. |
| 2014/0217478 | A1 | 8/2014 | Rothberg et al. |
| 2014/0219062 | A1 | 8/2014 | Rothberg et al. |
| 2014/0264660 | A1 | 9/2014 | Rothberg et al. |
| 2014/0355381 | A1 | 12/2014 | Lal et al. |
| 2015/0084053 | A1 | 3/2015 | Rothberg et al. |
| 2015/0251896 | A1 | 9/2015 | Rothberg et al. |
| 2015/0298170 | A1 | 10/2015 | Rothberg et al. |
| 2016/0009544 | A1 | 1/2016 | Rothberg et al. |
| 2016/0009549 | A1 | 1/2016 | Rothberg et al. |
| 2016/0207760 | A1 | 7/2016 | Rothberg et al. |
| 2016/0264400 | A1 | 9/2016 | Rothberg et al. |
| 2016/0280538 | A1 | 9/2016 | Rothberg et al. |
| 2016/0290969 | A1 | 10/2016 | Rothberg et al. |
| 2016/0290970 | A1 | 10/2016 | Rothberg et al. |
| 2017/0029271 | A1 | 2/2017 | Rothberg et al. |
| 2017/0056926 | A1 | 3/2017 | Rothberg et al. |
| 2017/0225196 | A1 | 8/2017 | Rothberg et al. |
| 2017/0283254 | A1 | 10/2017 | Rothberg et al. |
| 2017/0315099 | A1 | 11/2017 | Rothberg et al. |
| 2018/0003678 | A1 | 1/2018 | Rothberg et al. |
| 2018/0130795 | A1 | 5/2018 | Rothberg et al. |
| 2018/0133756 | A1 | 5/2018 | Rothberg et al. |

FOREIGN PATENT DOCUMENTS

| | | |
|---|---|---|
| GB | 2 467 776 A | 8/2010 |
| JP | 2005-103294 A | 4/2005 |
| JP | 2006-122659 A | 5/2006 |
| JP | 2006-211185 A2 | 8/2006 |
| JP | 2007-215177 A2 | 8/2007 |
| JP | 2010-272956 A | 12/2010 |
| JP | 2011-522444 T2 | 7/2011 |
| JP | 2012-085239 A2 | 4/2012 |
| JP | 2012-519958 T2 | 8/2012 |
| KR | 10-2013-0134724 A | 12/2013 |
| WO | WO 2009/073562 A1 | 6/2009 |
| WO | WO 2009/107940 A2 | 9/2009 |
| WO | WO 2012/017978 A2 | 2/2012 |
| WO | WO 2014/151525 A2 | 9/2014 |

OTHER PUBLICATIONS

U.S. Appl. No. 15/868,989, filed Jan. 11, 2018, Rothberg et al.
U.S. Appl. No. 15/626,801, filed Jun. 19, 2017, Rothberg et al.
U.S. Appl. No. 14/799,484, filed Jul. 14, 2015, Rothberg et al.
U.S. Appl. No. 15/178,025, filed Jun. 9, 2016, Rothberg et al.
U.S. Appl. No. 15/648,187, filed Jul. 12, 2017, Rothberg et al.
U.S. Appl. No. 15/689,863, filed Aug. 29, 2017, Rothberg et al.
International Search Report and Written Opinion dated Jul. 1, 2014 for Application No. PCT/US2014/014705.
Invitation to Pay Additional Fees dated Nov. 6, 2014 for Application No. PCT/US2014/025924.
International Search Report and Written Opinion dated Feb. 18, 2015 for Application No. PCT/US2014/025924.
International Search Report and Written Opinion dated Jun. 29, 2015 for Application No. PCT/US2015/026290.
International Preliminary Report on Patentability dated Aug. 20, 2015 for Application No. PCT/US2014/014705.
International Preliminary Report on Patentability dated Sep. 24, 2015 for Application No. PCT/US2014/025924.
International Search Report and Written Opinion dated Oct. 29, 2015 for Application No. PCT/US2015/040342.
International Preliminary Report on Patentability dated Oct. 27, 2016 for Application No. PCT/US2015/026290.
International Preliminary Report on Patentability dated Jan. 26, 2017 for Application No. PCT/US2015/040342.
Office Communication dated Feb. 13, 2015 for U.S. Appl. No. 14/172,383.
Office Communication dated Apr. 3, 2015 for U.S. Appl. No. 14/561,384.
Office Communication dated May 21, 2015 for U.S. Appl. No. 14/208,351.
Office Communication dated May 15, 2015 for U.S. Appl. No. 14/635,197.
Notice of Allowance dated Sep. 14, 2015 for U.S. Appl. No. 14/208,351.
Notice of Allowance dated Dec. 4, 2015 for U.S. Appl. No. 14/172,383.
Notice of Allowance dated Nov. 10, 2015 for U.S. Appl. No. 14/711,145.
Office Communication dated Jul. 12, 2016 for U.S. Appl. No. 14/172,840.
[No Author Listed], Sil-Via, TSI & Advanced Features. Silex Microsystems. http://www.silexmicrosystems.com/mems-foundry/sil-via-tsi-advanced-features/ [last accessed Jan. 6, 2015]. 4 pages.
Calmes et al., Highly Integrated 2-D Capacitive Micromachined Ultrasonic Transducers. 1999 IEEE Ultrason Symp. 1999;1163-6.
Cha et al., Influences of perforation ratio in characteristics of capacitive micromachined ultrasonic transducers in air. Sensors Actuators A. 2011;171:191-8.
Cheng et al., An Efficient Electrical Addressing Method Using Through-Wafer Vias for Two-Dimensional Ultrasonic Arrays. 2000 IEEE Ultrasonics Symposium. 2000;2:1179-82.
Cheng et al., Electrical Through-Wafer Interconnects with Sub-PicoFarad Parasitic Capacitance. 2001 Microelectromechan Syst Conf. Aug. 24, 2001;18-21.
Daft et al., Microfabricated ultrasonic transducers monolithically integrated with high voltage electronics. Proc Ultrason Symp. 2004;493-6.
Dixon-Warren, Overview of MEMS microphone technologies for consumer applications. MEMS J. Mar. 8, 2011. http://www.memsjournal.com/2011/03/overview-of-mems-microphone-technologies-for-consumer-applications.html [last accessed Feb. 19, 2014]. 10 pages.
Doody et al., Modeling and Characterization of CMOS-Fabricated Capacitive Micromachined Ultrasound Transducers. J Microelectromech Sys. Feb. 1, 2011;20(1):104-18.
Eccardt et al., Micromachined ultrasound transducers with improved coupling factors from a CMOS compatible process. Ultrasonics. Mar. 2000;38:774-80.
Eccardt et al., Surface micromachined ultrasound transducer in CMOS technology. Proc Ultrason Symp. 1996;959-62.
Gurun et al., Front-end CMOS electronics for monolithic integration with CMUT arrays: circuit design and initial experimental results. Proc Ultrason Symp. 2008;390-3.
Helin et al., Poly-SiGe-based CMUT array with high acoustical pressure. MEMS. 2012 IEEE 25th International Conference on Micro Electro Mechanical Systems. Jan. 29, 2012;305-8.
Kim et al., Design and Test of a Fully Controllable 64×128 2-D CMUT Array Integrated with Reconfigurable Frontend ASICs for

(56) References Cited

OTHER PUBLICATIONS

Volumetric Ultrasound Imaging. IEEE. International Ultrasonics Symposium Proceedings. Oct. 7-10, 2012;77-80. doi: 10.1109/ULTSYM.2012.0019.

Knight et al., Low Temperature Fabrication of Immersion Capacitive Micromachined Ultrasonic Transducers on Silicon and Dielectric Substrates. IEEE Trans Ultrason Ferroelectr Freq Contr. Oct. 2004;51(10):1324-33.

Kupnik et al., CMUT Fabrication Based on a Thick Buried Oxide Layer. Proc IEEE Ultrason Symp. Oct. 2010;2010:547-550. doi:10.1109/ULTSYM.2010.5935935. Epub Jun. 8, 2012. 10 pages.

Kupnik et al., Wafer-Bonded CMUT Meets CMOS. 2010 CMOS Emerging Technology Workshop. May 21, 2010;1-22.

Lemmerhirt et al., A 32×32 capacitive micromachined ultrasonic transducer array manufactured in standard CMOS. IEEE Trans Ultrason Ferroelectr Freq Control. Jul. 2012;59(7):1521-36. doi: 10.1109/TUFFC.2012.2352.

Lemmerhirt et al., An electronically-scanned CMUT-in-CMOS transducer for hemodialysis vascular access monitoring. Ultrason Symp. 2011 IEEE International Conference. Oct. 18, 2011;2193-6.

Lin et al., Packaging of Large and Low-Pitch Size 2D Ultrasonic Transducer Arrays. MEMS Conf. 2010;508-11.

Lu et al., Investigation of thermal stress influence on CMUT in standard CMOS process. Info Auto. 2009 ICIA International Conference. Jun. 22, 2009;1447-51.

Manzanares et al., Air-coupled MUMPs capacitive micromachined ultrasonic transducers with resonant cavities. Ultrason. 2012;52:482-9.

Nikoozadeh et al., Forward-Looking Intracardiac Ultrasound Imaging Using a 1-D CMUT Array Integrated With Custom Front-End Electronics. IEEE Trans Ultrason Ferroelectr Freq Contr. Dec. 2008;55(12):2651-60.

Noble et al., A cost-effective and manufacturable route to the fabrication of high-density 2D micromachined ultrasonic transducer arrays and (CMOS) signal conditioning electronics on the same silicon substrate. Proc Ultrason Symp. 2001;941-5.

Noble et al., Low-temperature micromachined CMUTs with fully-integrated analogue front-end electronics. Proc Ultrason Symp. 2002;1045-50.

Oralkan et al., Volumetric Imaging Using 2D Capacitive Micromachined Ultrasonic Transducer Arrays (CMUTs): Initial Results. 2002 IEEE Ultrason Symp. 2002;1083-6.

Oralkan et al., Volumetric Ultrasound Imaging Using 2-D CMUT Arrays. IEEE Trans Ultrason Ferroelectr Freq Contr. Nov. 2003;50(11):1581-94.

Park et al., Fabrication of Capacitive Micromachined Ultrasonic Transducers via Local Oxidation and Direct Wafer Bonding. J Microelectromechan Syst. Feb. 2011;20(1):95-103.

Torkkeli et al., Capacitative microphone with low-stress polysilicon membrane and high-stress polysilicon backplate. Sensors and Actuators. 2000;85:116-23.

Tsuji et al., Low Temperature Process for CMUT Fabrication with Wafer Bonding Technique. IEEE Intl Ultrason Symp Proc. 2010;551-4.

Um et al., An Analog-Digital-Hybrid Single-Chip RX Beamformer with Non-Uniform Sampling for 2D-CMUT Ultrasound Imaging to Achieve Wide Dynamic Range of Delay and Small Chip Area. IEEE International Solid-State Circuits Conference Feb. 12, 2014;426-8.

Wodnicki et al., Multi-Row Linear CMUT Array Using CMUTs and Multiplexing Electronics. Proc Ultrason Symp. 2009;2696-9.9.

Wolffenbuttel et al., Low-temperature silicon wafer-to-wafer bonding using gold at eutectic temperature. Sensors and Actuators A. 1994;43:223-9.

Wygant et al., Integration of 2D CMUT Arrays with Front-End Electronics for Volumetric Ultrasound Imaging. IEEE Trans Ultrason Ferroelectr Freq Contr. Feb. 2008;55(2):327-42.

Xu et al., Characterization of improved Capacitive Micromachined Ultrasonic Transducers (CMUTs) using ALD high-[Kappa] dielectric isola. MEMS. 2014 IEEE 27th International Conference on Micro Electro Mechanical Systems. Jan. 26, 2014;584-7.

Yu et al., Dual-bottom-electrode CMUT based on standard CMOS process. NEMS. 2001 IEEE International Conference. Feb. 20, 2011;21-4.

Zahorian et al., Single chip CMUT arrays with integrated CMOS electronics: fabrication process development and experimental results. Proc Ultrason Symp. 2008;386-9.

Zhuang et al., Integration of trench-isolated through-wafer interconnects with 2d capacitive micromachined ultrasonic transducer arrays. Sensors Actuators A. 2007;138:221-9.

Zhuang et al., Wafer-bonded 2-D CMUT arrays incorporating through-wafer trench-isolated interconnects with a supporting frame. IEEE Trans Ultrason Ferroelectr Freq Control. Jan. 2009;56(1):182-92. doi: 10.1109/TUFFC.2009.1018.

U.S. Appl. No. 16/109,703, filed Aug. 22, 2018, Rothberg et al.

COMPLEMENTARY METAL OXIDE SEMICONDUCTOR (CMOS) ULTRASONIC TRANSDUCERS AND METHODS FOR FORMING THE SAME

CROSS-REFERENCE TO RELATED APPLICATIONS

This Application is a continuation of and claims the benefit under 35 U.S.C. § 120 of U.S. application Ser. No. 15/626,801, issued as U.S. Pat. No. 9,944,514, filed Jun. 19, 2017, and entitled "COMPLEMENTARY METAL OXIDE SEMICONDUCTOR (CMOS) ULTRASONIC TRANSDUCERS AND METHODS FOR FORMING THE SAME", which is incorporated herein by reference in its entirety.

U.S. patent application Ser. No. 15/626,801 is a continuation of and claims the benefit under 35 U.S.C. § 120 of U.S. application Ser. No. 15/291,697, issued as U.S. Pat. No. 9,738,514, filed Oct. 12, 2016 and entitled "COMPLEMENTARY METAL OXIDE SEMICONDUCTOR (CMOS) ULTRASONIC TRANSDUCERS AND METHODS FOR FORMING THE SAME", which is incorporated herein by reference in its entirety.

U.S. patent application Ser. No. 15/291,697 is a continuation of and claims the benefit under 35 U.S.C. § 120 of U.S. application Ser. No. 15/042,931, issued as U.S. Pat. No. 9,499,395, filed on Feb. 12, 2016 and entitled "COMPLEMENTARY METAL OXIDE SEMICONDUCTOR (CMOS) ULTRASONIC TRANSDUCERS AND METHODS FOR FORMING THE SAME", which is incorporated herein by reference in its entirety.

U.S. patent application Ser. No. 15/042,931 is a continuation of and claims the benefit under 35 U.S.C. § 120 of U.S. patent application Ser. No. 14/711,145, issued as U.S. Pat. No. 9,290,375, filed on May 13, 2015 and entitled "COMPLEMENTARY METAL OXIDE SEMICONDUCTOR (CMOS) ULTRASONIC TRANSDUCERS AND METHODS FOR FORMING THE SAME", which is incorporated herein by reference in its entirety.

U.S. patent application Ser. No. 14/711,145 is a continuation of and claims the benefit under 35 U.S.C. § 120 of U.S. patent application Ser. No. 14/561,384, issued as U.S. Pat. No. 9,061,318, filed on Dec. 5, 2014 and entitled "COMPLEMENTARY METAL OXIDE SEMICONDUCTOR (CMOS) ULTRASONIC TRANSDUCERS AND METHODS FOR FORMING THE SAME", which is incorporated herein by reference in its entirety.

U.S. patent application Ser. No. 14/561,384 is a continuation of and claims the benefit under 35 U.S.C. § 120 of U.S. patent application Ser. No. 14/208,351, issued as U.S. Pat. No. 9,242,275, filed on Mar. 13, 2014 under and entitled "COMPLEMENTARY METAL OXIDE SEMICONDUCTOR (CMOS) ULTRASONIC TRANSDUCERS AND METHODS FOR FORMING THE SAME", which is incorporated herein by reference in its entirety.

U.S. patent application Ser. No. 14/208,351 claims the benefit under 35 U.S.C. § 119(e) of U.S. Provisional Patent Application Ser. No. 61/794,744, filed on Mar. 15, 2013 and entitled "COMPLEMENTARY METAL OXIDE SEMICONDUCTOR (CMOS) ULTRASONIC TRANSDUCERS AND METHODS FOR FORMING THE SAME", which is incorporated herein by reference in its entirety.

BACKGROUND

Field

The technology described herein relates to complementary metal oxide semiconductor (CMOS) transducers and methods for forming the same.

Related Art

Capacitive Micromachined Ultrasonic Transducers (CMUTs) are known devices that include a membrane above a micromachined cavity. The membrane may be used to transduce an acoustic signal into an electric signal, or vice versa. Thus, CMUTs can operate as ultrasonic transducers.

Two types of processes can be used to fabricate CMUTs. Sacrificial layer processes form the membrane of the CMUT on a first substrate above a sacrificial layer. Removal of the sacrificial layer leaves behind the membrane above a cavity. Wafer bonding processes bond two wafers together to form a cavity with a membrane.

SUMMARY

Aspects of the present application are directed to methods for forming CMOS ultrasonic transducers (CUTs), which include an ultrasonic transducer formed on a CMOS wafer, as well as designs for such CUTs. For example, the methods may allow for the formation of devices having monolithically integrated ultrasonic transducers and CMOS integrated circuits. Thus, single substrate devices operating as ultrasound devices (e.g., for ultrasound imaging and/or high intensity focused ultrasound (HIFU)) are achieved.

According to an aspect of the present application, an apparatus is provided, comprising an ultrasonic transducer and an integrated circuit coupled to the ultrasonic transducer, the integrated circuit formed in a CMOS wafer. The ultrasonic transducer comprises a cavity formed in the CMOS wafer, a membrane formed of a material other than monocrystalline silicon overlying the cavity, and an electrical contact providing electrical connectivity between the membrane and the integrated circuit.

According to an aspect of the present application, a method of forming an ultrasonic transducer is provided, the method comprising forming a cavity in a CMOS wafer, and bonding a transfer wafer to the CMOS wafer, the transfer wafer having a front face formed of a material not including monocrystalline silicon. Bonding the transfer wafer to the CMOS wafer is performed below 450° C.

According to an aspect of the present application, an apparatus is provided, comprising a complementary metal oxide semiconductor (CMOS) wafer having an integrated circuit (IC) formed therein, a membrane disposed above a cavity in the CMOS wafer, the membrane being integrated with the CMOS wafer and having a first side proximate the cavity and a second side distal the cavity, and a conductive electrical path contacting the first side of the membrane proximate the cavity and electrically connecting the membrane to the IC.

According to an aspect of the present application, an ultrasonic transducer is provided, comprising: a substrate having a cavity formed therein, and a membrane integrated with the substrate and overlying the cavity. The membrane has a thickness between approximately 0.05 microns and approximately 1 micron.

According to an aspect of the present application, a method is provided comprising forming an ultrasonic transducer by forming a conductive electrical path connecting an integrated circuit (IC) in a complementary metal oxide semiconductor (CMOS) wafer to a first side of a membrane covering a cavity in the CMOS wafer, the first side of the membrane being proximate the cavity and the membrane further having a second side distal the cavity.

According to an aspect of the present application, a method of making an ultrasonic transducer is provided, the method comprising forming a covered cavity in a complementary metal oxide semiconductor (CMOS) wafer by sealing the cavity with a polysilicon or amorphous silicon membrane.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1A:
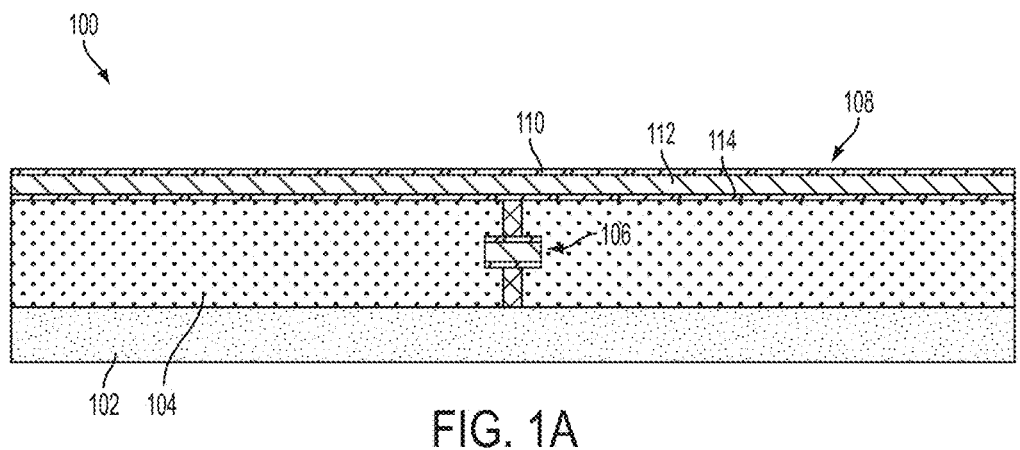
FIGS. 1A-1K illustrate a process sequence for fabricating a CMOS ultrasonic transducer (CUT) having a membrane formed above a cavity in a CMOS wafer, according to a non-limiting embodiment of the present application.

Existing methods for forming CMUTs are impractical for forming ultrasonic transducers integrated with CMOS wafers and, therefore, CMOS integrated circuits (ICs) on such wafers. Thus, such integrated ultrasonic transducers and ICs are nonexistent today. For example, existing methods for forming CMUTs do not provide a practical manner for making electrical connection between the CMUT and integrated circuits on a CMOS wafer. Also, existing methods do not adequately allow for scaling of CMUTs to sizes appropriate for compatibility with low voltage CMOS integrated circuits. Furthermore, CMUT manufacturing processes are too complex to be performed in a cost-effective manner suitable for large scale production of commercial devices, for example because they involve processing with complex materials and too many processing steps.

Accordingly, aspects of the present application provide scalable, relatively low cost methods of fabricating ultrasonic transducers integrated with CMOS wafers and, in some embodiments, CMOS ICs formed on the CMOS wafers. Such methods enable the formation of a new class of devices including monolithically integrated ultrasonic transducers and CMOS ICs, referred to herein as CMOS Ultrasonic Transducers (CUTs). The CUTs may be used to form ultrasound devices for ultrasound imaging and/or high intensity focused ultrasound (HIFU) applications and/or other ultrasound applications.

To facilitate integration of ultrasonic transducer technology with CMOS processing techniques in a manner suitable for scalable, large scale production of CUTs, it may be desirable for a manufacturing process to exhibit one or more of various characteristics. For example, the process may be suitable for forming ultrasonic transducers without damaging the CMOS wafer and any circuitry (e.g., an IC) formed thereon. Thus, the process may avoid processing steps which require temperatures sufficiently high to cause damage to a CMOS wafer and CMOS ICs. Rather, low temperature processes may be employed. The process may utilize materials common to CMOS process lines, and which do not require extensive effort or time to fabricate and/or deposit, such as polycrystalline and/or amorphous forms of materials rather than single crystal (monocrystalline) forms. The process may provide for suitable manners of making direct or indirect electrical connection to individual ultrasonic transducer cells. The process may also be suitable for making ultrasonic transducers of suitable sizes to enable low voltage operation (e.g., below 70 V, below 50 V, below 30 V, or other suitably low voltages for transducer operation), thus making them more compatible with low voltage CMOS ICs. For example, the processes may be suitable for making membranes of sufficient sizes (e.g., sufficiently small thicknesses) and shapes for operation as low voltage devices while still delivering desired transducer behavior (e.g., desired frequencies of operation, bandwidths, power, or other characteristics). Other characteristics of a manufacturing process may also be desirable in some embodiments to facilitate integration of ultrasonic transducers with CMOS wafers.

Accordingly, aspects of the present application implement low temperature (e.g., below 450° C.) wafer bonding to form ultrasonic transducer membranes on CMOS wafers. Low temperature in this context may, in some embodiments, be below 450° C., below 400° C., below 350° C., between 200° C. and 450° C., any temperature within that range, or any suitable temperature for preserving structures on a CMOS wafer). Thus, the bonding processes as well as other fabrication steps for forming CUTs according to some embodiments may avoid any anneals above 450° C. In some embodiments, the membranes may be formed of relatively simple and inexpensive materials, such as polycrystalline silicon, amorphous silicon, silicon dioxide, silicon nitride (SiN), and titanium nitride (TiN). The membranes may also be thin, and in at least some embodiments thinner than those previously achievable in CMUTs. Use of such thin membranes may facilitate the formation of ultrasonic transducers operable at voltages sufficiently low to comply with CMOS technology, and thus may facilitate formation of CUTs.

Aspects of the present application provide various designs and processes for making electrical connection to the membrane of an ultrasonic transducer in a manner that facilitates integration of the ultrasonic transducer with a CMOS integrated circuit. In some embodiments, connection may be made from a cavity-side (e.g., a bottom side) of the membrane. Such connection may be made by way of an embedded via, a conductive standoff or cavity wall, or in any other suitable manner. Such electrical interconnections may provide local connection to the membrane rather than global connection, whereby the connection to individual membranes may be made close to related circuitry and on an individual basis rather than at great distances from related circuitry and on a multi-membrane basis. Such capability for local connection to membranes may enable a broader range of operating schemes than those afforded by global interconnection, for example because of the capability for individualized control of membranes.

Aspects of the present application provide CUTs having a piston configuration, in which a membrane includes one or more relatively thick center portions and a relatively thin surrounding (or outer) portion. Such a structure may be referred to herein as a piston membrane. In some embodiments, the piston membrane may be fully formed on a transfer wafer prior to wafer bonding. The transfer wafer may then be bonded to a CMOS wafer with low temperature processing methods and the piston membrane removed from the remainder of the transfer wafer. In this manner, piston membranes formed of a single material defining a unitary body may be formed, and such piston membranes may be formed of materials that are processed at temperatures sufficiently high to damage CMOS ICs if such processing had occurred after the wafer bonding.

The aspects and embodiments described above, as well as additional aspects and embodiments, are described further below. These aspects and/or embodiments may be used individually, all together, or in any combination of two or more, as the application is not limited in this respect.

A first process for forming an ultrasonic transducer having a membrane above a cavity in a CMOS wafer is now described. Referring to FIG. 1A, the process may begin with a CMOS wafer 100 including a substrate 102, a dielectric or insulating layer 104, a first metallization layer 106 and a second metallization layer 108, which in some embodiments may be a top metallization layer of the CMOS wafer 100.

The substrate 102 may be silicon or any other suitable CMOS substrate. In some embodiments, the CMOS wafer 100 may include CMOS integrated circuitry (IC), and thus the substrate 102 may be a suitable substrate for supporting such circuitry.

The insulating layer 104 may be formed of $SiO_2$ or any other suitable dielectric insulating material. In some embodiments, the insulating layer 104 may be formed via tetraethyl orthosilicate (TEOS), though alternative processes may be used.

While the CMOS wafer 100 is shown as including two metallization layers 106 and 108, it should be appreciated that CMOS wafers according to the various aspects of the present application are not limited to having two metallization layers, but rather may have any suitable number of metallization layers, including more than two in some embodiments. Such metallization layers may be used for wiring (e.g., as wiring layers) in some embodiments, though not all embodiments are limited in this respect.

The first and second metallization layers 106 and 108 may have any suitable construction. In the embodiment illustrated, at least the second metallization layer 108 may have a multi-layer construction, including a middle conductive layer 112 (e.g., formed of aluminum or other suitable conductive material) and upper and lower liner layers 110 and 114, respectively. The liner layers 110 and 114 may be formed of titanium nitride (TiN) or other suitable conductive material (e.g., metals other than TiN, such as tantalum, or other suitable metals for acting as a liner). In some embodiments, the upper liner layer 110 may be used as an etch stop, for example during one or more etch steps used in as part of a process for forming a cavity for an ultrasonic transducer. Thus, the liner layer 110 may be formed of a material suitable to act as an etch stop in some embodiments. Moreover, while not shown, the first and second metallization layers 106 and 108, as well as any other metallization layers described herein, may optionally include silicon oxynitride (SiON) as an upper layer (e.g., on top of liner layer 110) to serve as an anti-reflective coating during lithography stages.

In some embodiments, it may be desirable to form an electrode from the second metallization layer 108 serving as an electrode of an ultrasonic transducer. Also, the second metallization layer 108 may be used to make electrical contact to a membrane of a CUT to be formed on the CMOS wafer. Accordingly, as shown in FIG. 1B, the second metallization layer 108 may be suitably patterned to form an electrode 116 and one or more contacts 118.

Figure 1B:
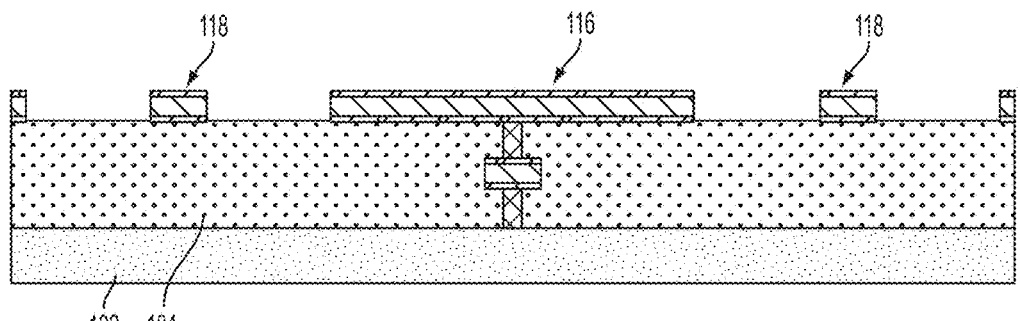

While FIG. 1B illustrates a configuration in which an electrode and electrical contacts are formed on a CMOS wafer from a metallization layer, it should be appreciated that other manners of forming an electrode (e.g., electrode 116) and/or electrical contacts (e.g., electrical contacts 118) may be implemented. For example, conductive materials other than metals but suitable to act as electrodes and/or electrical contacts may be suitably processed on the CMOS wafer to form the illustrated electrode and/or electrical contacts.

Figure 1C:
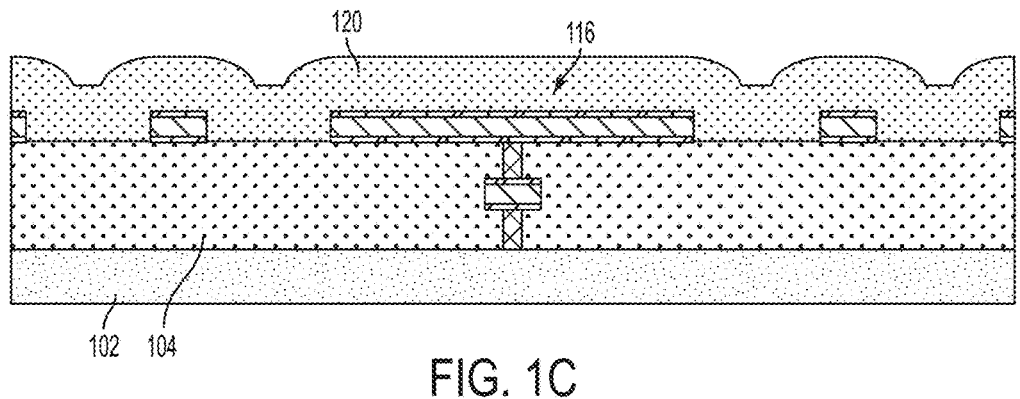

An insulating layer 120 may then be deposited as shown in FIG. 1C. The insulating layer 120 may be $SiO_2$ or any other suitable insulator, and may be formed in any suitable manner. In some embodiments, the insulating layer 120 may be formed by high density plasma (HDP) deposition. The insulating layer 120 may then be planarized (not shown), for example using chemical mechanical polishing (CMP) or other suitable planarization technique.

Figure 1D:
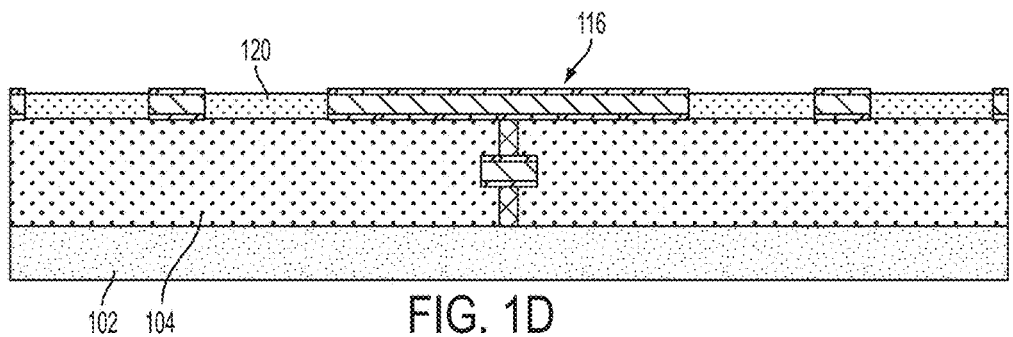

In FIG. 1D, the insulating layer 120 may be etched as shown to expose the upper surface of the electrode 116 and electrical contacts 118. In some embodiments, the upper liner layer 110 may be used as an etch stop for a selective etch used to etch the insulating layer 120. As an example, the liner layer 110 may be formed of TiN and may be used as an etch stop, though not all embodiments are limited in this respect.

Figure 1E:
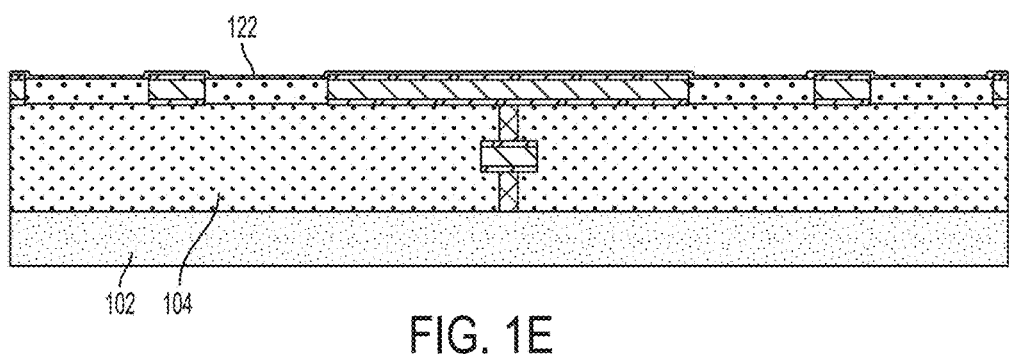
Figure 1F:
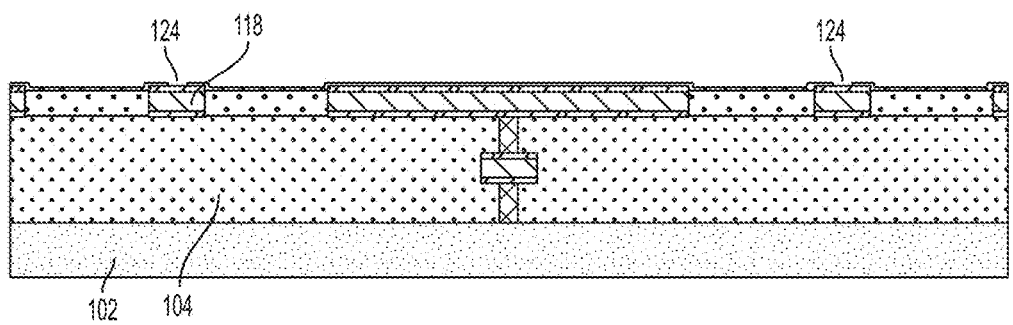

A further insulating layer 122 may be deposited as shown in FIG. 1E to cover the upper surfaces of the electrode 116 and electrical contacts 118 and may then be patterned as shown in FIG. 1F to open contact holes 124 for the electrical contacts 118. The insulating layer 122 may be $SiO_2$ or any other suitable insulator.

Figure 1G:
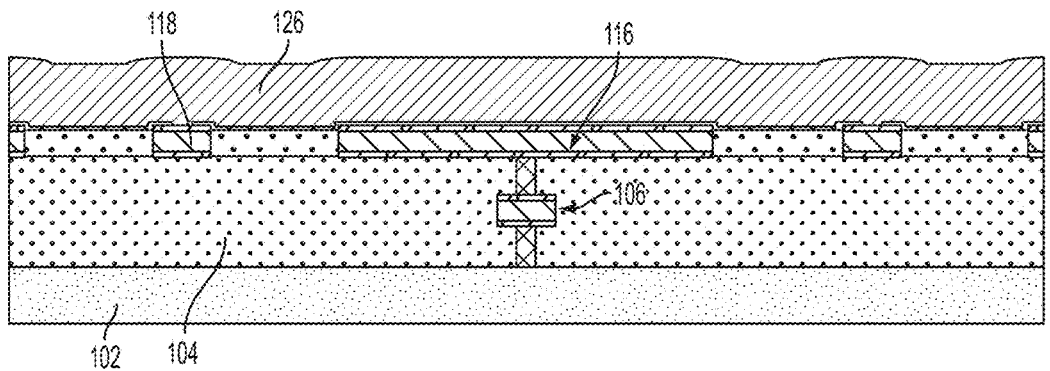

As shown in FIG. 1G, a conductive layer 126 may be deposited. The conductive layer may be used to form electrical contacts to a membrane of an ultrasonic transducer, as will be shown in connection with FIG. 1J. Also, the conductive layer 126 may be patterned to form a cavity therein for a CUT, with a remaining portion of the conductive layer 126 defining one or more sidewalls of the cavity. In some embodiments, then, the conductive layer 126 may also represent a spacer in that a membrane may be separated from the surface of the CMOS wafer 100 by the height of the conductive layer 126. Thus, the conductive layer 126 may serve one or more of multiple possible functions.

The conductive layer 126 may be formed of any suitable conductive material. In some embodiments, the conductive layer 126 may be formed of a metal. For example, the conductive layer 126 may be TiN in some embodiments.

Figure 1H:
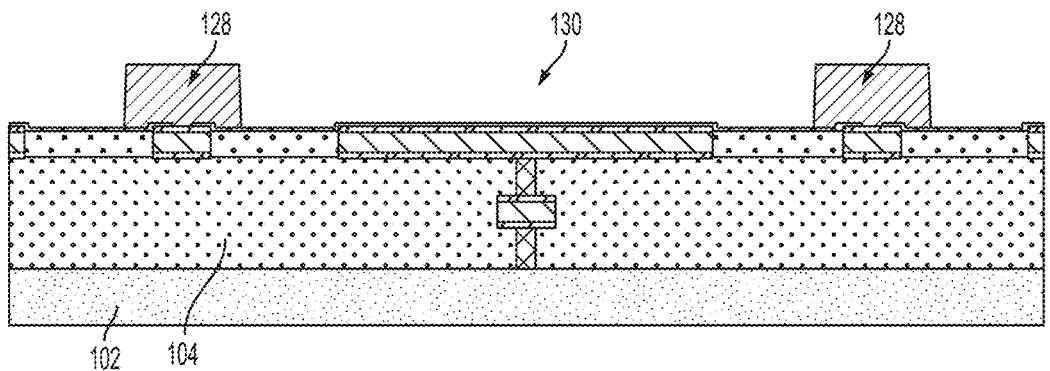

The conductive layer 126 may be planarized (not shown) using CMP or other suitable planarization technique, and then may be patterned as shown in FIG. 1H to form contacts 128. It can be seen that at this stage a cavity 130 has been formed in the CMOS wafer with the contacts 128 serving to at least partially define the cavity. Namely, the contacts 128 (which in some embodiments may represent a single contact forming a closed contour) function as sidewalls of the cavity 130 in the embodiment illustrated and, as will be further appreciated from consideration of FIG. 1K, create a standoff between the electrode 116 and a membrane overlying the cavity 130.

Figure 1I:
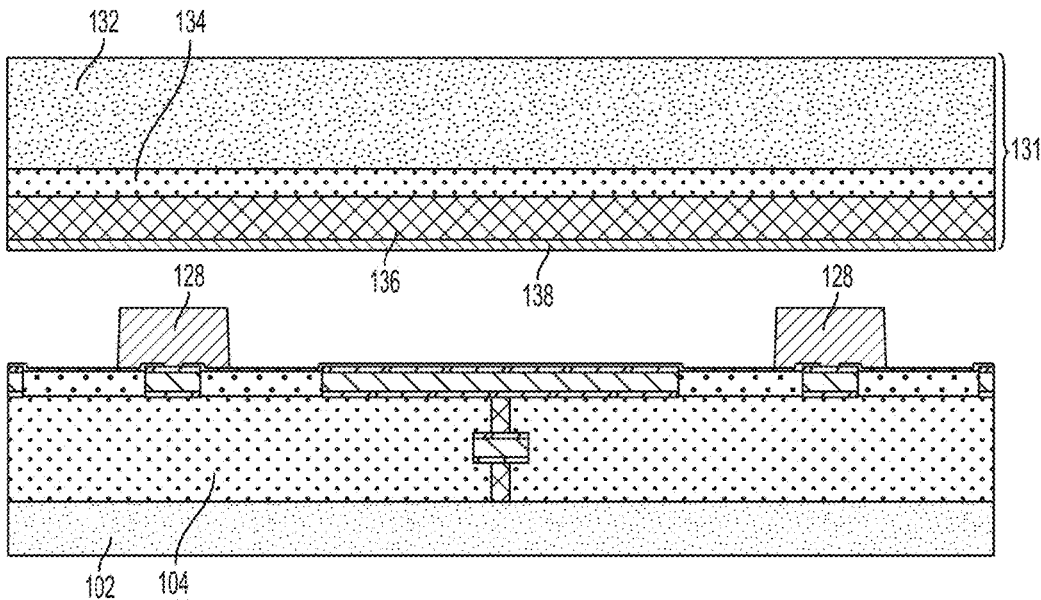
Figure 1J:
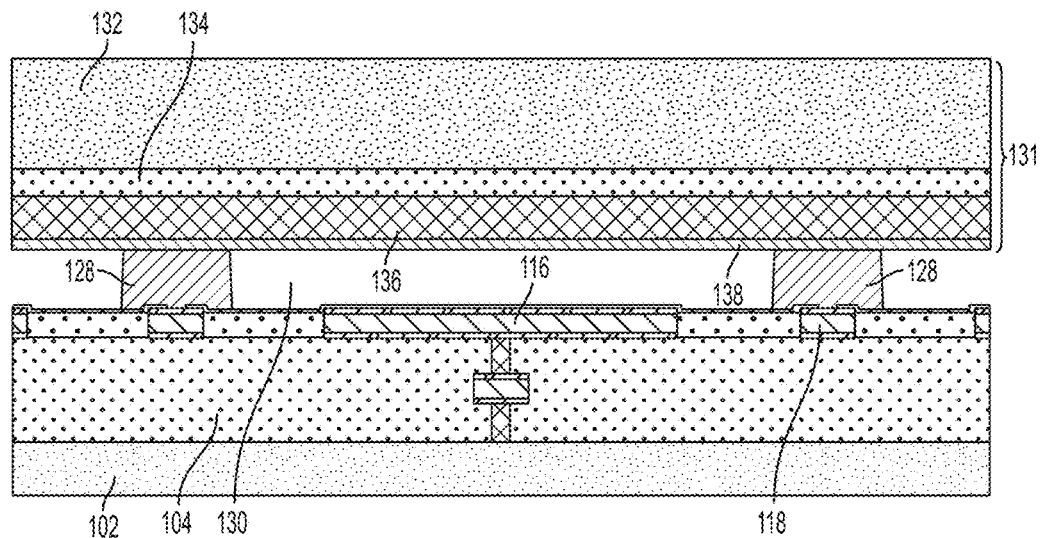

As shown in FIGS. 1I-1J, a second wafer 131 may be bonded to the CMOS wafer. In general, the second wafer may be any suitable type of wafer, such as a bulk silicon wafer, a silicon-on-insulator (SOI) wafer, or an engineered substrate including a polysilicon or amorphous silicon layer with an insulating layer between a single crystal silicon layer and the polysilicon or amorphous silicon layer. In the embodiment illustrated, the second wafer 131 may include four layers including a base layer or handle layer 132, insulating layer 134, layer 136, and layer 138. The second wafer 131 may be used to transfer layers 136 and 138 to the CMOS wafer for forming a membrane over cavity 130, and thus may be referred to herein as a transfer wafer.

As a non-limiting example of suitable materials making up the second wafer 131, the base layer 132 may be a silicon layer (e.g., single crystal silicon), the insulating layer 134 may be $SiO_2$ and may represent a buried oxide (BOX) layer, and layer 136 may be silicon. In some embodiments, the layer 136 may be degeneratively doped silicon phosphide (SiP+). In some embodiments, the layer 136 may be polysilicon or amorphous silicon, though other embodiments may utilize single crystal silicon. The layer 138 may be formed of a material suitable for bonding to the contacts 128 on the CMOS wafer. For example, the contacts 128 and layer 138 may be formed of the same material. In some embodiments, the contacts 128 and layer 138 may be formed of TiN.

The process used for bonding the second wafer 131 to the CMOS wafer 100 may be a low temperature bonding process, for example not exceeding 450° C. In some embodiments, the temperature of the bonding process may be between approximately 200° C. and 450° C., between approximately 300° C. and approximately 400° C., any temperature(s) within those ranges, any other temperature described herein for low temperature bonding, or any other suitable temperature. Thus, damage to the metallization layers on the CMOS wafer, and any ICs on the CMOS wafer, may be avoided.

The wafer bonding process may be one of various types. In some embodiments, the wafer bonding may be direct bonding (i.e., fusion bonding). Thus, the wafer bonding may involve energizing respective surfaces of the CMOS and second wafers and then pressing the wafers together with suitable pressure to create the bond. A low temperature anneal may be performed. While fusion bonding represents one example of a suitable bonding technique, other bonding techniques may alternatively be used, including for example bonding two wafers through the use of one or more intermediate layers (e.g., adhesive(s)). In some embodiments, anodic or plasma assisted bonding may be used.

The bonding illustrated in FIGS. 1I-1J may result in the second wafer 131 being monolithically integrated with the CMOS wafer 100. Thus, the two may form a unitary body in some situations.

A membrane may then be formed from the second wafer 131. The second wafer 131 may be thinned from the backside. Such thinning may be performed in stages. For example, mechanical grinding providing coarse thickness control (e.g., 10 micron control) may initially be implemented to remove a relatively large amount of the bulk wafer. In some embodiments, the thickness control of the mechanical grinding may vary from coarse to fine as the thinning process progresses. Then, CMP may be performed on the backside, for example to get to a point close to the layer 136. Next, a selective etch, such as a selective chemical etch, may be performed to stop on the layer 136. Other manners of thinning are also possible.

Figure 1K:
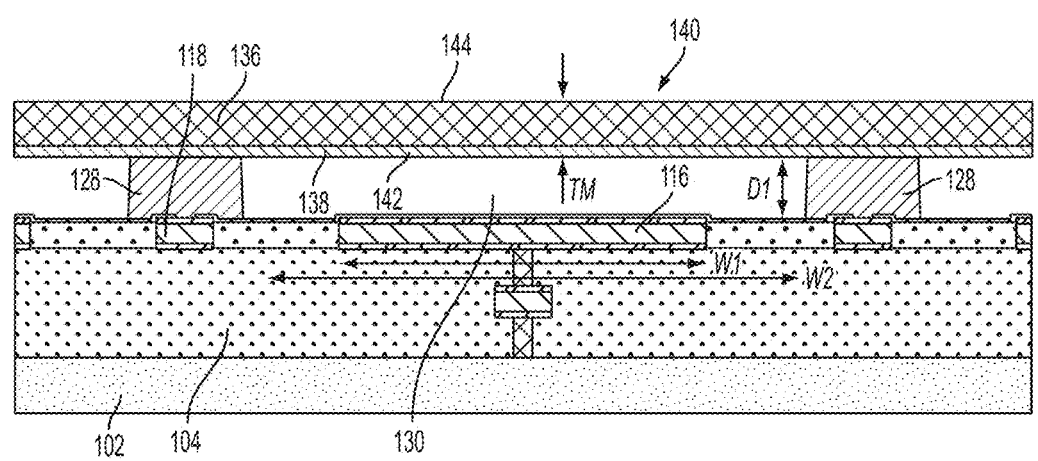

Thus, as shown in FIG. 1K, the base layer or handle layer 132 and insulating layer 134 may be removed. A membrane 140 formed of the layer 136 and layer 138 may remain. The membrane may be any suitable thickness TM, non-limiting examples of which are described below. In some embodiments, the layer 136 may be etched or otherwise thinned to provide a desired membrane thickness.

Various features of the structure illustrated in FIG. 1K are noted. First, the structure includes a sealed cavity 130 which is sealed by the membrane 140. Also, the sidewalls of the cavity are conductive, i.e., the contacts 128 are conductive and form the sidewalls of the sealed cavity. In this respect, the contacts 128 represent a conductive standoff for the membrane 140 from the surface of the CMOS wafer. The contacts 128 may be relatively large area electrical contacts and make contact with a relatively large area of the membrane, thus providing a low resistivity electrical path to/from the membrane. For example, the contacts may provide electrical control between the membrane and an IC on the CMOS wafer (e.g., disposed beneath the cavity) which may interact with the membrane to provide/receive electrical signals and thus in some embodiments control operation of the membrane.

Moreover, it is noted that the membrane 140 has a first side 142 proximate the cavity 130 and a second side 144 distal the cavity, and that direct electrical contact is made to the first side 142 via the contacts 128. The first side 142 may be referred to as a bottom side of the membrane and the second side 144 may be referred to as a top side of the membrane. Local connection to the membrane 140 may be made in this manner, and the membrane 140 may be connected to integrated circuitry in the CMOS wafer via this connection (e.g., via contact 118). In some embodiments, an IC may be positioned beneath the cavity 130 and the conductive path configuration illustrated may facilitate making connection between the integrated circuitry beneath the cavity and the membrane 140. The configuration of FIG. 1K provides a non-limiting example of an embedded contact to the membrane, in that electrical contact is provided by way of a conductive path in the CMOS wafer (e.g., to contact 118) rather than a contact made on the second side 144. Such a configuration may be preferable to making electrical contact on the second side 144 since any contact on the second side 144 may (negatively) impact vibration of the membrane 140.

Also, it is noted that in the embodiment of FIG. 1K the electrode 116 is narrower than the cavity 130. Namely, the electrode 116 has a width W1 less than a width W2 of the cavity 130. Such a configuration may be desirable at least in those embodiments in which the cavity has conductive sidewalls (e.g., the contacts 128) to provide electrical isolation between the sidewalls and the electrode.

Moreover, it is noted that the structure of FIG. 1K may be altered by not including the layer 138 in an embodiment. Thus, in an embodiment a direct bond may be formed between contacts 128 (e.g., formed of TiN) and layer 136 (e.g., silicon).

The structure illustrated in FIG. 1K may have any suitable dimensions. Non-limiting examples of dimensions for the membrane 140 and cavity 130 are described further below.

As non-limiting examples, the width W2 of the cavity 130 may be between approximately 5 microns and approximately 500 microns, between approximately 20 microns and approximately 100 microns, may be approximately 30 microns, approximately 40 microns, approximately 50 microns, any width or range of widths in between, or any other suitable width. In some embodiments, the width may be selected to maximize the void fraction, i.e., the amount of area consumed by the cavity compared to the amount of area consumed by surrounding structures. The width dimension may also be used to identify the aperture size of the cavity, and thus the cavities may have apertures of any of the values described above or any other suitable values.

The depth D1 may be between approximately 0.05 microns and approximately 10 microns, between approximately 0.1 microns and approximately 5 microns, between approximately 0.5 microns and approximately 1.5 microns, any depth or range of depths in between, or any other suitable depth. If the contacts 128 are formed of TiN, it may be preferable in such embodiments for D1 to be less than 5 microns, since TiN is commonly formed as a thin film. In some embodiments, the cavity dimensions and/or the membrane thickness of any membrane overlying the cavity may impact the frequency behavior of the membrane, and thus may be selected to provide a desired frequency behavior (e.g., a desired resonance frequency of the membrane). For example, it may be desired in some embodiments to have an ultrasonic transducer with a center resonance frequency of between approximately 20 kHz and approximately 200 MHz, between approximately 1 MHz and approximately 10 MHz, between approximately 2 MHz and approximately 5 MHz, between approximately 50 kHz and approximately 200 kHz, of approximately 2.5 MHz, approximately 4 MHz, any frequency or range of frequencies in between, or any other suitable frequency. For example, it may be desired to use the devices in air, gas, water, or other environments, for example for medical imaging, materials analysis, or for other reasons for which various frequencies of operation may be desired. The dimensions of the cavity and/or membrane may be selected accordingly.

The membrane thickness TM (e.g., as measured in the direction generally parallel to the depth D1) may be less than 100 microns, less than 50 microns, less than 40 microns, less than 30 microns, less than 20 microns, less than 10 microns, less than 5 microns, less than 1 micron, less than 0.1 microns, any range of thicknesses in between, or any other suitable thickness. The thickness may be selected in some embodiments based on a desired acoustic behavior of the membrane, such as a desired resonance frequency of the membrane.

Figure 22A:
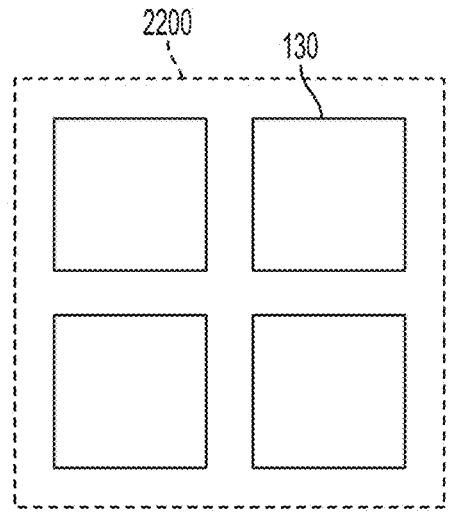
FIGS. 22A-22D illustrate various shapes for cavities of CUTS, according to non-limiting embodiments of the present application.
Figure 22B:
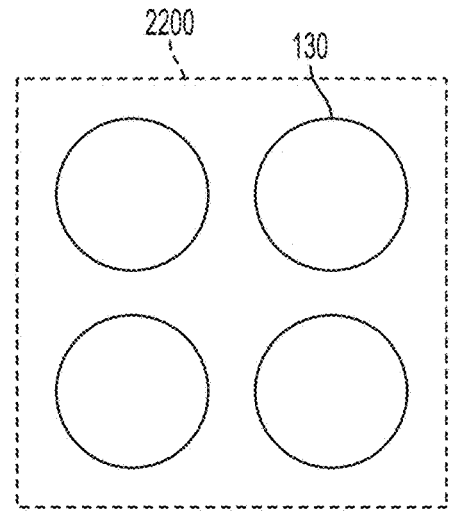
Figure 22C:
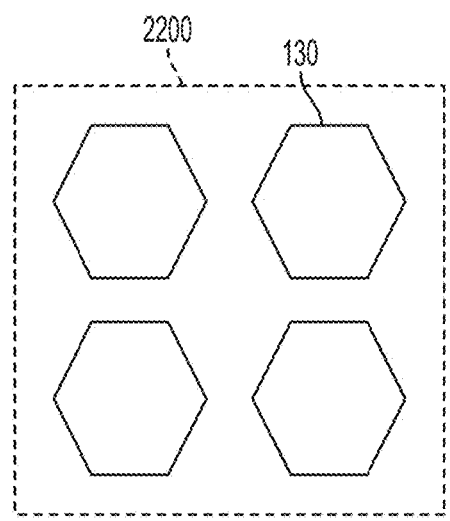
Figure 22D:
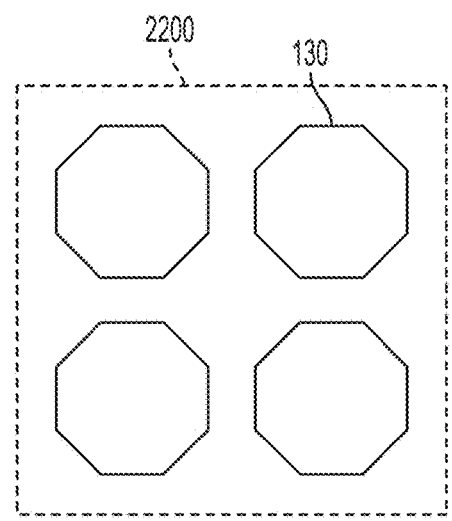

Also, it should be appreciated that the cavity 130, and more generally the cavities of any embodiments described herein, may have various shapes, and that when multiple cavities are formed not all cavities need have the same shape or size. For example, FIGS. 22A-22D illustrate various potential shapes for cavity 130 and the other cavities described herein. Specifically, FIGS. 22A-22D illustrate top views of a portion 2200 of a CMOS wafer having cavities 130 formed therein of various shapes. FIG. 22A illustrates that the cavities 130 may have a square aperture. FIG. 22B illustrates the cavities 130 may have a circular aperture. FIG. 22C illustrates the cavities may have a hexagonal aperture. FIG. 22D illustrates the cavities 130 may have an octagonal aperture. Other shapes are also possible.

While the portion 2200 is shown as including four cavities, it should be appreciated that aspects of the present application provide for one or more such cavities to be formed in a CMOS wafer. In some embodiments a single substrate (e.g., a single CMOS wafer) may have tens, hundreds, thousands, tens of thousands, hundreds of thousands, or millions of CUTs (and corresponding cavities) formed therein.

FIG. 1K illustrates an ultrasonic transducer which has a membrane 140 overlying the cavity 130, wherein the membrane has a substantially uniform thickness. In some embodiments, it may be desirable for the membrane to have a non-uniform thickness. For example, it may be desirable for the membrane to be configured as a piston, with a center portion having a greater thickness than an outer portion of the membrane, non-limiting examples of which are described below.

Ultrasonic transducers such as that illustrated in FIG. 1K may be used to send and/or receive acoustic signals. The operation of the transducer in terms of power generated, frequencies of operation (e.g., bandwidth), and voltages needed to control vibration of the membrane may depend on the shape and size of the membrane. A membrane shaped as a piston with a center mass-like portion that is connected to a CMOS wafer by a thinner peripheral portion may provide various beneficial operating characteristics.

Accordingly, an aspect of the present application provides ultrasonic transducers having piston membranes. Such transducers may be formed by wafer bonding processes according to some embodiments of the present application. In general, the thicker center portion of such membranes may be formed on the top side or bottom side of the membrane, and may be formed prior to or after wafer bonding. Non-limiting examples of suitable fabrication processes are now described.

According to an embodiment of the present application, a method of making a piston membrane having a thicker center portion on a topside of the membrane and formed from a transfer wafer is provided. The method may involve the same processing steps previously described in connection with FIGS. 1A-1H to arrive at the structure of FIG. 1H. From that point, as shown in FIGS. 2A-2B, a transfer wafer 201 may be bonded with the CMOS wafer, for example using a low temperature (below 450° C.) direct bonding technique as previously described.

Figure 2A:
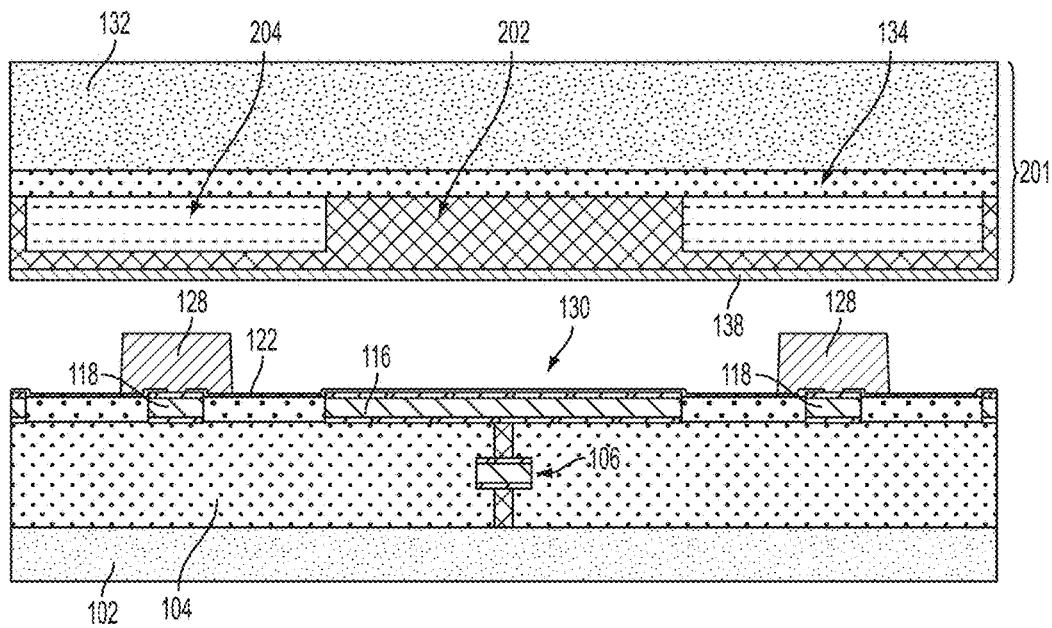
FIGS. 2A-2C illustrate a process sequence for fabricating a CUT having a piston membrane in which the piston membrane is transferred from a transfer wafer, according to a non-limiting embodiment of the present application.
Figure 2B:
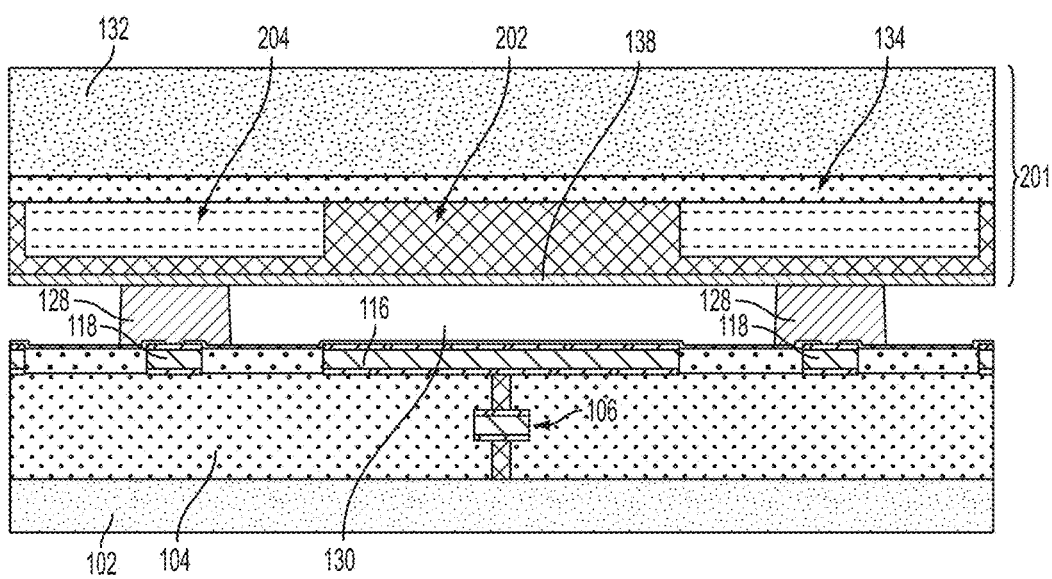

The transfer wafer 201 of FIGS. 2A-2B includes the base layer 132, insulating layer 134, and layer 138. The transfer wafer also includes piston 202, and layer 204, which in some embodiments may be an insulating layer such as $SiO_2$ (e.g., formed via tetraethylorthosilicate (TEOS) or other suitable process), but which is not limited to being formed of any particular type of material. The piston 202 may be formed of silicon in some embodiments, and in some embodiments is formed of polysilicon or amorphous silicon, although other embodiments may use single crystal silicon. The use of polysilicon or amorphous silicon may simplify the manufacturing process and/or reduce cost in some cases, among other possible benefits. In some embodiments, the piston 202 may be degeneratively doped. In some embodiments, the piston 202 is formed of SiP+.

Figure 2C:
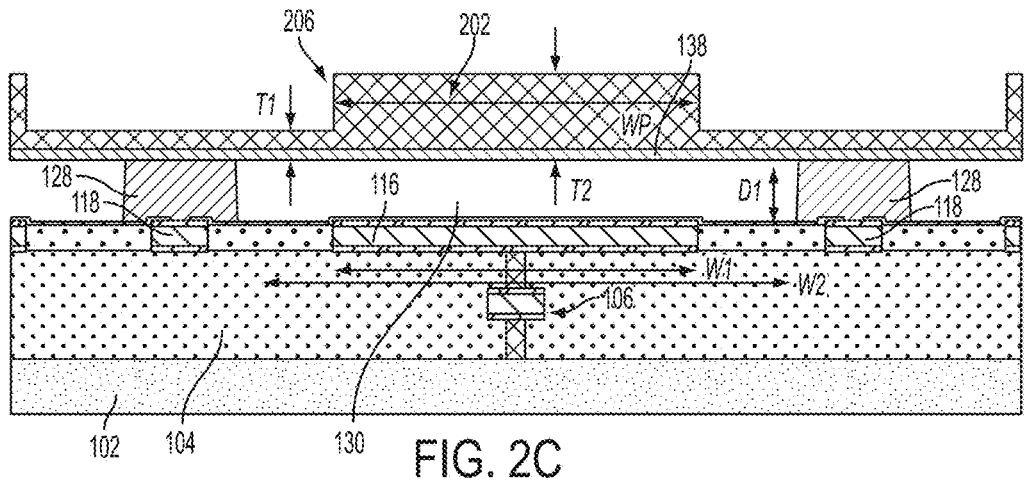

As shown in FIG. 2B, the transfer wafer 201 may be monolithically integrated with the CMOS wafer as a result of the bonding process. Subsequently, as shown in FIG. 2C, the base layer 132, insulating layer 134 and layer 204 may be removed by wafer grinding, then etching, and then removal of the buried oxide, or in any other suitable manner. The result may thus include the piston 202 overlying the cavity 130. The piston 202 and layer 138 may form a membrane as shown, and thus may be considered a piston membrane. The piston membrane may have a peripheral (or outer) portion with thickness T1 and a center portion with thickness T2. In some embodiments, T1 may be made as thin as possible, and may, for example, be between approximately 1 micron and approximately 10 microns. The piston 202 may have a width WP. In some embodiments, the width WP may be substantially the same as the width W1 of the electrode 116. However, not all embodiments are limited in this respect, as WP may be greater than W1 in some embodiments or less than W1 in some embodiments.

As non-limiting examples of dimensions, the cavity 130 illustrated in FIG. 2C may have any of the cavity dimensions previously described herein or any other suitable dimensions. For example, D1 and W2 may have any of the various previously described for those dimensions.

The thickness T1 may be any of the values previously described for T1 or any of the values described for TM Likewise, the thickness T2 may have any of the values previously described in connection with TM or any other suitable values. In some embodiments, the thickness T1 may be made as small as possible and the thickness T2 may assume any of the values previously described in connection with TM. For example, the thickness T2 may be between 1 micron and approximately 100 microns, between approximately 10 microns and approximately 50 microns, any value within such ranges, or any other suitable values.

Figure 3A:
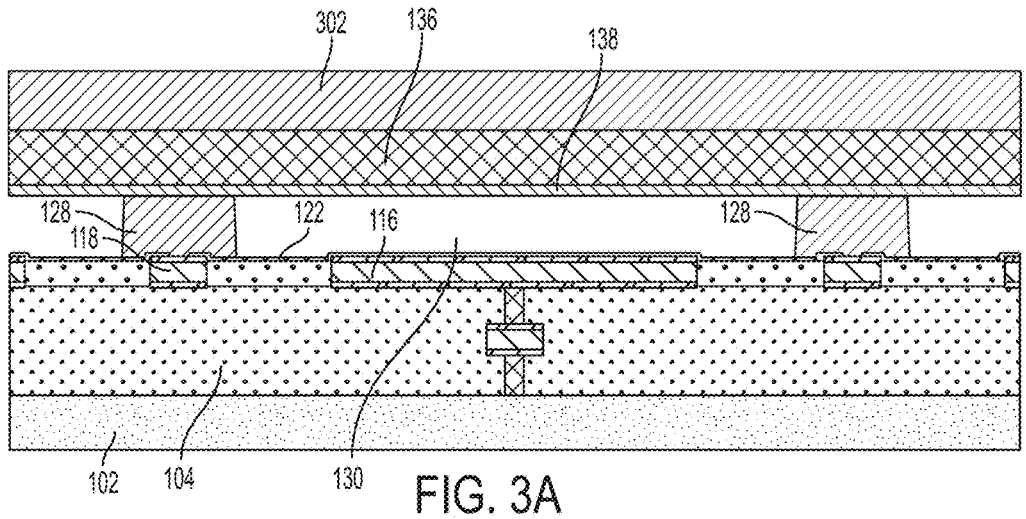
FIGS. 3A-3B illustrate a process sequence for forming an alternative CUT having a piston membrane, in which the piston membrane is formed after wafer bonding, according to a non-limiting embodiment of the present application.
Figure 3B:
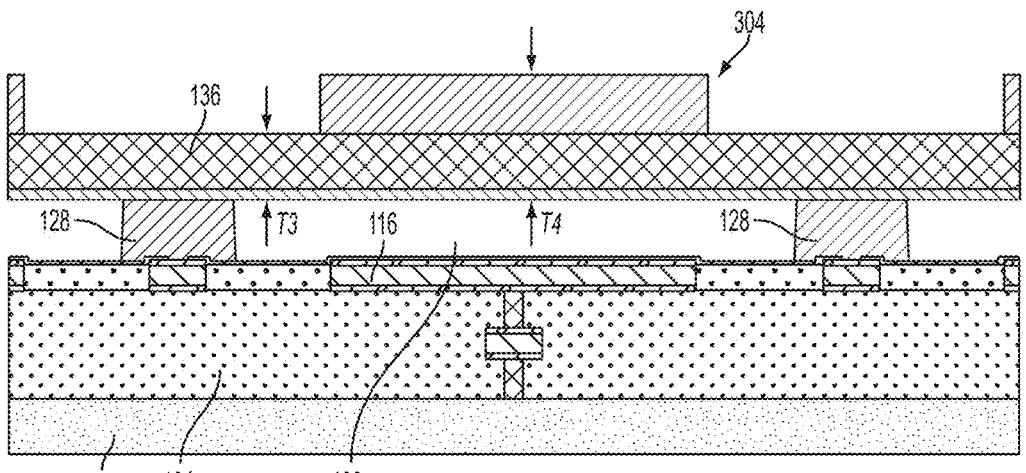

A non-limiting alternative process for forming a piston membrane overlying a cavity is illustrated in FIGS. 3A-3B, in which the thicker center portion of the piston is on a topside of the membrane. The process may begin with the structure of FIG. 1K, and from there add a passivation layer 302 as shown in FIG. 3A. The passivation layer may be silicon nitride ($Si_3N_4$) or other suitable passivation material which may be formed at temperatures sufficiently low to prevent damage to the CMOS wafer.

The passivation layer 302 may then be suitably etched as shown in FIG. 3B to create a center portion 304 for the piston membrane. It should be noted that in this embodiment the center portion 304 is formed of a different material than that of the layer 136.

The piston membrane of FIG. 3B may have an outer portion with thickness T3 and the center portion may have a thickness T4. The thickness T3 may be any of those values previously described in connection with T1, while T4 may be any of those values previously described in connection with T2.

Figure 4A:
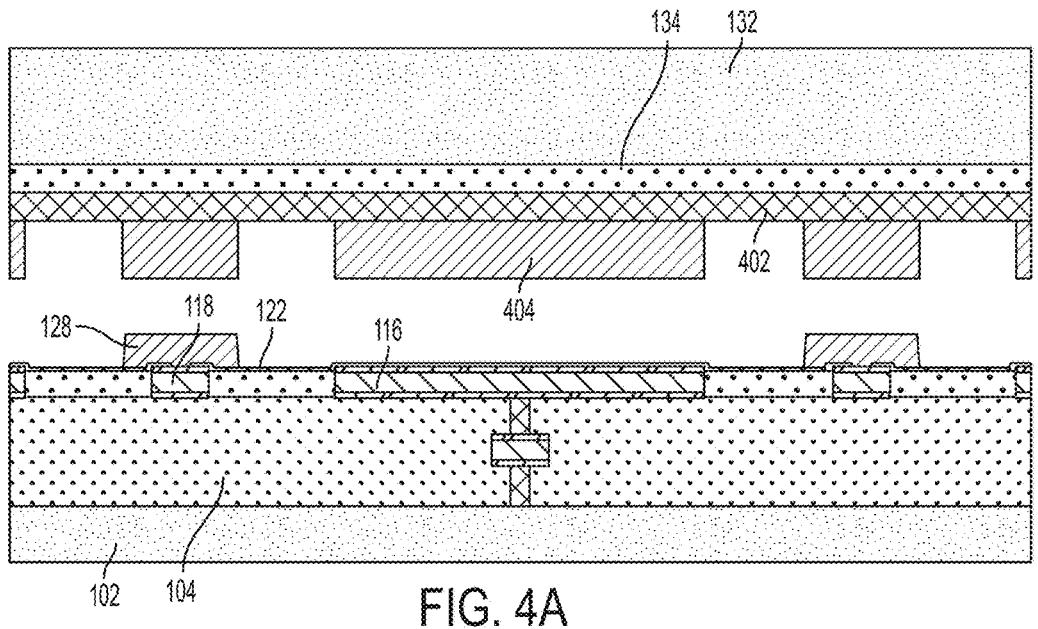
FIGS. 4A-4C illustrate an alternative process sequence for forming a CUT having a piston membrane, in which the piston membrane is transferred from a transfer wafer, according to a non-limiting embodiment of the present application.
Figure 4B:
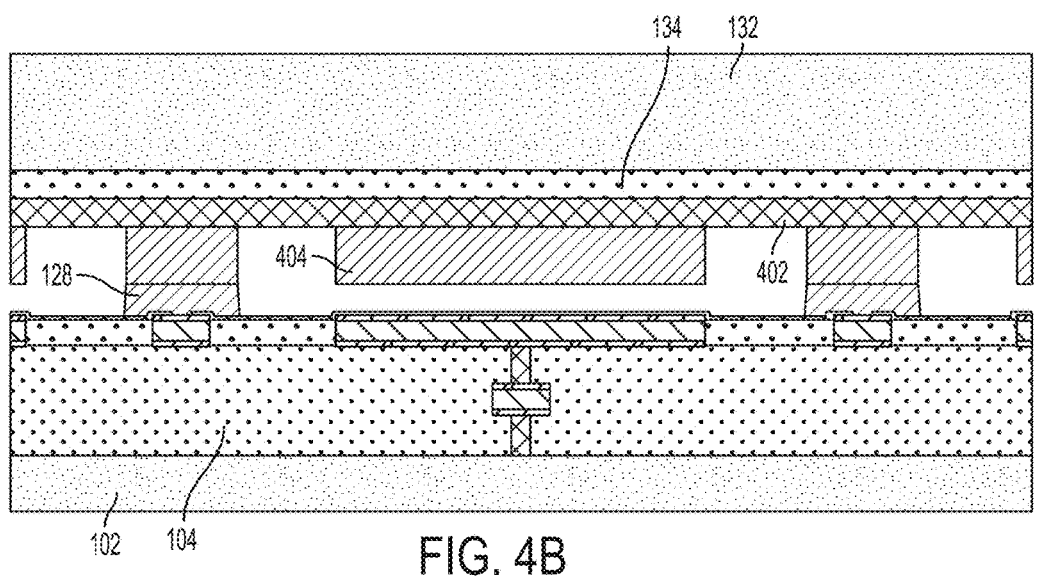
Figure 4C:
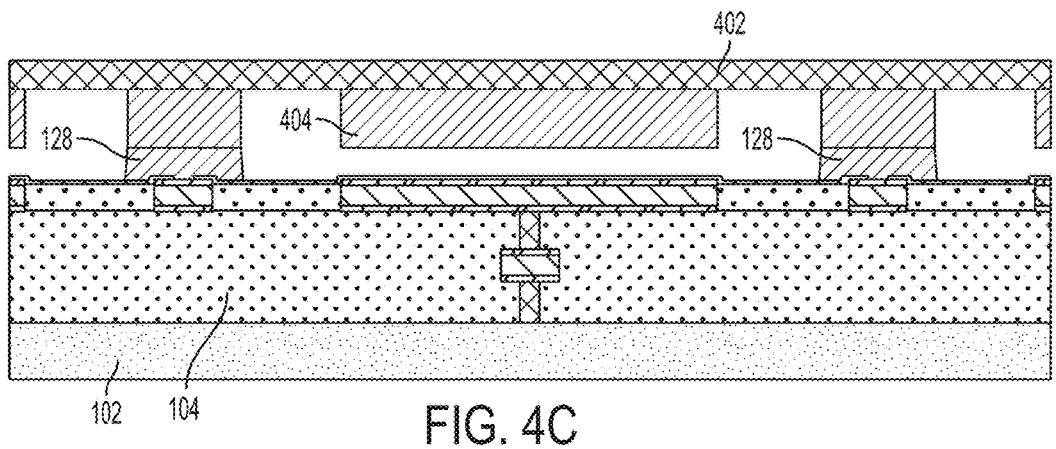

A further alternative process for forming a piston membrane is illustrated in FIGS. 4A-4C. The process may begin with a structure similar to, substantially the same as, or identical to that of FIG. 1H. However, the contacts 128 may have a smaller height in the embodiment of FIGS. 4A-4C. For example, whereas the contacts 128 in FIG. 1H may be the same height as the depth D1 of the cavity 130 in the embodiment represented by FIG. 1H, and therefore may have any of the values previously described herein for D1 (e.g., between 1 and 10 microns, less than 5 microns, etc.), the height of the contact 128 in FIG. 4A may be smaller (e.g., half the height of previously described D1, one-quarter the height of D1, etc.). A transfer wafer having the base layer 132, insulating layer 134, layer 402 (e.g., monocrystalline silicon, polysilicon, amorphous silicon, or SiP+ in some embodiments) and a patterned layer 404 may be bonded to the CMOS wafer using low temperature bonding. The patterned layer 404 may have a thickness between approximately 1 micron and approximately 10 microns, between approximately 3 microns and approximately 7 microns, any value within those ranges, less than 5 microns, less than 3 microns, or any other suitable value.

The patterned layer 404 may be formed of a material suitable for bonding to contacts 128, and in some embodiments may be formed of the same material as contacts 128. In an embodiment the patterned layer 404 may be formed of TiN.

As shown in FIG. 4C, the base layer 132 and insulating layer 134 may be removed subsequent to bonding of the transfer wafer with the CMOS wafer. Such removal may be performed using grinding, etching, and/or buried oxide removal, or other suitable techniques. In some embodiments, the layer 402 may be thinned to a desired membrane thickness. As shown, the resulting structure may include a piston with a thicker center portion formed on an underside of the membrane. In this configuration, electrical connectivity may be provided from the patterned layer 404 through the layer 402 to the cavity sidewalls since the materials making up those components may be electrically conductive.

It should be appreciated from the discussion of FIGS. 4A-4C that the illustrated CUT may be formed with only two wafers and a single wafer bonding process. The layer 402 may function as an etch stop in some embodiments, which may allow for formation of the piston membrane (the combination of 402 and 404) to be formed from a single transfer wafer. Thus, the process may be relatively simple and involve a relatively small number of processing steps compared to if three or more wafers and multiple wafer bonding steps were used to form the piston membrane.

Another structure which may be formed as part of an ultrasonic transducer according to an aspect of the present application is a membrane stop, which in some embodiments may function as an isolation post and which may provide various benefits. Membrane stops may effectively alter the depth of a cavity such that a membrane may contact the bottom of the cavity (referred to as collapse) more easily, and may alter the frequency behavior of an ultrasonic transducer. Namely, when the membrane is pulled down far enough, it makes contact with the bottom of the cavity. Such operation may be advantageous since having the membrane hit or contact the bottom of the cavity can dampen certain resonant modes, thereby broadening the frequency response of the transducer. However, there is a "charge trapping" effect, in which charge may end up deposited on the electrodes of the transducer, thereby altering the operating characteristics of the transducer (e.g., increasing the necessary bias voltage), and causing hysteresis. Membrane stops may provide the benefit of "bottoming out" the membrane, while substantially reducing the charge trapping effect and problems with hysteresis. Ultrasonic transducers with membrane stops may be more reliable after collapse than ultrasonic devices lacking such membrane stops. Moreover, because the membrane stop may prevent the membrane from contacting the bottom-most part of the cavity, insulation need not be formed on the bottom surface of the cavity in all embodiments, which can therefore reduce processing steps and time in fabricating an ultrasonic transducer. However, the insulator on the bottom surface of the cavity may be used in case of unanticipated contact between the membrane and the bottom of the cavity (despite any membrane stop) and/or to prevent electrical discharge across the cavity.

Membrane stops may be formed in different locations of an ultrasonic transducer. For example, membrane stops may be formed on the bottom of a cavity of an ultrasonic transducer. In some embodiments, membrane stops may be formed on the bottom of a membrane of the ultrasonic transducer (e.g., on the bottom side of a membrane transferred from a transfer wafer). In other embodiments, membrane stops may be formed on both the bottom of a cavity and the bottom of a membrane of an ultrasonic transducer. Non-limiting examples are now described.

Figure 5:
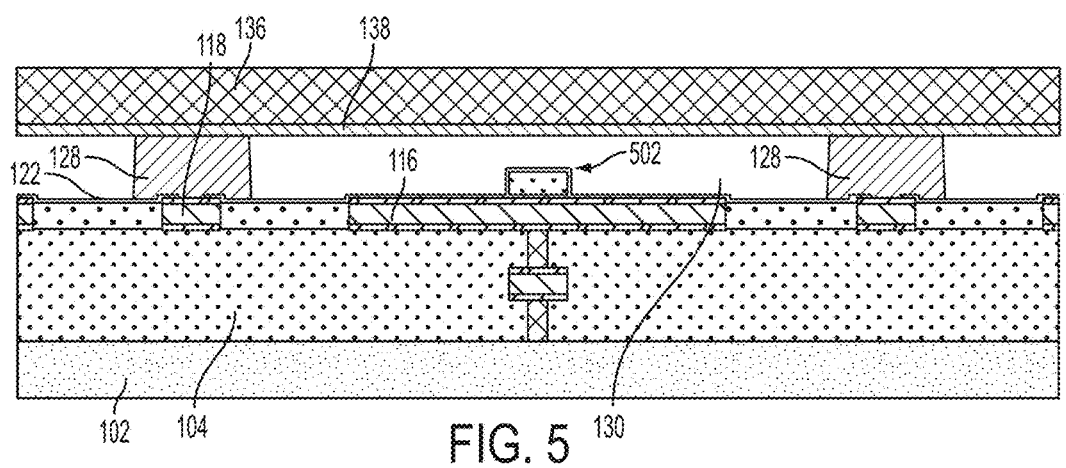
FIG. 5 illustrates a CUT having a membrane stop disposed on a bottom surface of a cavity of the CUT, according to a non-limiting embodiment of the present application.

FIG. 5 illustrates an alternative ultrasonic transducer to that of FIG. 1K. As shown, the ultrasonic transducer includes the structure of FIG. 1K with the addition of a membrane stop 502 formed on the bottom of the cavity 130.

The membrane stop 502 may be formed between the stages of FIGS. 1D of 1E. Namely, subsequent to step 1D the membrane stop may be deposited and patterned on electrode 116. The processing steps of FIGS. 1E-1K may then be performed to arrive at the structure of FIG. 5.

Figure 6:
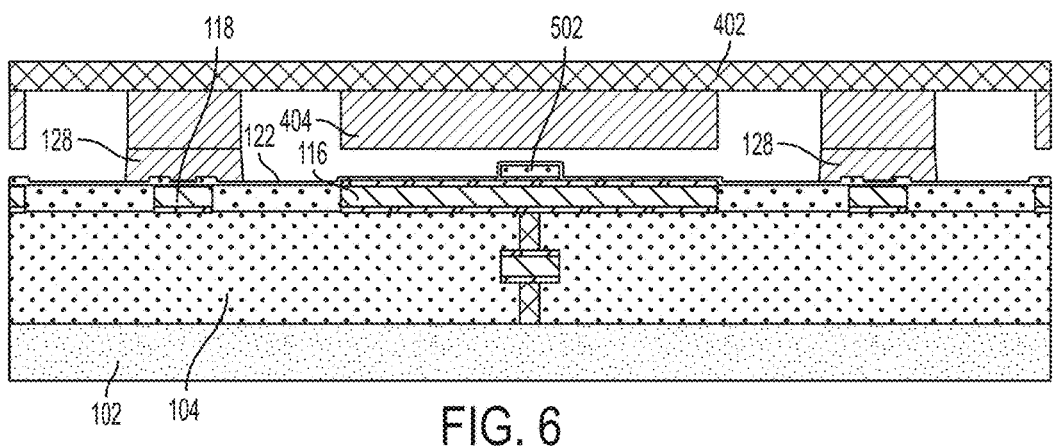
FIG. 6 illustrates a CUT having a piston membrane and a membrane stop disposed on a bottom portion of the cavity of the CUT, according to a non-limiting embodiment of the present application.

According to an aspect of the present application, an ultrasonic transducer may have a piston membrane and one or more membrane stops. A non-limiting example is illustrated in connection with FIG. 6, which combines features of previously described FIGS. 4C and 5.

FIGS. 1A-1K illustrate one non-limiting example of an embedded electrical contact making connection to a bottom side of a membrane of an ultrasonic transducer. In that non-limiting example, the conductive contact also is a sidewall of the cavity of the ultrasonic transducer, meaning that the ultrasonic transducer had conductive sidewalls. An alternative configuration for making direct electrical contact from a CMOS wafer to an underside of membrane of an ultrasonic transducer is to use an embedded via. FIGS. 7A-7H illustrate a non-limiting example.

Figure 7A:
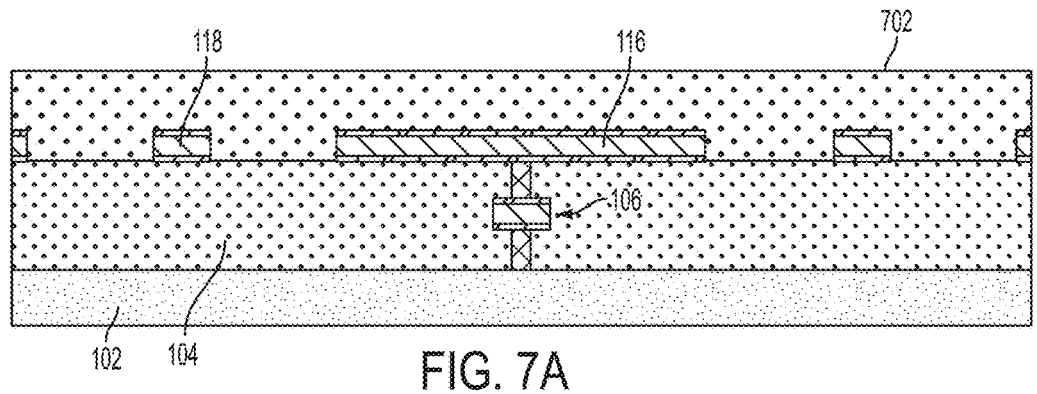
FIGS. 7A-7H illustrate a process sequence for forming a CUT having a via embedded in a CMOS wafer to make electrical contact to a bottom side of a membrane of the CUT, according to a non-limiting embodiment of the present application.

The processing stages of FIGS. 1A-1C may be performed. Then, as shown in FIG. 7A, an insulating layer 702 may be deposited, for example using high density plasma deposition. The insulating layer 702 may be $SiO_2$ or any other suitable insulator. The insulating layer may be planarized, for example by CMP.

Figure 7B:
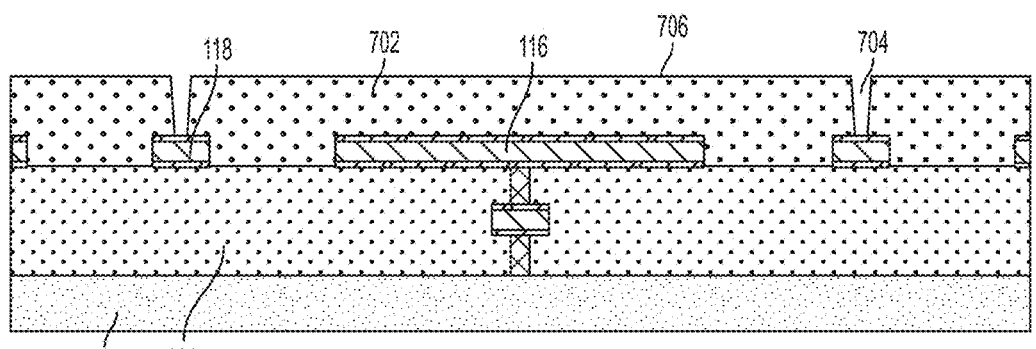

As shown in FIG. 7B one or more vias 704 may be etched, for example to land on second metallization layer 108, which may function as an etch stop. Optionally, a relatively thin layer of liner material (e.g., TiN) 706 may be deposited conformally, thus covering the vias 704 and the top surface of the CMOS wafer.

Figure 7C:
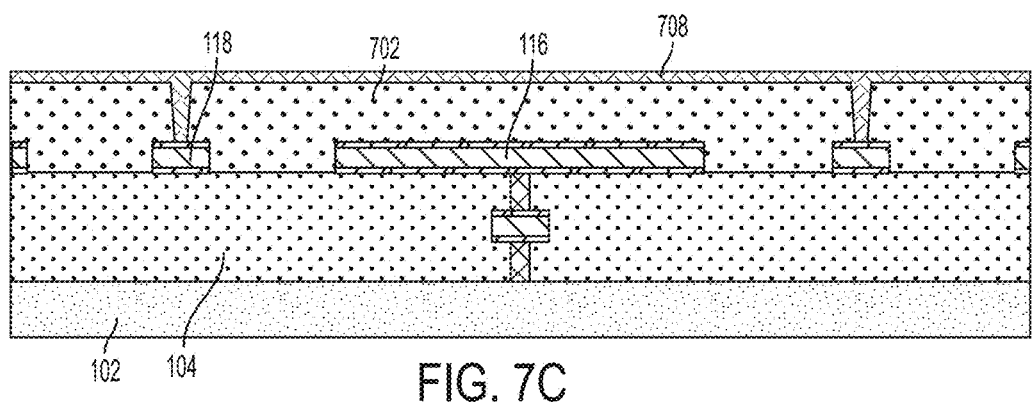
Figure 7D:
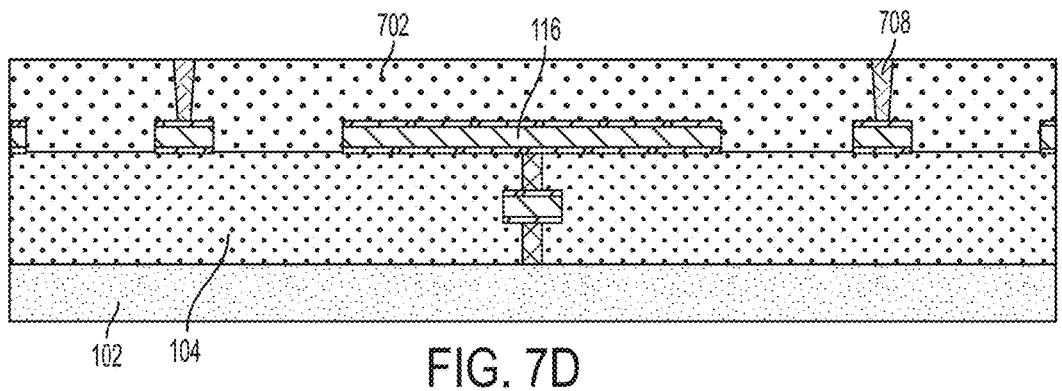

As shown in FIG. 7C, the vias may then be filled with conductive plugs 708, for example by depositing a layer of conductive material such as Tungsten (W). As shown in FIG. 7D, the conductive layer may be etched back.

Figure 7E:
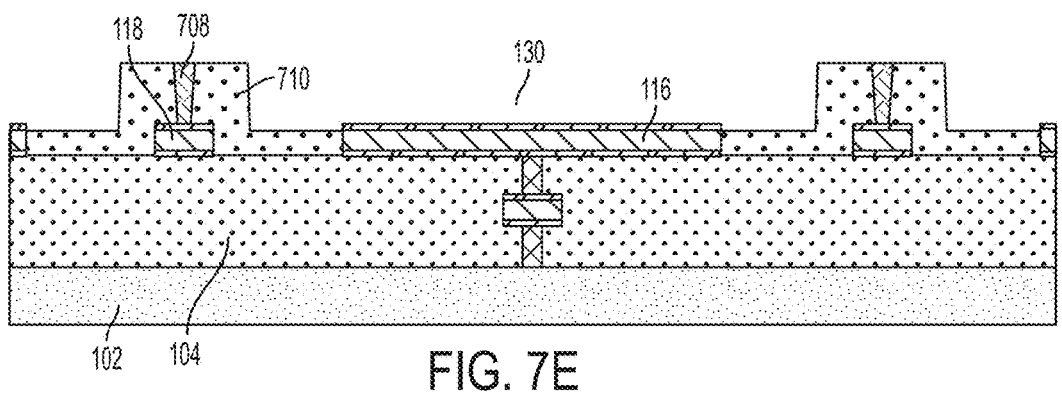

In FIG. 7E, the cavity 130 may then be etched from the insulating layer 702, leaving sidewalls 710 having conductive plugs (i.e., conductive plugs 708) embedded therein.

Figure 7F:
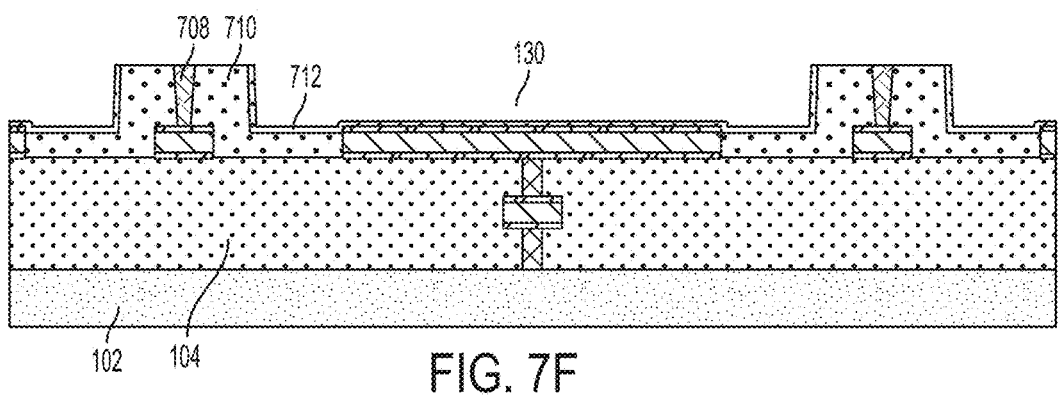

In FIG. 7F, the upper surface of the CMOS waver may be covered with an insulating layer 712, which may subsequently be removed from the tops of the sidewalls 710 in preparation for wafer bonding.

Figure 7G:
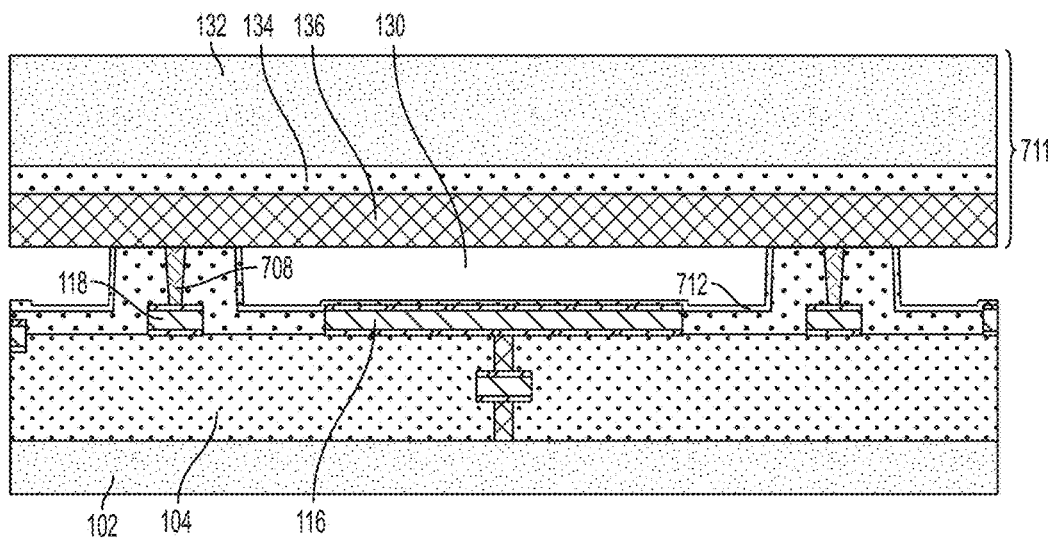
Figure 7H:
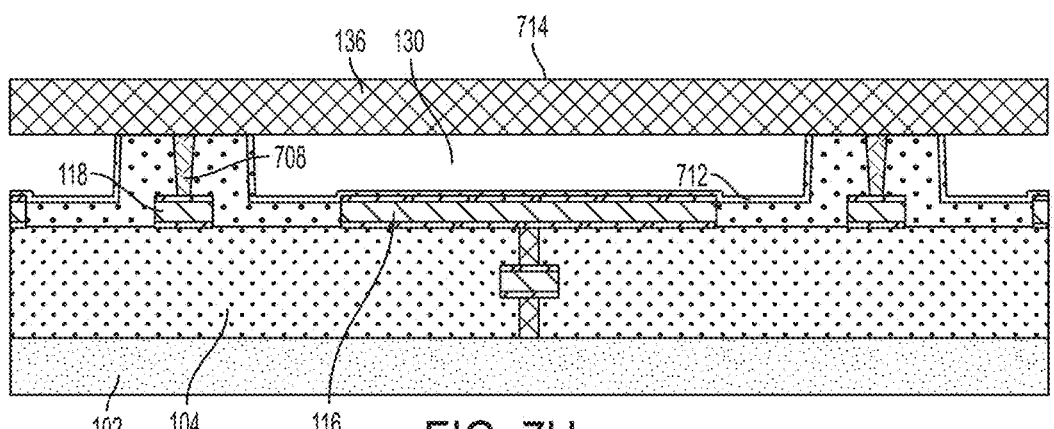

In FIG. 7G, a transfer wafer 711, which may be similar to or the same as the transfer wafer of FIG. 1I but lacking the layer 138, may be wafer bonded with the CMOS wafer. As shown in FIG. 7H, the base layer 132 and insulating layer 134 may then be removed by suitable techniques, thus leaving the membrane 714.

It should be appreciated that the bonding illustrated in FIG. 7G causes the plugs 708 to be in direct contact with the layer 136 on the top of the plugs, i.e., no liner may be formed between the plug 708 and the layer 136 at the point of intersection. In some embodiments, the layer 136 may be silicon (e.g., monocrystalline, polycrystalline, or amorphous). While conventional processing techniques attempt to avoid such a direct connection between a plug formed of, for example, Tungsten, Applicants have appreciated that such direct connection may be acceptable in scenarios in which the direct connection is between the plug and a layer (e.g., layer 136) not being used to support high quality integrated circuits. Rather, because the layer 136 is being used to form a membrane, diffusion of the material from plug 708 into the layer 136 may be acceptable in some embodiments.

Figure 8A:
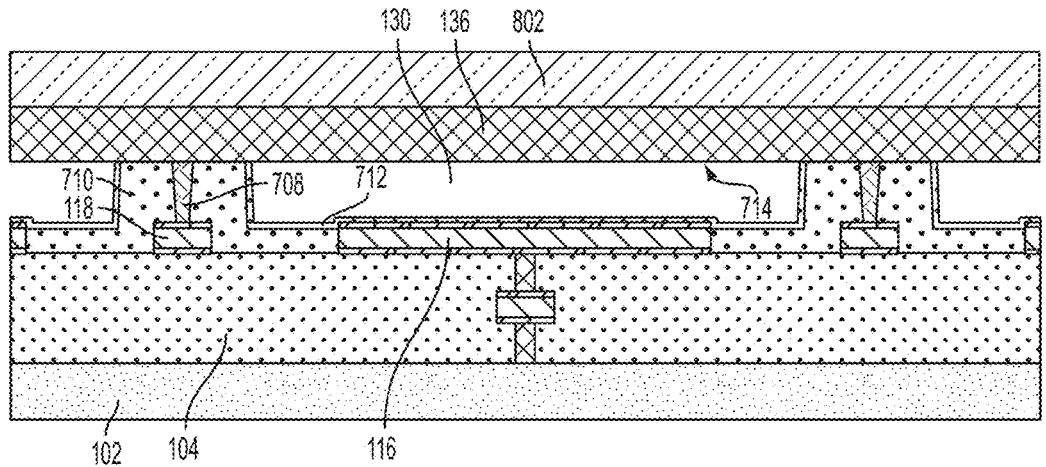
FIGS. 8A-8B illustrate a process sequence for forming a piston membrane from the device resulting from the process of FIGS. 7A-7H, according to a non-limiting embodiment of the present application.
Figure 8B:
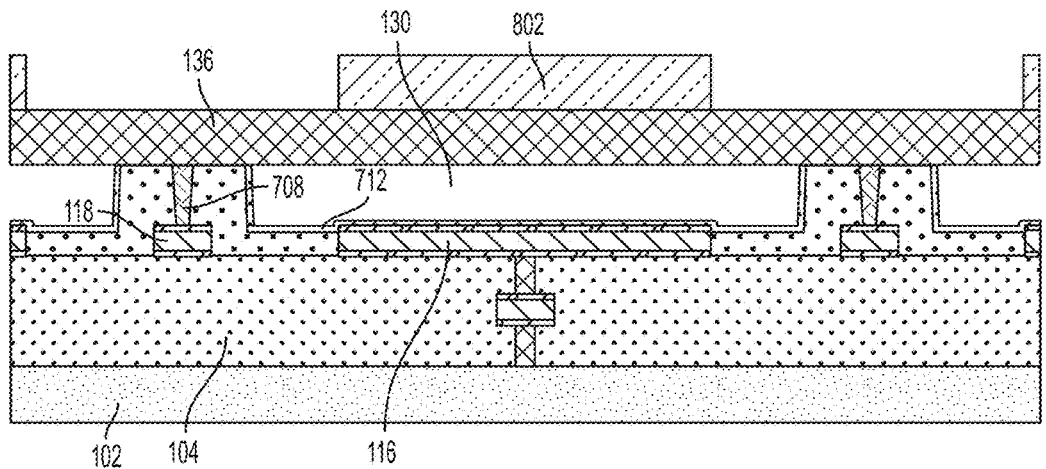

FIGS. 8A-8B illustrate a method for forming a piston from the structure of FIG. 7H. Namely, a passivation layer 802 of $Si_3N_4$ or any other suitable passivation material, may be deposited on the membrane 714. Then, as shown in FIG. 8B, the passivation layer 802 may be suitably patterned.

Figure 9A:
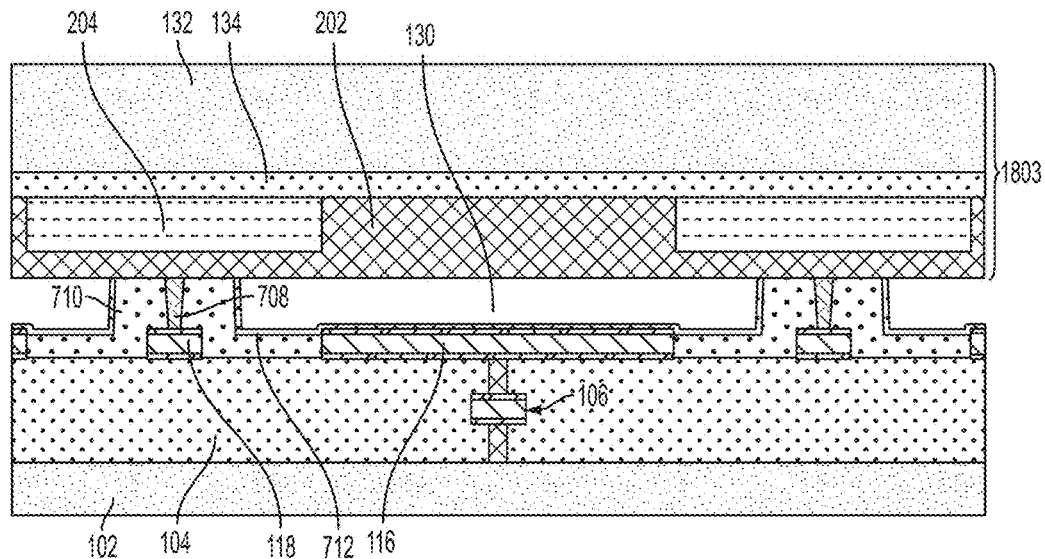
FIGS. 9A-9B illustrate a process sequence for forming a CUT having a piston membrane transferred from a transfer wafer and having an embedded via in a CMOS wafer to make electrical contact to the bottom side of the membrane, according to a non-limiting embodiment of the present application.
Figure 9B:
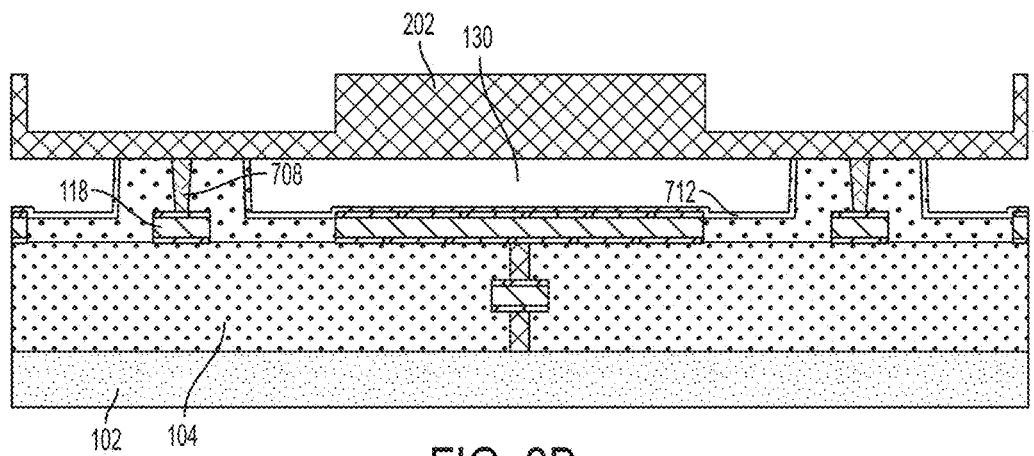

FIGS. 9A-9B illustrate an alternative manner of forming a piston membrane over a cavity in a CMOS wafer where the cavity is bounded by non-conductive sidewalls having an embedded via therein. As shown in FIG. 9A, the structure of FIG. 7F may be bonded with a transfer wafer 1803 similar to the type previously described in connection with FIG. 2B minus the layer 138. The base layer 132, insulating layer 134 and layer 204 may be removed as previously described in connection with FIG. 2C.

Some embodiments of the present application provide practical methods for fabricating membranes above cavities in a CMOS wafer and having an embedded via which makes contact to a top side of the membrane. FIGS. 10A-10H illustrate an example.

Figure 10A:
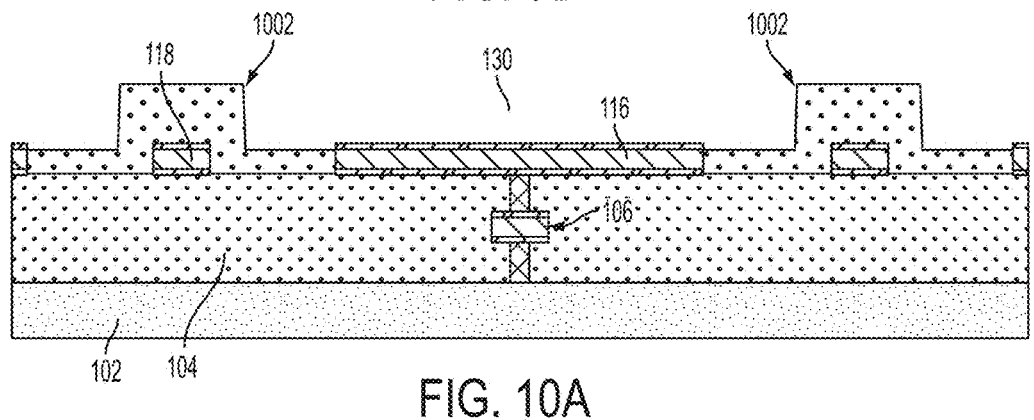
FIGS. 10A-10H illustrate a process sequence for forming a CUT having a piston membrane and an embedded via through the membrane to make electrical contact to a CMOS wafer, according to a non-limiting embodiment of the present application.
Figure 10B:
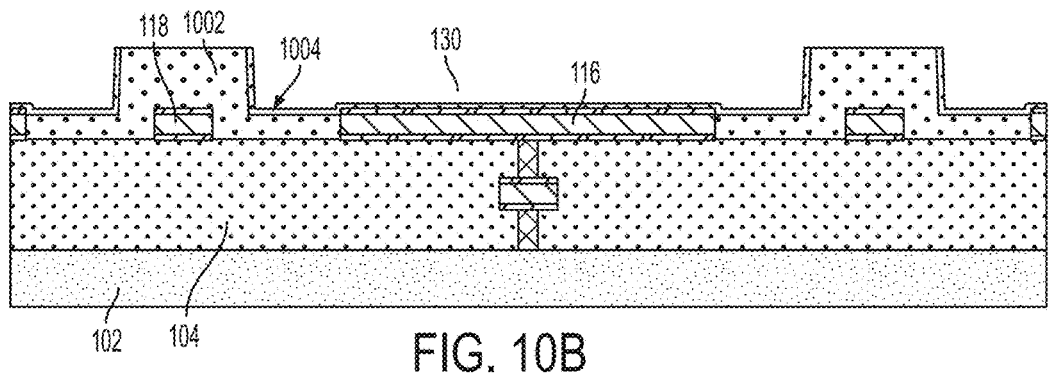

Beginning with the structure of FIG. 7A, the insulating layer 702 may be patterned as shown in FIG. 10A to form sidewalls 1002 at least partially defining the cavity 130. In FIG. 10B, an insulator (e.g., $SiO_2$) 1004 may be deposited and then CMP performed to prepare the topside of the sidewalls 1002 for bonding with another wafer.

Figure 10C:
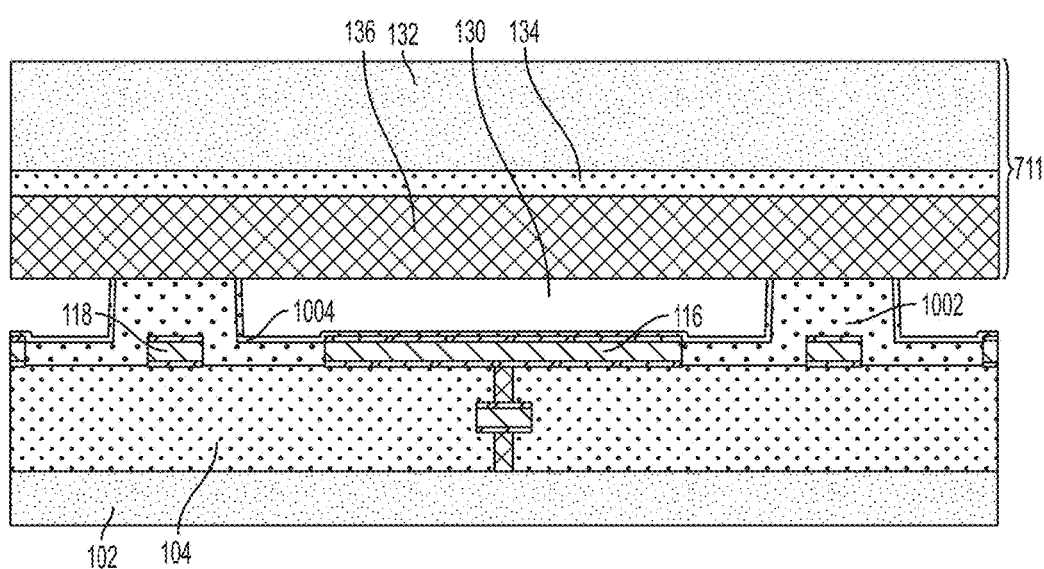

As shown in FIG. 10C, wafer bonding may then be performed with the CMOS wafer and a second wafer (e.g., a transfer wafer). The transfer wafer may be the same type as that previously described in connection with FIG. 7G, though other types of transfer wafers are also possible. The bonding process may be a low temperature (e.g., below 450° C.) direct bonding process, which may preserve any silicon circuitry (e.g., ICs) on the CMOS wafer.

Figure 10D:
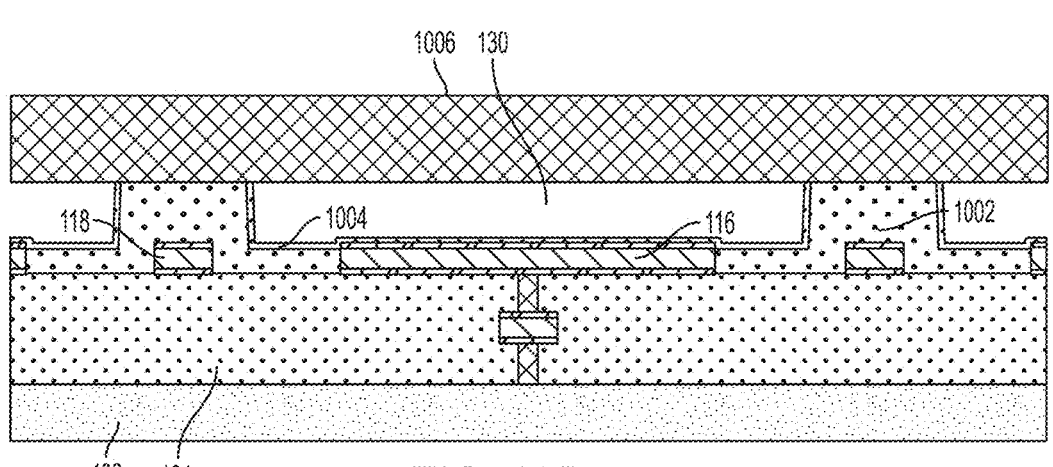

As shown in FIG. 10D, the base layer 132 and insulating layer 134 may be removed, for example using any of the techniques previously described for such removal. Thus, a membrane 1006 may be monolithically integrated with the CMOS wafer and overlying the cavity 130.

Figure 10E:
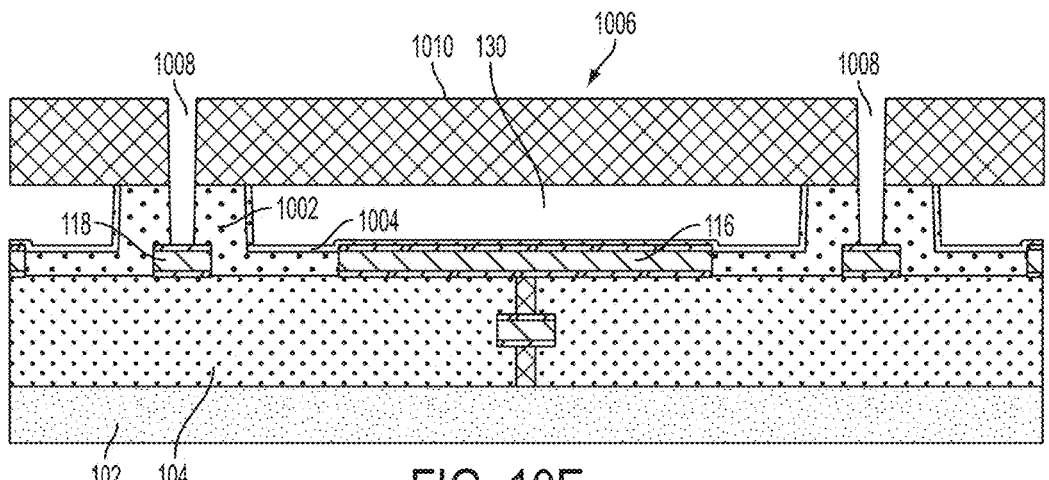

As shown in FIG. 10E, vias 1008 may be formed through the membrane 1006 and sidewalls 1002, stopping on the contacts 118. The etch may be a selective etch, and may be directional, such as a deep reactive ion etch (DRIE), or any other suitable etch. A liner 1010 may then be formed in the vias and on the top side of the membrane 1006. The liner may be conductive, may be a metal, and in some embodiments is TiN, though other materials may alternatively be used.

Figure 10F:
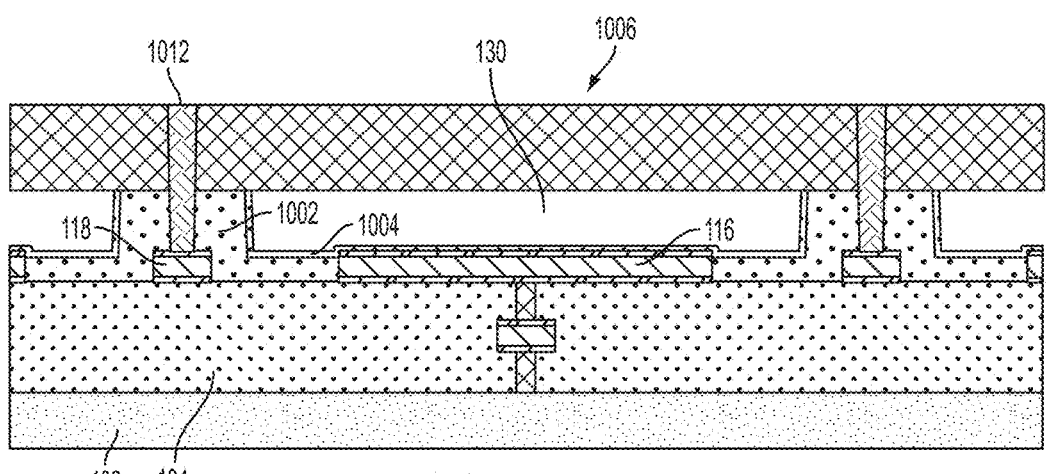

As shown in FIG. 10F, plugs 1012 may then be formed in the vias 1008 by suitable deposition and etch back. For example, the plugs 1012 may be formed of tungsten, and may be formed by depositing tungsten to fill the vias 1008 and then etching the tungsten back using the liner 1010 (e.g., TiN) as an etch stop.

Subsequently, in FIG. 10G, layers 1014 and 1016 may be deposited on the top side of the membrane 1006. The layers may include a passivation layer. For example, layer 1014 may be $SiO_2$ or any other suitable passivation layer. Layer 1016 may also be a passivation layer, and in some embodiments be $Si_3N_4$.

Figure 10G:
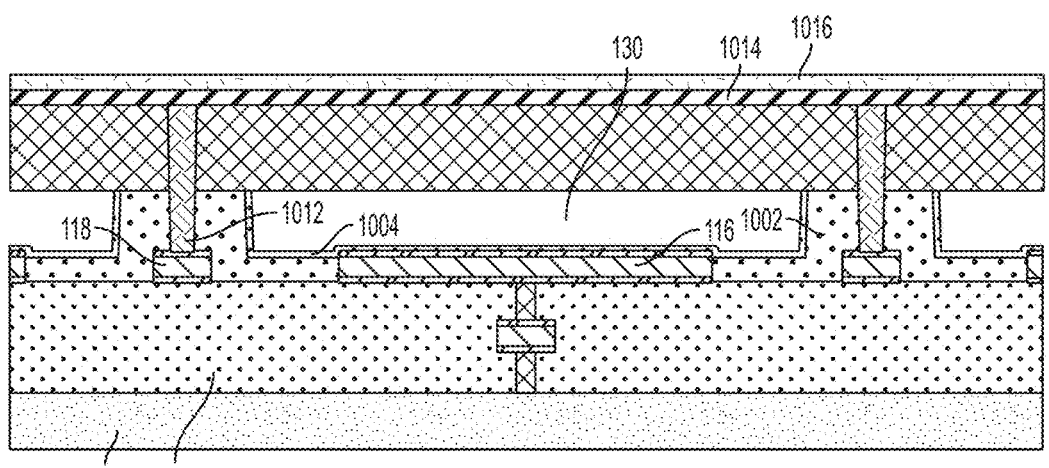

Thus, FIG. 10G illustrates a configuration of an ultrasonic transducer providing electrical contact through a membrane (and therefore on a top side of the membrane) monolithically integrated with a CMOS wafer, where the contact includes a conductive path formed at least in part by a via embedded in a sidewall of a cavity of the CMOS wafer. Optionally, as shown in FIG. 10H, the layers 1014 and 1016 may be patterned to define a piston membrane 1018.

Figure 10H:
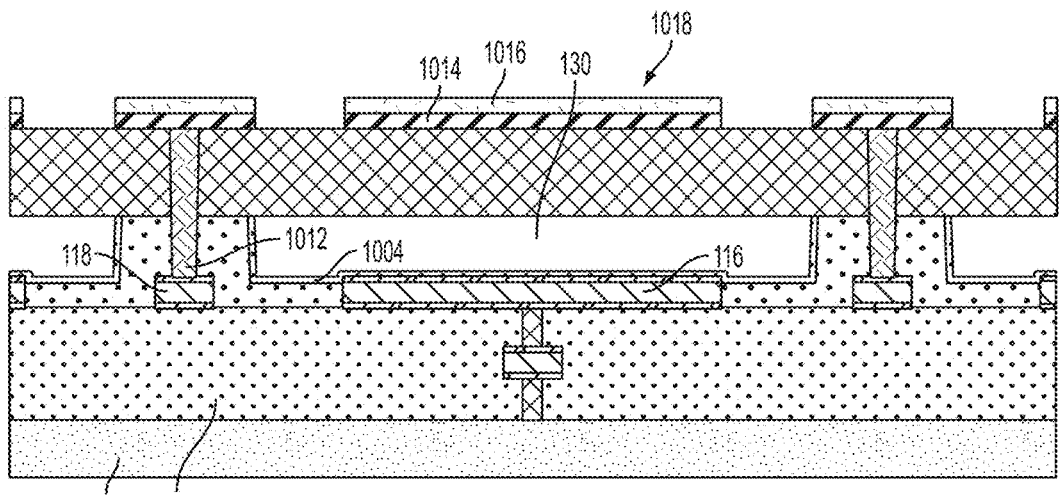
Figure 11:
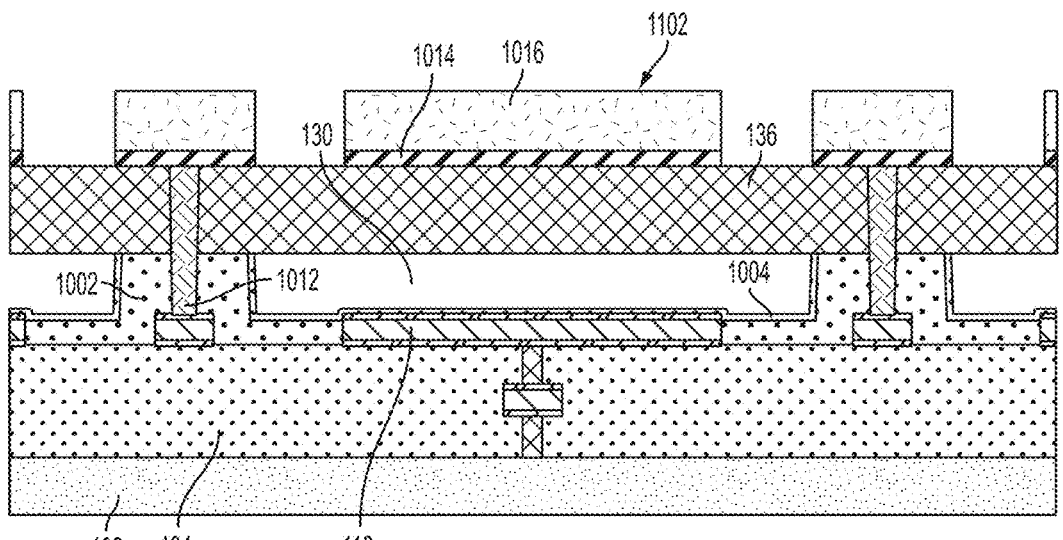
FIG. 11 illustrates an alternative CUT to that resulting from the process of FIGS. 10A-10H that includes a piston membrane having a thicker center portion than that of the CUT in FIG. 10H.

The piston membrane 1018 of FIG. 10H is a non-limiting example of a piston membrane that may be formed using the processing steps of FIGS. 10A-10G. The piston membrane may have an outer portion (proximate where the membrane contacts the sidewalls 1002) with a thickness assuming any of the values previously described herein for T1 and a center portion having a thickness assuming any of the values previously described herein for T2. As an example, the center portion may have a thickness less than 50 microns. As an alternative, it may be desirable in some embodiments for the piston to be thicker than that shown in FIG. 10H. FIG. 11 illustrates a non-limiting example.

As shown, the piston membrane 1102 of FIG. 11 may be thicker than the piston membrane 1018 of FIG. 10H (e.g., 1.5 times as thick, twice as thick, three times as thick, or any other suitable thickness), though the rest of the ultrasonic transducer may be substantially the same as that illustrated in FIG. 10H. Such a configuration may be achieved by forming the layer 1016 with a greater thickness in the embodiment of FIG. 11 than in the embodiment of FIG. 10G.

Figure 12:
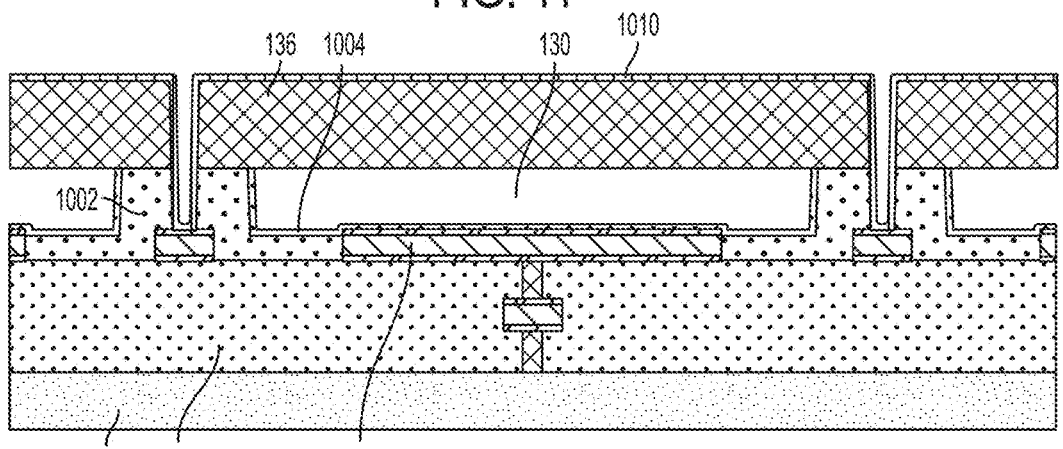
FIG. 12 illustrates a CUT having a lined via to make electrical contact between a CMOS wafer and a top side of a membrane of the CUT, according to a non-limiting embodiment of the present application.

As a further alternative configuration for making electrical contact from a metallization layer of CMOS wafer to the top side of a membrane, FIG. 12 illustrates an embodiment corresponding substantially to the structure of FIG. 10E. However, in the embodiment of FIG. 12 the liner 1010 may be thicker than that of the embodiment of FIG. 10E. For example, the liner 1010 may be less than 1 micron in the embodiment of FIG. 10E but may be between approximately 2 and 3 microns in the embodiments of FIG. 12. The liner 1010 in FIG. 12 may then serve as the primary electrical contact, without any conductive plug being formed in the vias. Such a configuration may simplify processing of an ultrasonic transducer by avoiding further processing steps associated with forming plugs in the vias.

In some embodiments, CUTs having top side electrical contacts but no embedded electrical contacts are provided. Aspects of the present application provide practical, cost-effective manners of fabricating several different designs of such CUTs. Some non-limiting examples are now described.

Figure 13A:
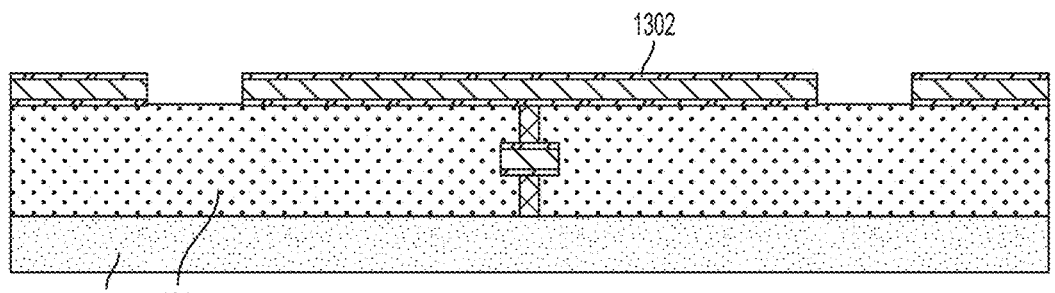
FIGS. 13A-13I illustrate a process sequence for forming a CUT having electrical contacts on a top side of a membrane of the CUT, according to a non-limiting embodiment of the present application.

FIGS. 13A-13I illustrate a first non-limiting embodiment of a process for fabricating a CUT having a top side electrical contact. Starting from the structure of FIG. 1A, the second metallization layer 108 may be patterned as shown in FIG. 13A to form an electrode 1302.

Figure 13B:
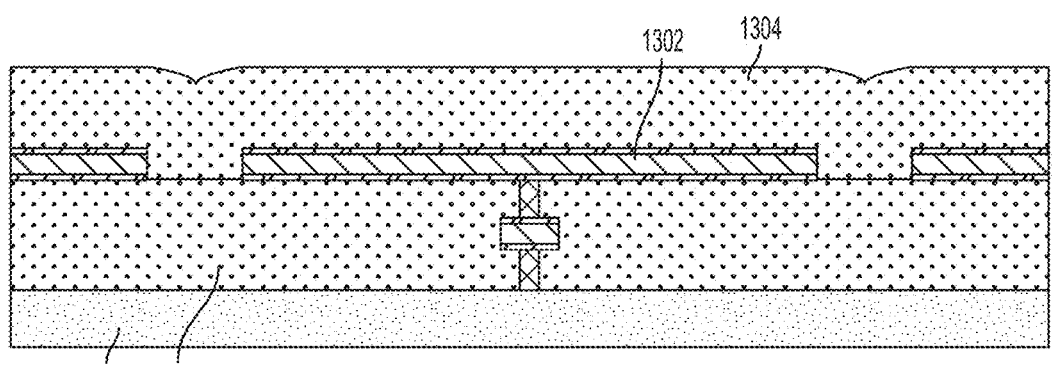

As shown in FIG. 13B, an insulating layer 1304 may then be deposited. The insulating layer may be SiO$_2$ in some embodiments, for example formed by TEOS or other suitable deposition technique.

Figure 13C:
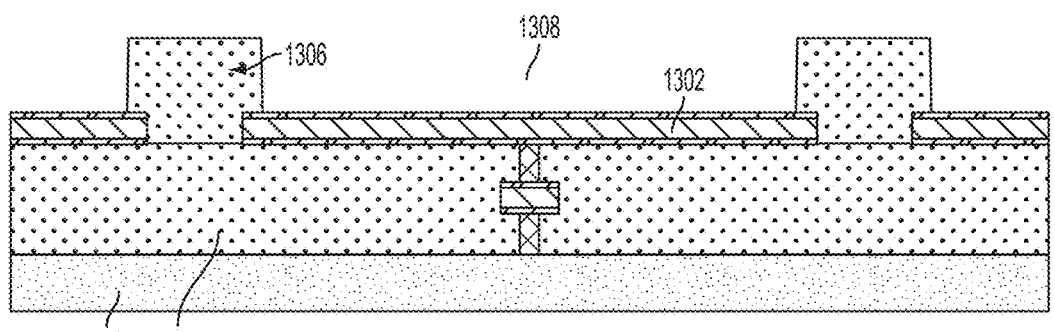

As shown in FIG. 13C, the insulating layer 1304 may be etched to form a cavity 1308 having sidewalls or spacers 1306 at least partially defining the cavity. Any suitable etch of the insulating layer may be performed. In some embodiments, the etch may be a selective etch and the second metallization layer 108 may function as an etch stop. For example, the second metallization layer 108 may include TiN (e.g., a TiN liner on an upper surface) which may function as an etch stop.

Figure 13D:
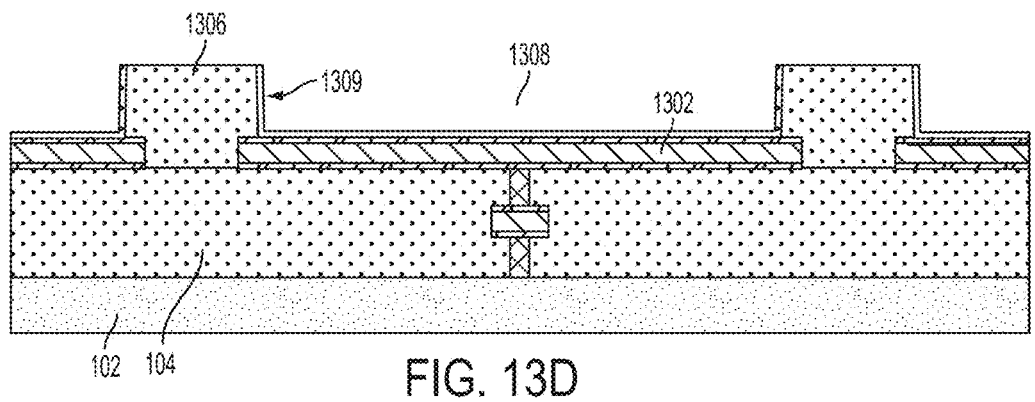

As shown in FIG. 13D, an insulating layer 1309 (e.g., SiO$_2$) may then be deposited. The CMOS wafer may be planarized (e.g., using CMP) and prepared for wafer bonding by performing surface treatment. Thus the insulating layer 1309 may be removed from the top of the sidewalls 1306.

Figure 13E:
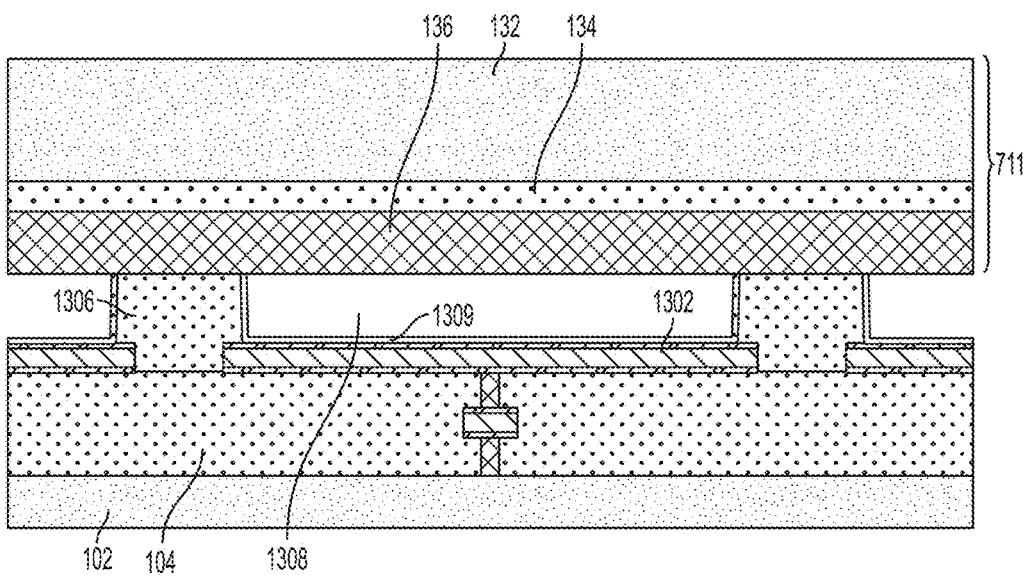
Figure 13F:
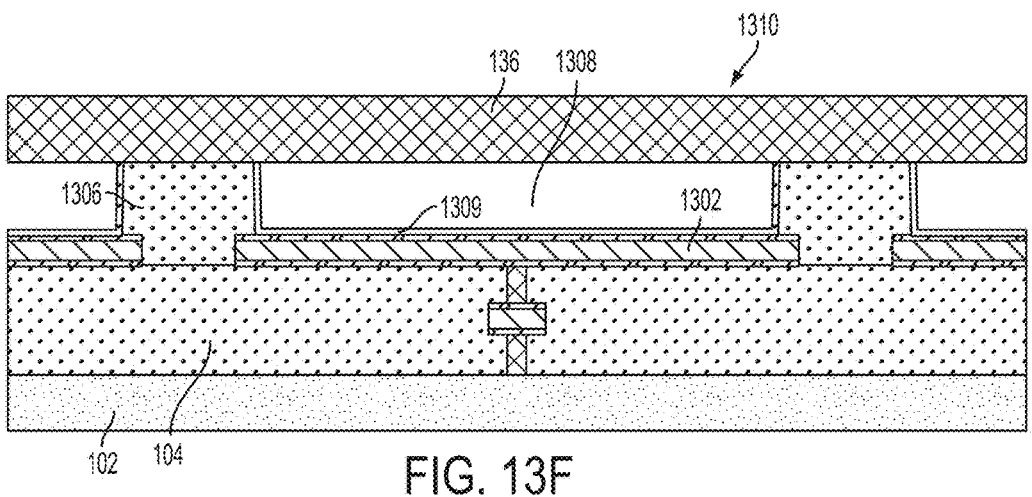

Wafer bonding may then be performed in FIG. 13E using a transfer wafer of the type previously described in FIG. 10C, or any other suitable wafer. The base layer 132 and insulating layer 134 of the transfer wafer may then be removed in the previously described manners as shown in FIG. 13F, leaving a membrane 1310 sealing the cavity 1308. It should be appreciated that in this embodiment the electrode 1302 is wider than the cavity 1308. For example, the cavity may have a width assuming any of those values previously described herein for W2, and the electrode 1302 may be 2 microns greater than that width, five microns greater than that width, 10 microns greater than that width, between 1 and 15 microns greater than that width, or any other suitable value.

Figure 13G:
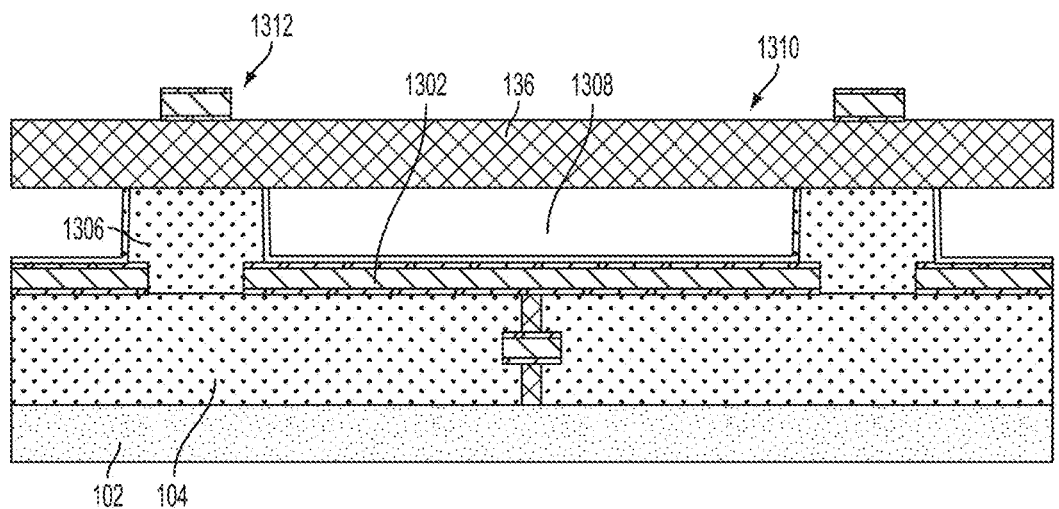

As shown in FIG. 13G, contacts 1312 may be formed on the top side of the membrane 1310. The contacts may have any suitable structure. In some embodiments, the contacts may be formed by forming a metallization layer on the top side of the membrane and then patterning the metallization layer to arrive at the illustrated structure. The metallization layer may include a multi-layer structure, for example having the three layer structure previously described in connection with second metallization layer 108 or any other suitable structure. Thus, as a non-limiting example, the contacts 1312 may include a layer of aluminum sandwiched between upper and lower TiN layers, though other configurations are possible.

Figure 13H:
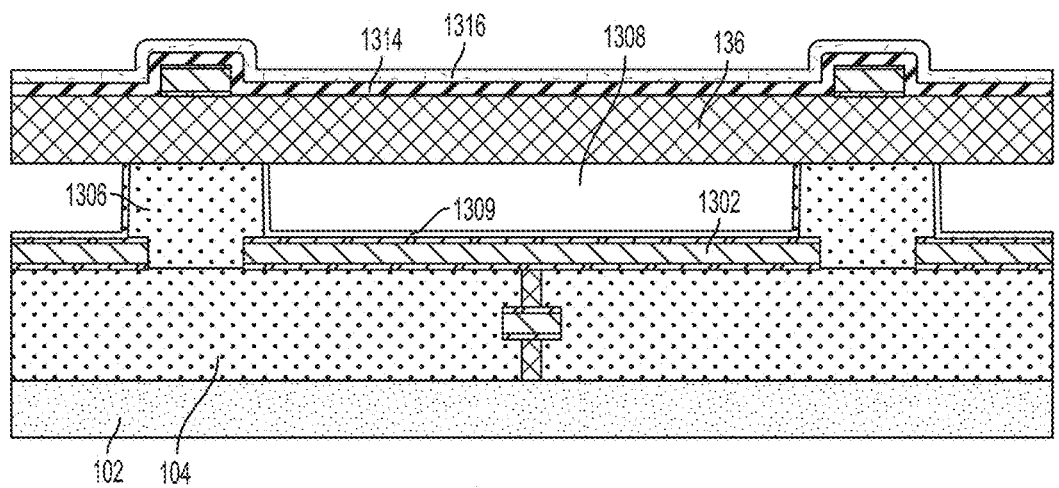

As shown in FIG. 13H, a passivation step may then be performed, for example by depositing layers 1314 and 1316. Layer 1314 may be an insulating layer, for example being formed of SiO$_2$. Layer 1316 may be formed of Si$_3$N$_4$ or any other suitable material.

Figure 13I:
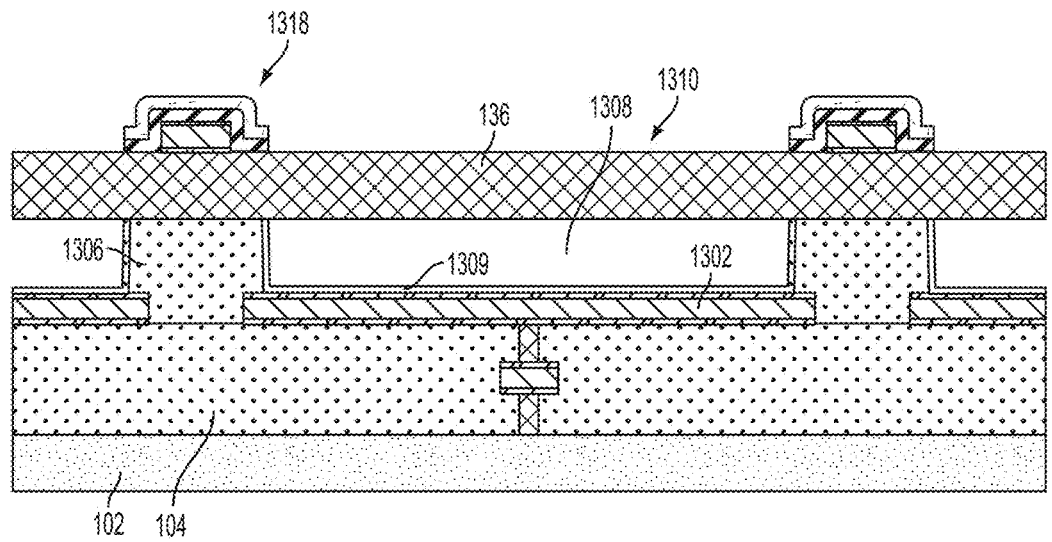

As shown in FIG. 13I, the layers 1314 and 1316 may then be patterned to form passivated contacts 1318 on the top side of the membrane 1310.

Figure 14:
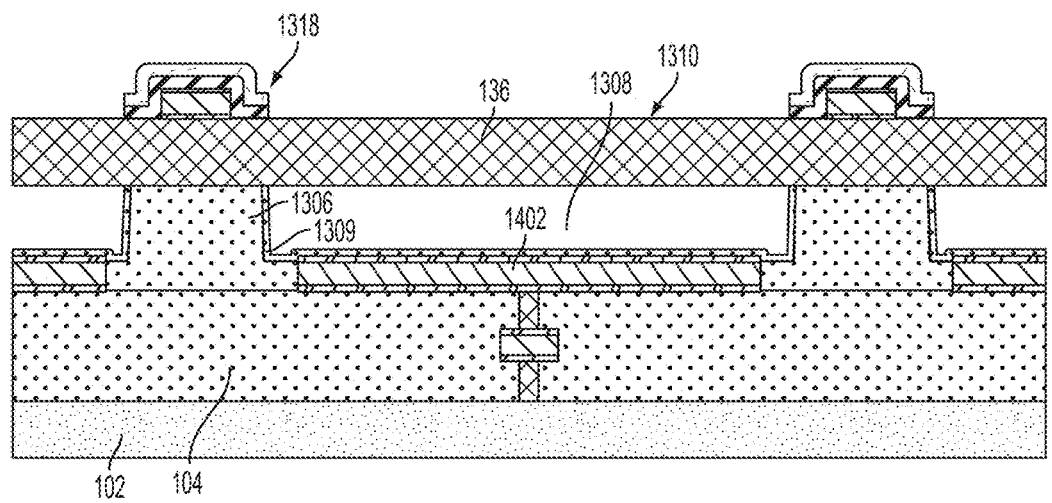
FIG. 14 illustrates an alternative CUT to that resulting from the process of FIGS. 13A-13I that includes an electrode beneath a cavity of the CUT that is narrower than a width of the cavity, according to a non-limiting embodiment of the present application.

FIG. 14 illustrates an alternative CUT to that of FIG. 13I. While similar to the CUT of FIG. 13I, the CUT of FIG. 14 has a bottom electrode 1402 that is not as wide as the cavity 1308, which may reduce capacitance with the cavity sidewalls. For example, the cavity 1308 may have a width assuming any of the values previously described herein for W2 and the electrode 1402 may have a width three-fourths as large, one-half as large, one-third as large, or any other suitable value. The processing steps used to fabricate the CUT of FIG. 14 may be substantially the same as those used to fabricate the CUT of FIG. 13I, although the insulating layer deposited in FIG. 13D may be thicker in the context of fabricating the CUT of FIG. 14 to account for possible over-etch during FIG. 13C because of the narrower electrode. For example, the insulating layer deposited in FIG. 13D may be twice as thick as that used to fabricate the CUT of FIG. 13I, three times as thick, or any other suitable thickness.

As described previously, in some embodiments a CUT may include a piston, and processes for fabricating such pistons are described herein. As a further non-limiting example, the CUT of FIG. 15 may be fabricated to include piston 1502. The illustrated CUT is similar to that shown in FIG. 14. However, in patterning layers 1314 and 1316, a portion of those layers may be left in place over the center of the membrane 1310 to form the piston structure.

Pistons of various thicknesses may be desirable to provide various ultrasonic transducer behavior, in terms of frequency response, power handling capabilities, and robustness, among other possible considerations. An alternative CUT construction to that of FIG. 15, and having a thicker piston, is described in connection with FIGS. 16A and 16B.

Figure 15:
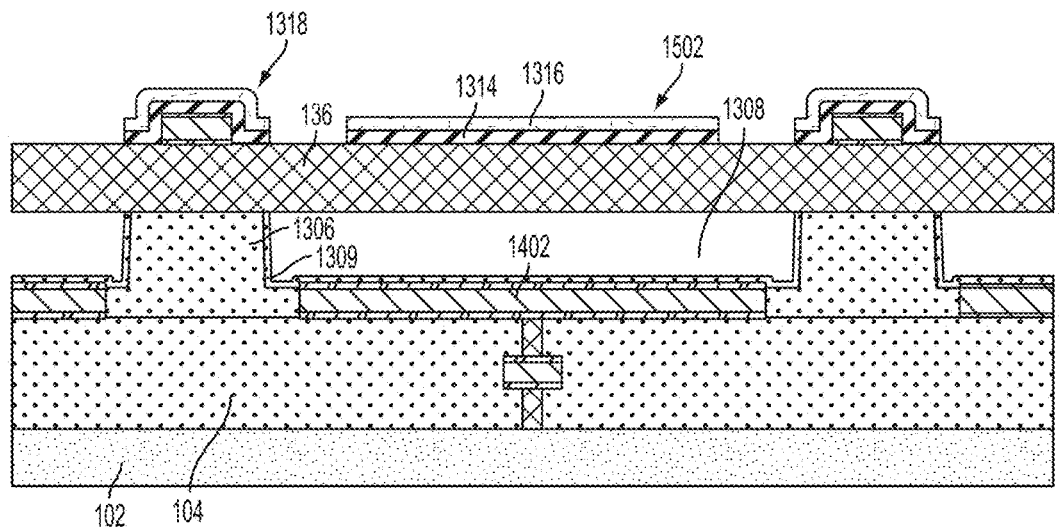
FIG. 15 illustrates an alternative CUT to that of FIG. 14 in which the CUT includes a piston membrane, according to a non-limiting embodiment of the present application.
Figure 16A:
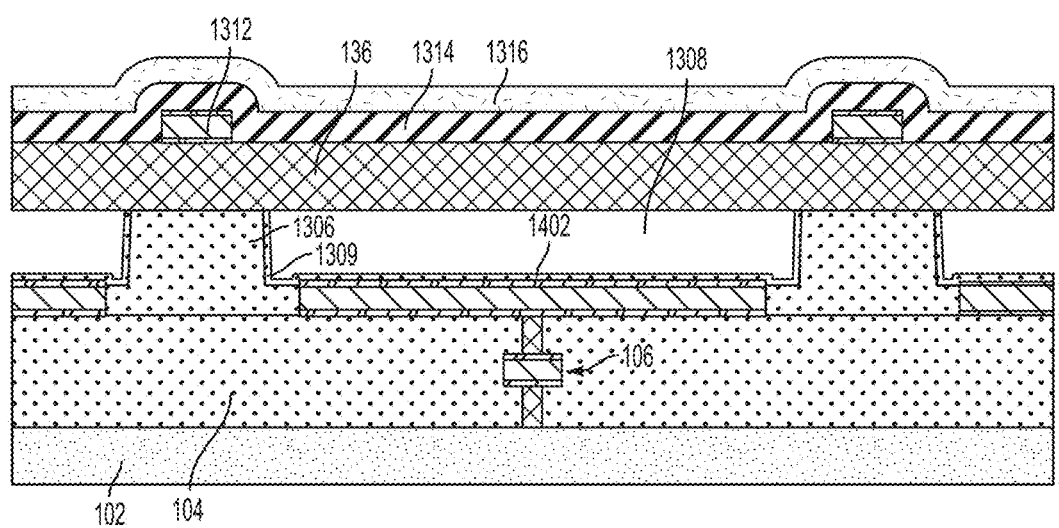
FIGS. 16A-16B illustrate a process sequence for forming an alternative CUT having a piston membrane and top side electrical contacts to the membrane, according to a non-limiting embodiment of the present application.

The structure of FIG. 16A is similar to that of previously described FIG. 13H. However, the layers 1314 and 1316 may be formed to greater thicknesses in the embodiments of FIG. 16A in anticipation of forming a thicker piston than that provided in FIG. 15. For example, the layers 1314 and 1316 may each be between approximately two and twenty microns, between approximately three and ten microns, any value within those ranges, or any other suitable value.

Figure 16B:
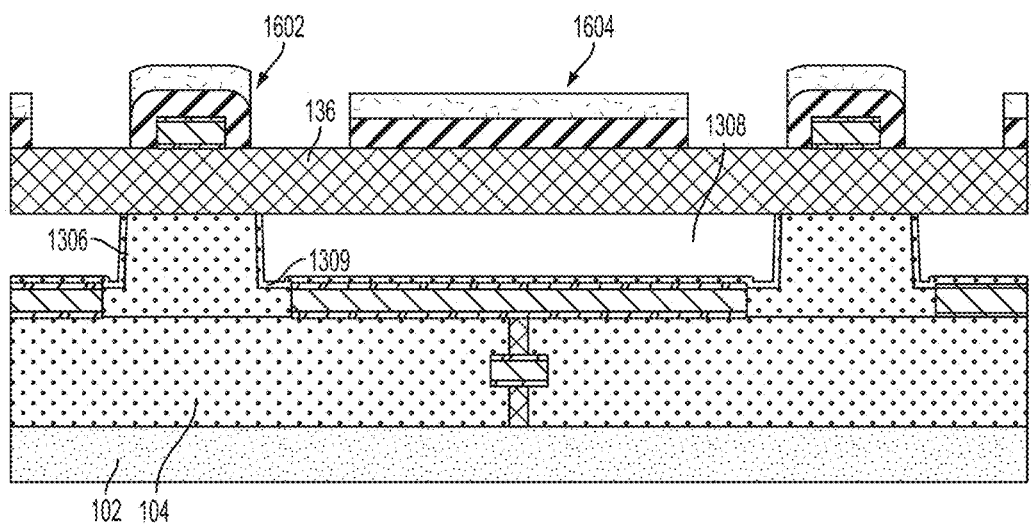

In FIG. 16B, the layers 1314 and 1316 may be patterned using a suitable etching technique to form passivated contacts 1602 and piston 1604.

It is noted that the CUT of FIG. 16B has the electrode 1402 which, as previously described, has a width smaller than the width of the cavity. However, the piston configuration of FIG. 16B may alternatively be formed as part of a CUT having an electrode that has the same width as or a larger width than the cavity of the CUT.

Figure 17A:
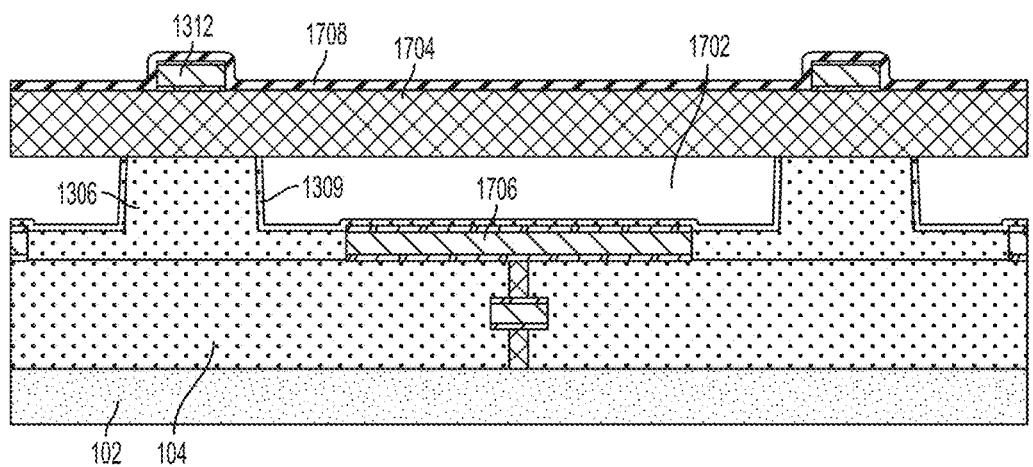
FIGS. 17A-17C illustrate a process sequence for forming a CUT having a piston membrane and top side electrical contacts to the membrane, according to a non-limiting embodiment of the present application.
Figure 17B:
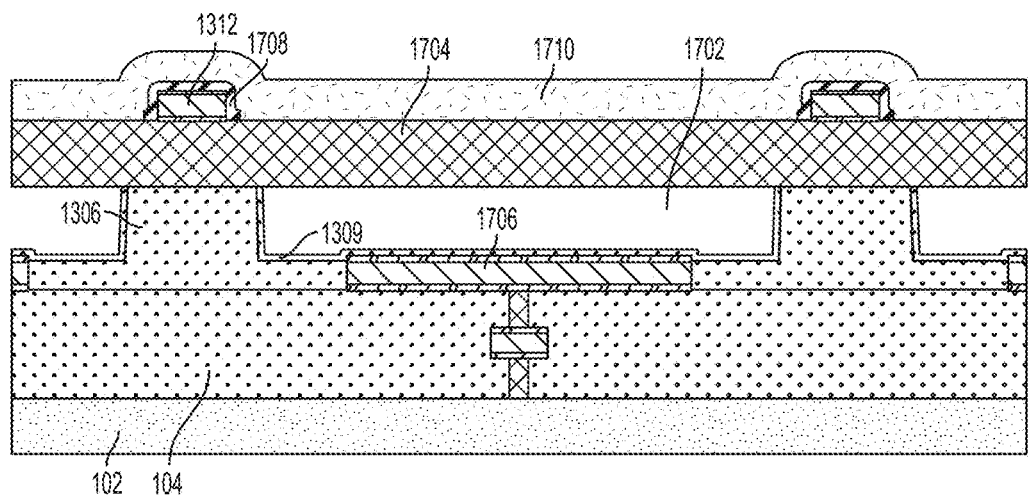
Figure 17C:
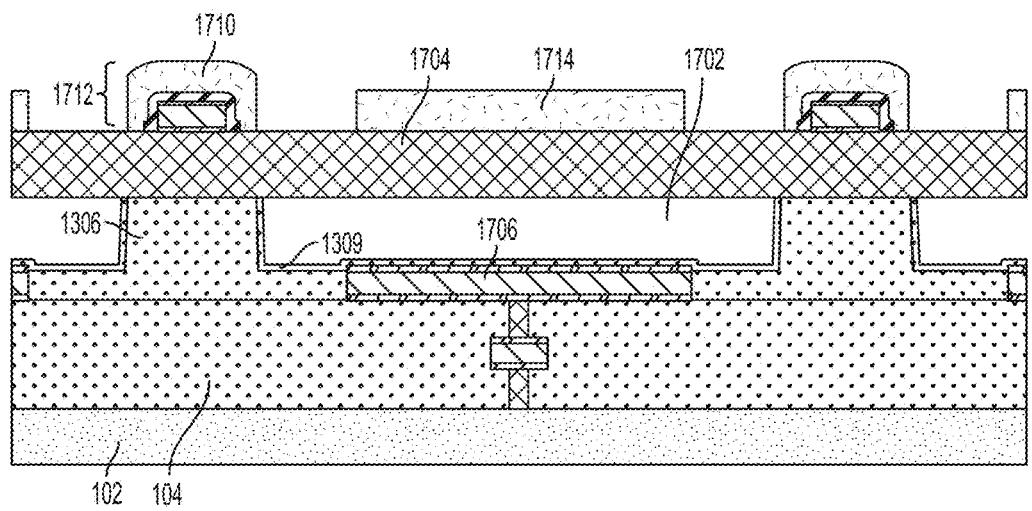

FIGS. 17A-17C illustrate a non-limiting manner of fabricating an alternative CUT design to that of FIGS. 15 and 16B, including a piston membrane having a width matched to the width of the electrode underlying the cavity.

As shown in FIG. 17A, the process may begin with a structure having a sealed cavity 1702 sealed with a membrane 1704 monolithically integrated with a CMOS wafer (e.g., using any suitable processing steps described herein). An electrode 1706 may be disposed underneath the cavity. The contacts 1312 may be formed in the manner previously described. Insulating layer 1708 may be deposited on the upper top side of the membrane 1704 and the contacts 1312. The insulating layer 1708 may be SiO$_2$ or other suitable insulating material.

As shown in FIG. 17B, the insulating layer 1708 may be patterned and then layer 1710 may be deposited on the top side of the membrane 1704. Layer 1710 may function as a passivation layer in some embodiments, and may be formed of Si$_3$N$_4$ or other suitable passivating material.

As shown in FIG. 17C, layer 1710 may then be suitably patterned to form passivated contacts 1712 and piston 1714. It can be seen that the layer 1710 may be patterned such that it fully covers the insulating layer 1708 of the passivated contact 1712, i.e., the layer 1710 extends down to the upper surface of the membrane 1704. In this manner, the layer 1710 may prevent humidity from passing through the insulating layer 1708 and harming (e.g., corroding) the contacts 1312.

As previously described, in some embodiments processes are provided for fabricating CUTS having a piston membrane in which the piston membrane is initially formed on a transfer wafer and monolithically integrated with a CMOS wafer by low temperature wafer bonding. A non-limiting example of a CUT formed in this manner and having top side electrical contacts to the membrane is described in connection with FIGS. 18A-18E.

Figure 18A:
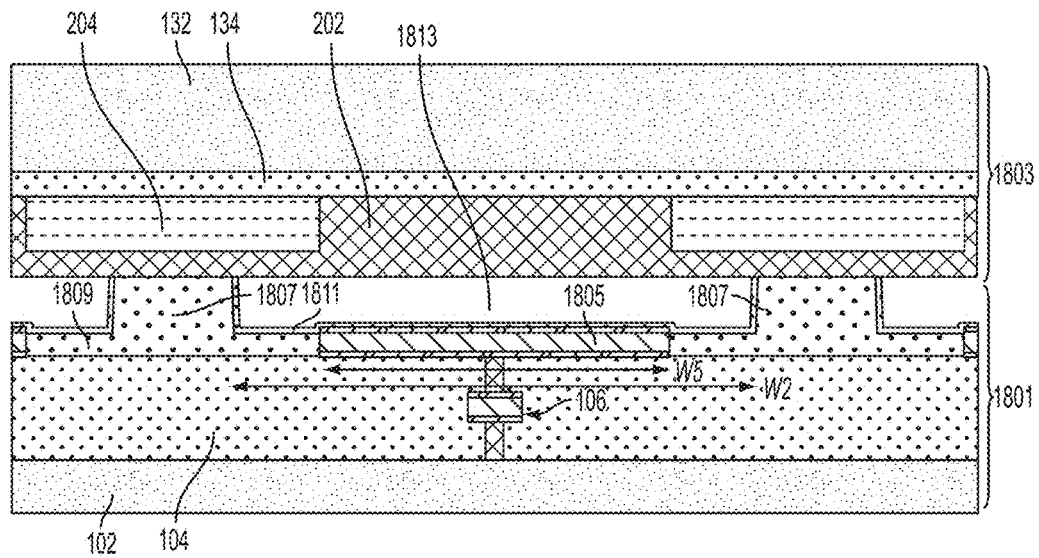
FIGS. 18A-18E illustrate an alternative process sequence for forming a CUT having a piston membrane and top side electrical contacts to the membrane, according to a non-limiting embodiment of the present application.

As shown in FIG. 18A, the process for fabricating such a CUT may begin by wafer bonding a CMOS wafer 1801 with a transfer wafer 1803 having several of the same layers as previously described for the transfer wafer 201 of FIG. 2A (i.e., having layers 132, 134, 202, and 204, but lacking 138). The CMOS wafer may include an electrode 1805 and sidewalls 1807, the latter of which may be formed by insulating layers 1809 and 1811 in the non-limiting embodiment illustrated. The wafer bonding may be a low temperature bonding process suitable to preserve structures such as silicon circuitry on the CMOS wafer, and may create a sealed cavity 1813. As shown, in this embodiment the width W5 of the electrode 1805 may be less than the width W2 of the cavity 1813.

Figure 18B:
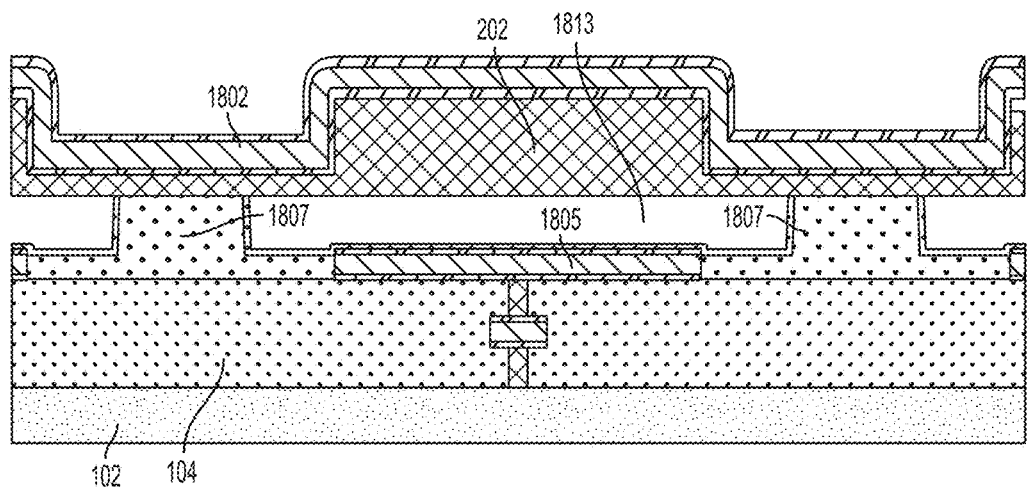

The base layer 132, insulating layer 134, and layer 204 may be removed from the transfer wafer 1803 in any of the manners previously described for such removal. Then, as shown in FIG. 18B, a metal layer 1802, for example having the structure previously described in connection with second metallization layer 108, may be deposited.

Figure 18C:
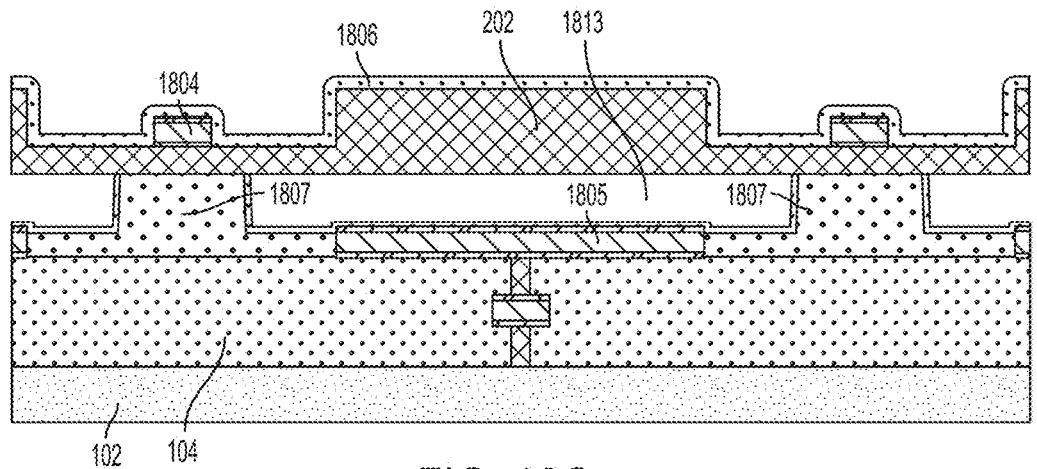

As shown in FIG. 18C, the metal layer 1802 may be patterned to form contacts 1804 and an insulating layer (e.g., SiO2) 1806 may be deposited.

Figure 18D:
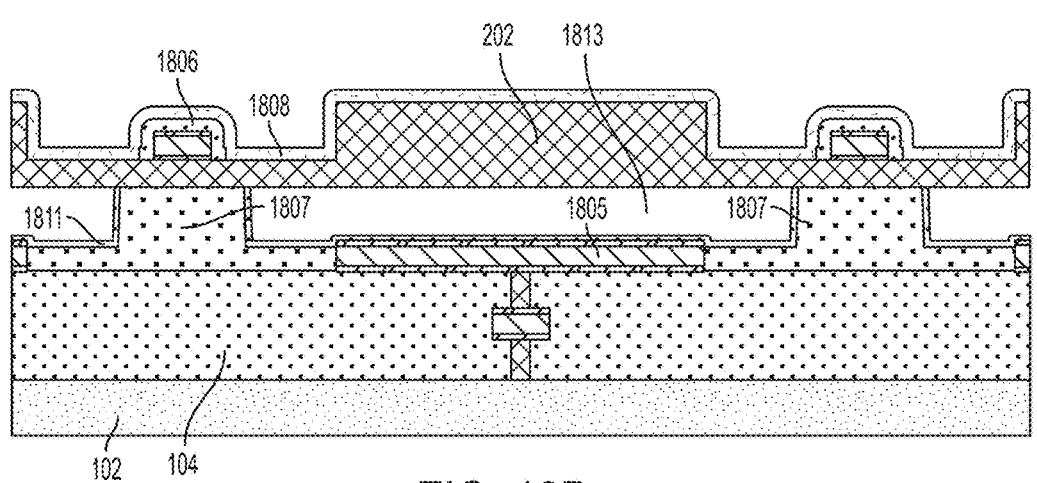
Figure 18E:
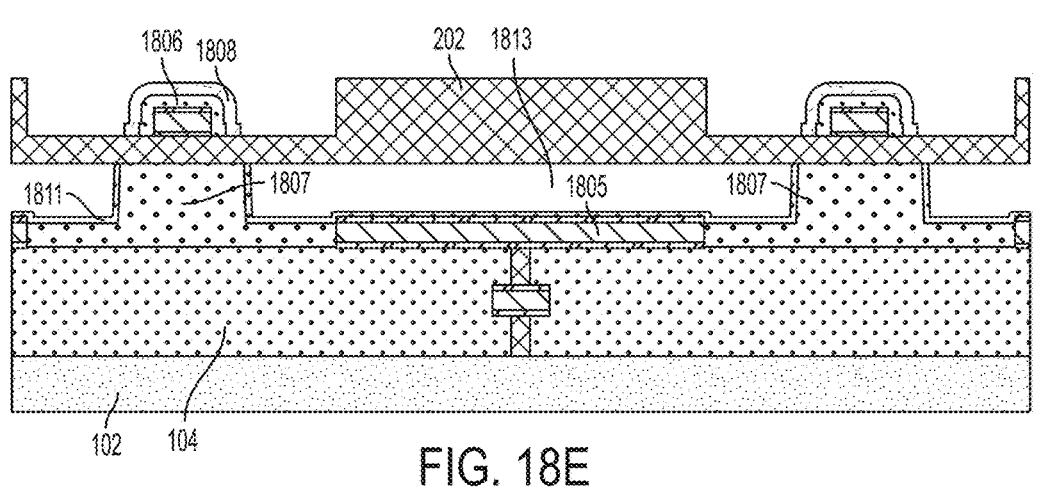

As shown in FIG. 18D, the insulating layer 1806 may be patterned and then a layer 1808 may be deposited as a passivation layer. In some embodiments, the layer 1808 may be $Si_3N_4$, though other materials may be used. As shown in FIG. 18E, the layer 1808 may be patterned in a manner such that it touches the piston 202 and thereby fully covers the remaining portion of layer 1806. In this manner, layer 1808 may prevent humidity from passing through the insulating layer 1806 and harming (e.g., corroding) the contacts 1804.

Figure 19A:
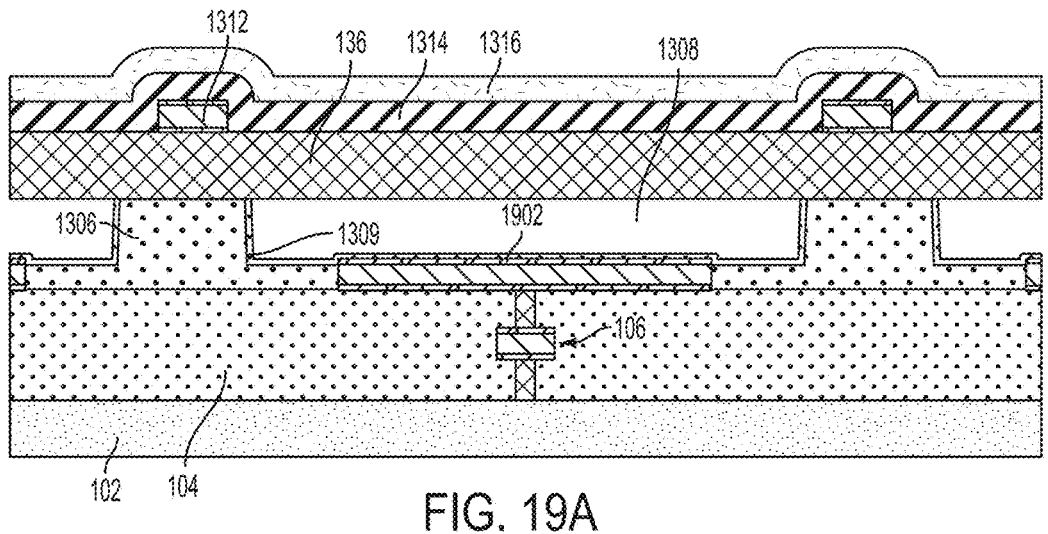
FIGS. 19A-19B illustrate a further alternative process sequence for forming a CUT having a piston membrane and top side electrical contacts to the membrane, according to a non-limiting embodiment of the present application.
Figure 19B:
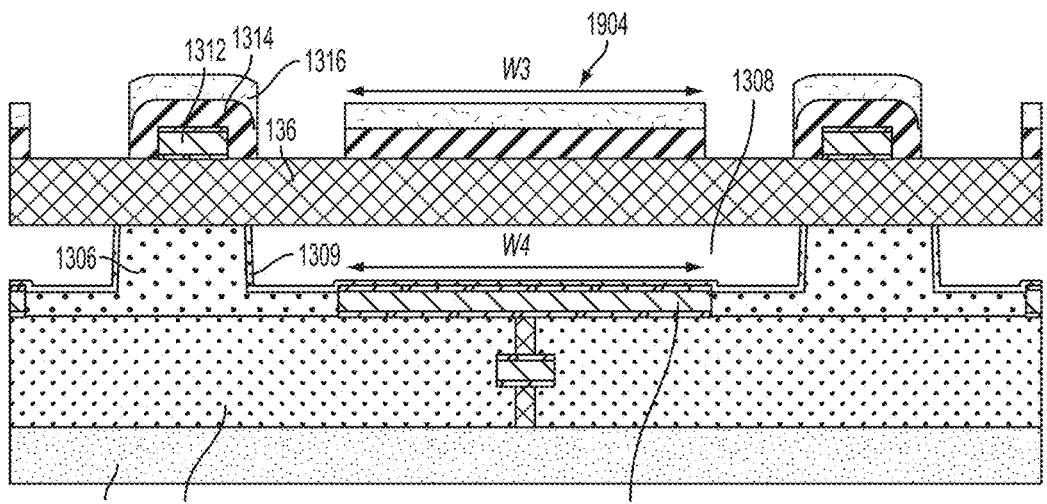

FIGS. 19A-19B illustrate a process for fabricating a CUT having a piston membrane with a piston width matching the width of an electrode beneath the cavity of the CUT. As shown in FIG. 19A, the process may begin with a structure similar to that previously described in connection with FIG. 16A except that the electrode 1902 beneath the cavity may be narrower.

As shown in FIG. 19B, the layers 1314 and 1316 may be patterned to form a piston 1904 having a width W3 the same as or substantially the same as the width W4 of the electrode 1902.

As described previously, in some embodiments a CUT may include a membrane stop. The membrane stop may be positioned at the bottom of a cavity of the CUT in some embodiments. A non-limiting example of such a CUT with electrical contacts on a top side of the membrane of the CUT is shown in connection with FIGS. 20A-20I.

Figure 20A:
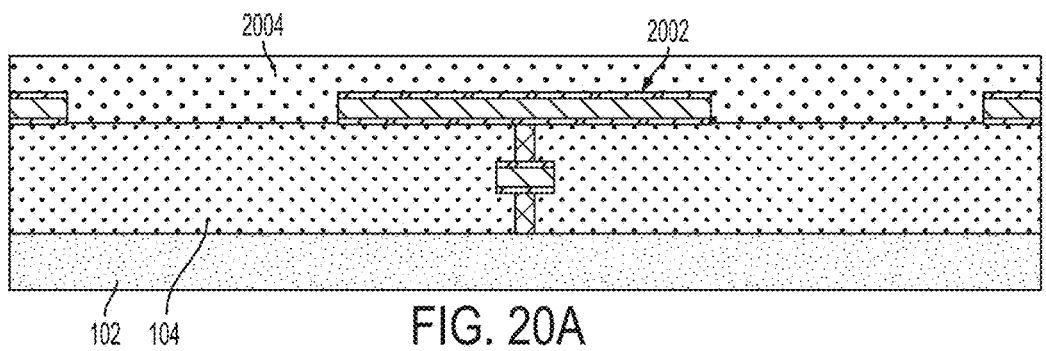
FIGS. 20A-20I illustrate a process sequence for forming a CUT having electrical contacts on a top side of a membrane of the CUT and having a membrane stop on a bottom surface of a cavity of the CUT, according to a non-limiting embodiment of the present application.
Figure 20B:
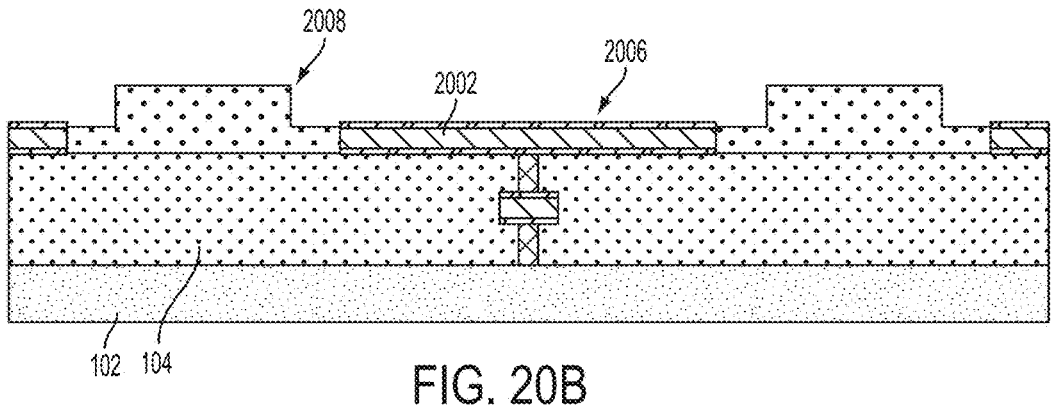

As shown in FIG. 20A, the process may begin with a CMOS wafer including an electrode 2002 covered by an insulating layer 2004. An etch may then be performed as shown in FIG. 20B to form a cavity 2006 having sidewalls or spacers 2008.

Figure 20C:
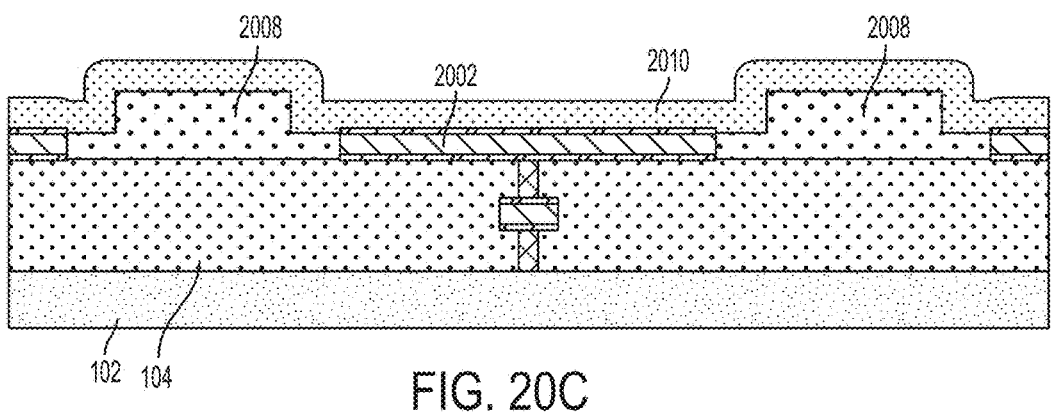
Figure 20D:
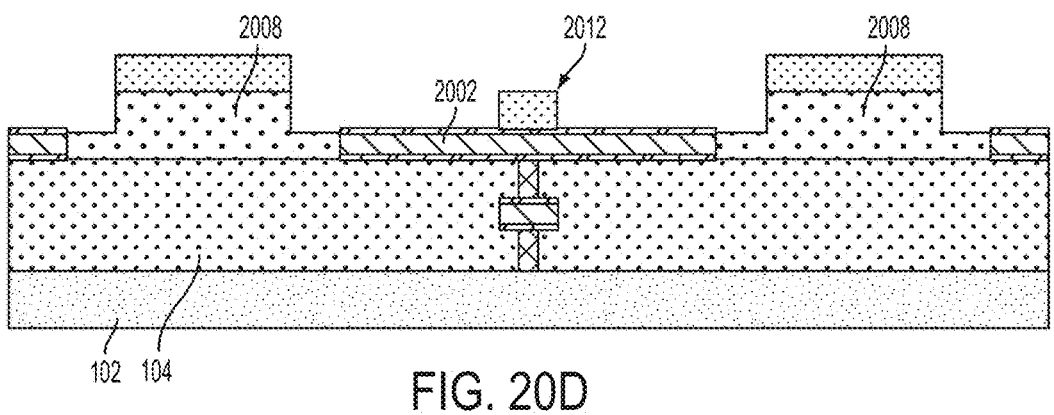

Subsequently, in FIG. 20C, an insulating layer 2010 may be deposited. The insulating layer 2010 may be $SiO_2$ or any other suitable insulating material. The insulating layer 2010 may be patterned as shown in FIG. 20D to form a membrane stop 2012 in the cavity 2006.

Figure 20E:
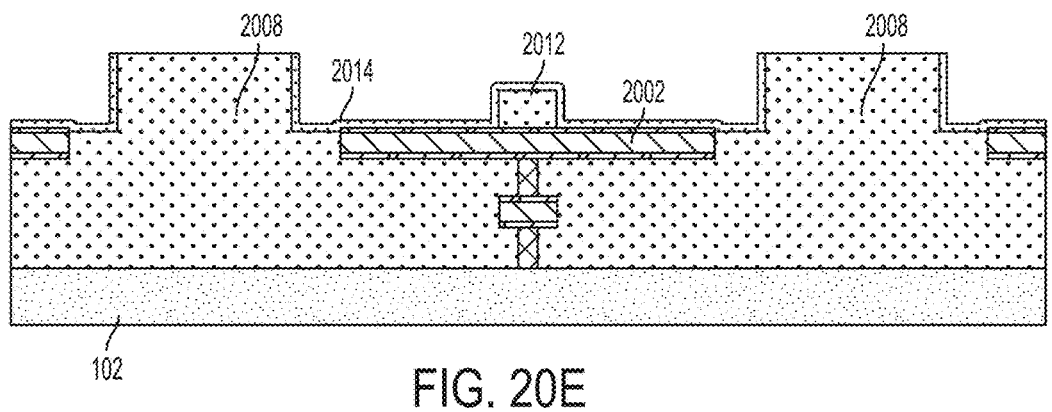

As shown in FIG. 20E, an insulating layer (e.g., $SiO_2$) 2014 may be deposited. The insulating layer 2014 may act to prevent an electrical short circuit if the membrane of the CUT (shown in FIG. 20I) bottoms out. However, because the membrane stop 2012 itself may be formed of an insulating material, the insulating layer 2014 may be omitted in some embodiments.

After deposition of the insulating layer 2014, the CMOS wafer may be planarized (e.g., using CMP) and the surface prepared for wafer bonding. Thus, the insulating layer 2014 may be removed from the top of the sidewalls 2008.

Figure 20F:
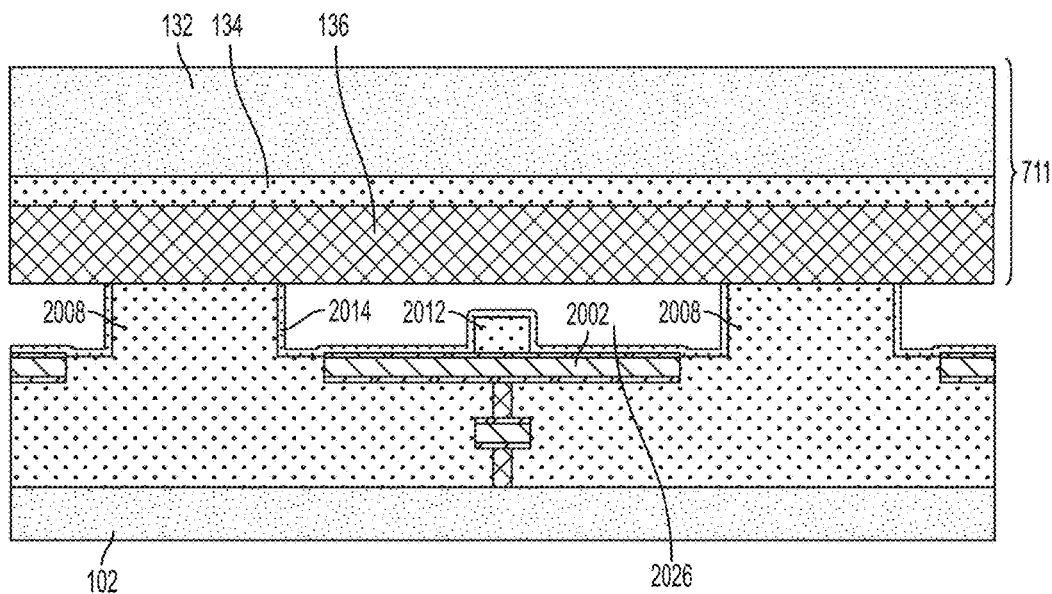

As shown in FIG. 20F, wafer bonding may then be performed to bond the CMOS wafer with a transfer wafer 711 of the type previously described in connection with FIG. 7G (e.g., a multi-layer wafer having a base silicon substrate, a buried oxide layer, and a silicon membrane layer, formed of single crystal silicon, polysilicon or amorphous silicon in some embodiments). The wafer bonding process may be a low temperature process (e.g., below 450° C.) to preserve CMOS structures (e.g., ICs) on the CMOS wafer. The wafer bonding process may result in a sealed cavity 2026.

Figure 20G:
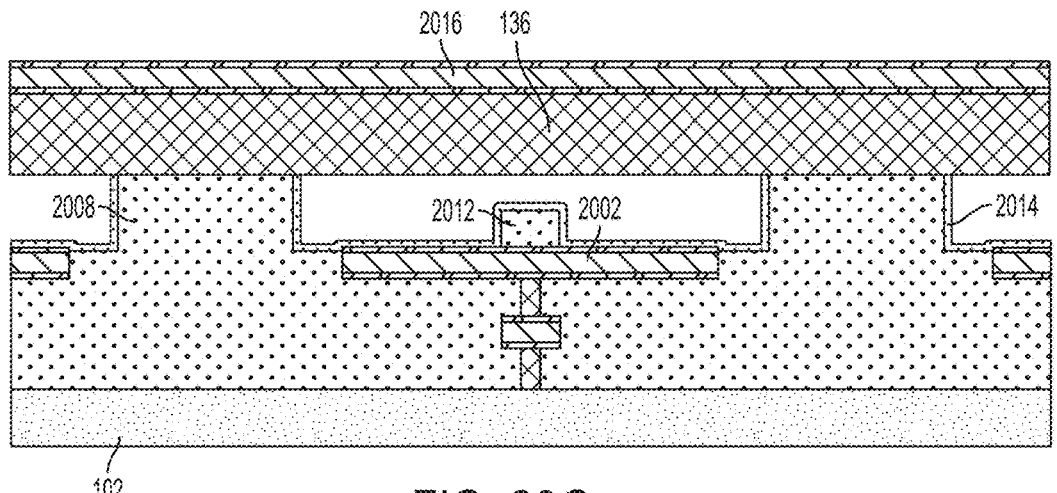

As shown in FIG. 20G, the base layer 132 and insulating layer 134 may be removed (using any of the techniques described previously herein for removing such layers) and a metallization layer 2016 may be deposited. The metallization layer 2016 may have the same construction as second metallization layer 108 in some embodiments, though alternative configurations are possible.

Figure 20H:
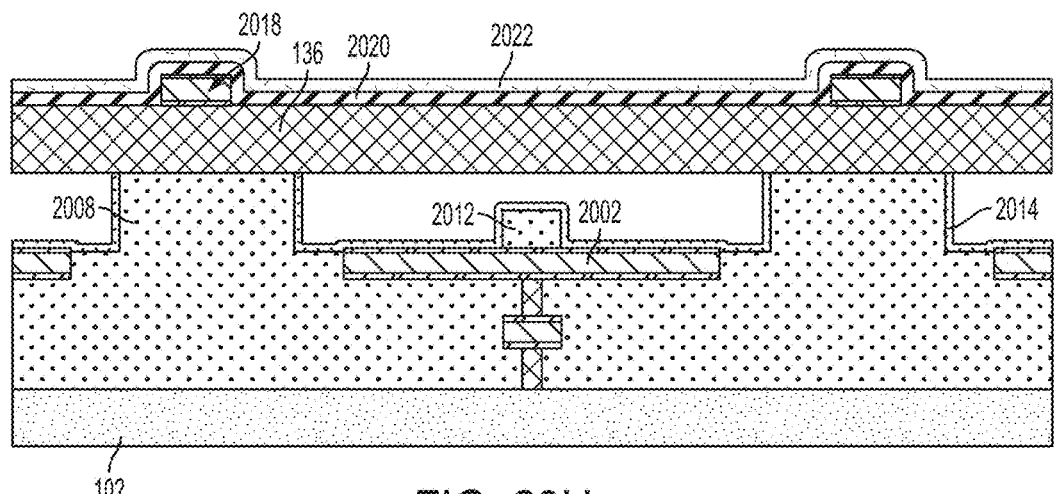

As shown in FIG. 20H, the metallization layer 2016 may be patterned to form contacts 2018, and layers 2020 and 2022 may be deposited. In some embodiments, layers 2020 and 2022 may serve as passivation layers, and may be formed of $SiO_2$ and $Si_3N_4$, respectively.

Figure 20I:
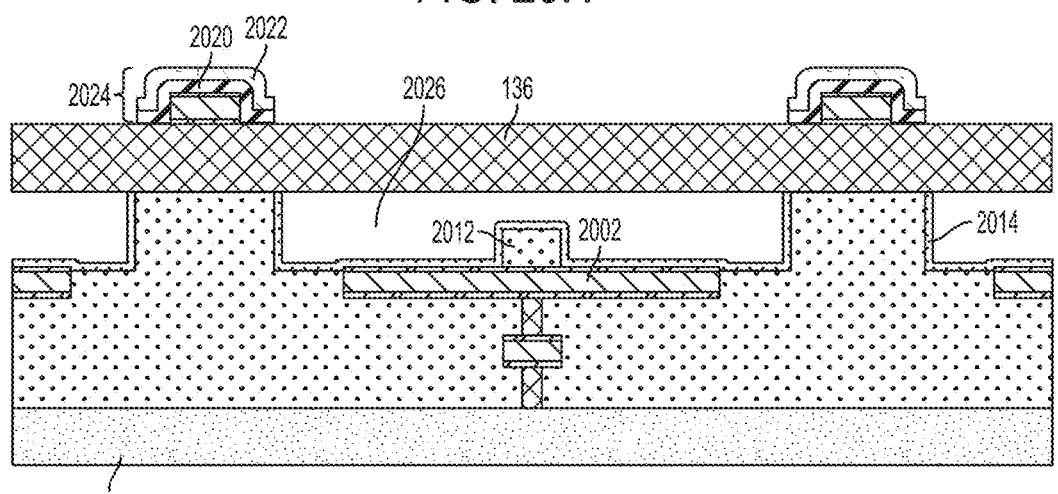

As shown in FIG. 20I, the layers 2020 and 2022 may be patterned to produce passivated contacts 2024 on the top side of the membrane of the CUT. The passivated contacts 2024 may be used to apply electrical signals to and/or receive electrical signals from the membrane. In operation, the membrane may contact the membrane stop 2012 when vibrating. The membrane stop 2012 may alter the frequency behavior of the CUT in the manner previously described for membrane stops.

FIGS. 21A-21F illustrate an alternative process for fabricating a CUT having a membrane stop and top side electrical contacts to the membrane of the CUT. In this embodiment, the membrane stop may be on the underside of the membrane of the CUT rather than at the bottom of the cavity of the CUT.

Figure 21A:
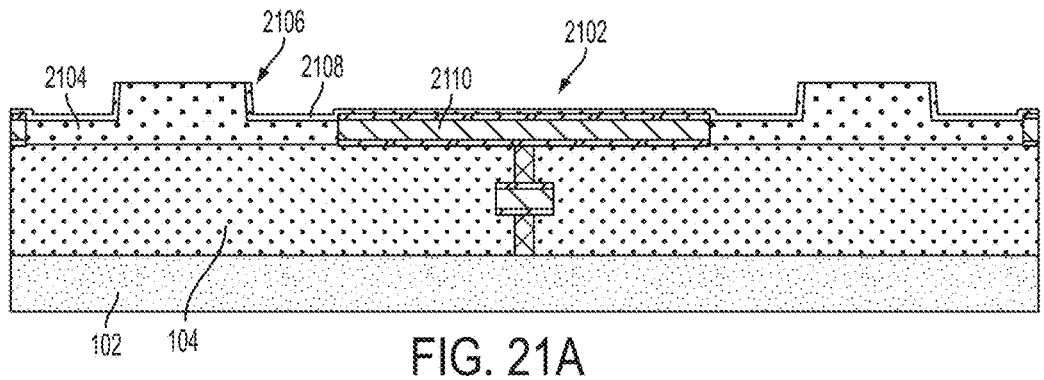
FIGS. 21A-21F illustrate a process sequence for forming a CUT having electrical contacts on a top side of a membrane of the CUT and having a membrane stop on a bottom side of the membrane, according to a non-limiting embodiment of the present application.

The process may begin as shown in FIG. 21A with a CMOS wafer prepared for wafer bonding. The CMOS wafer may have a cavity 2102 formed in an insulating layer 2104 patterned to define sidewalls or spacers 2106. A second insulating layer 2108 may cover the electrode 2110.

Figure 21B:
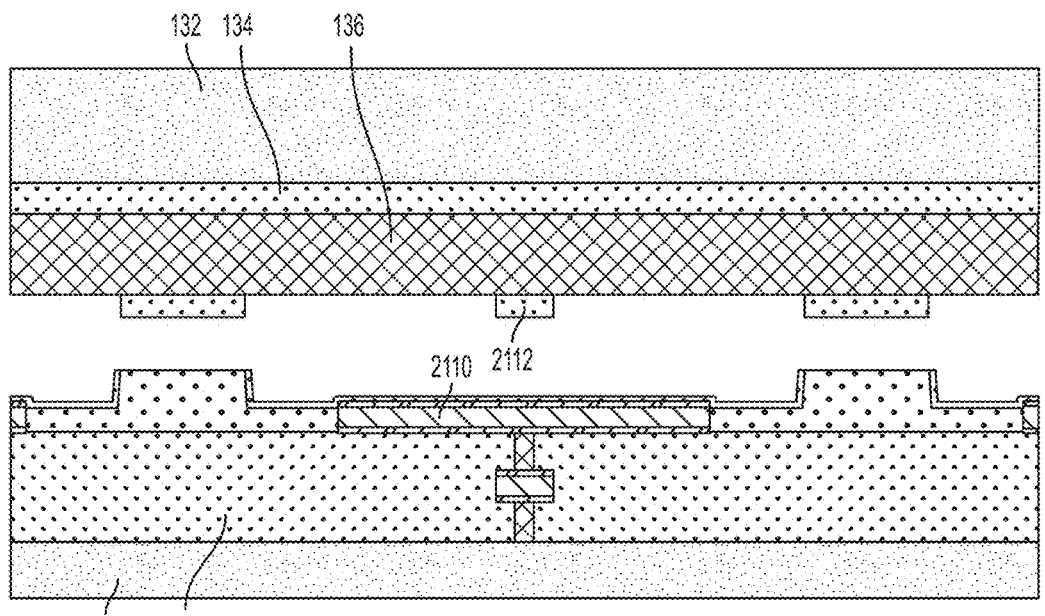

As shown in FIG. 21B, the CMOS wafer may be bonded to a transfer wafer having a patterned insulating layer forming a membrane stop 2112. The bonding may result in a sealed cavity 2122, as shown in FIG. 21C.

Figure 21C:
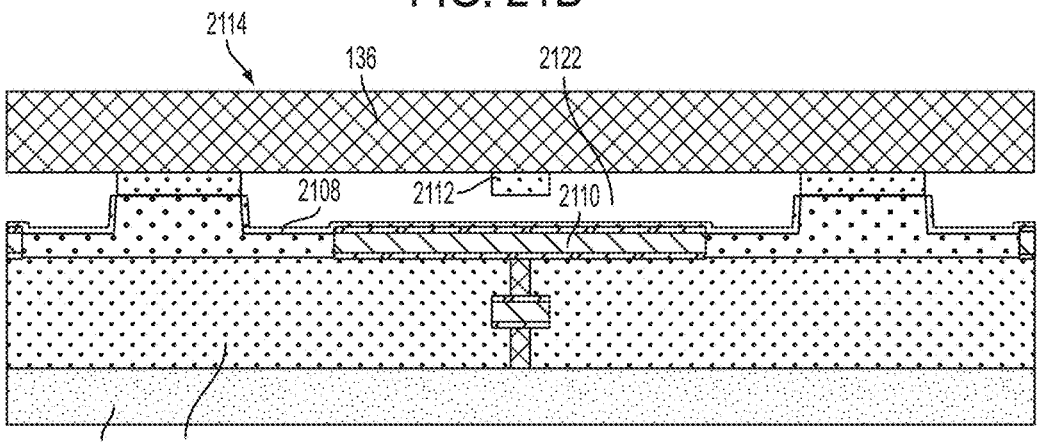

As shown in FIG. 21C, the base layer 132 and insulating layer 134 may be removed, leaving a membrane 2114.

Figure 21D:
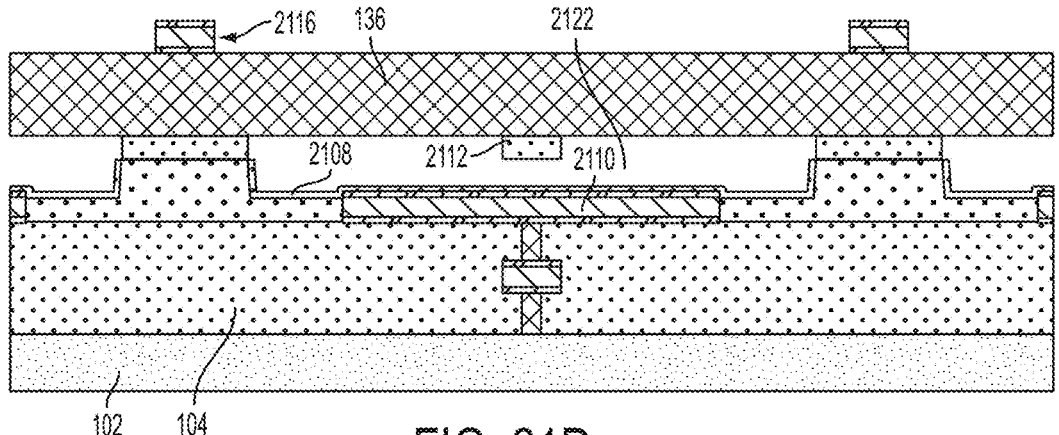
Figure 21E:
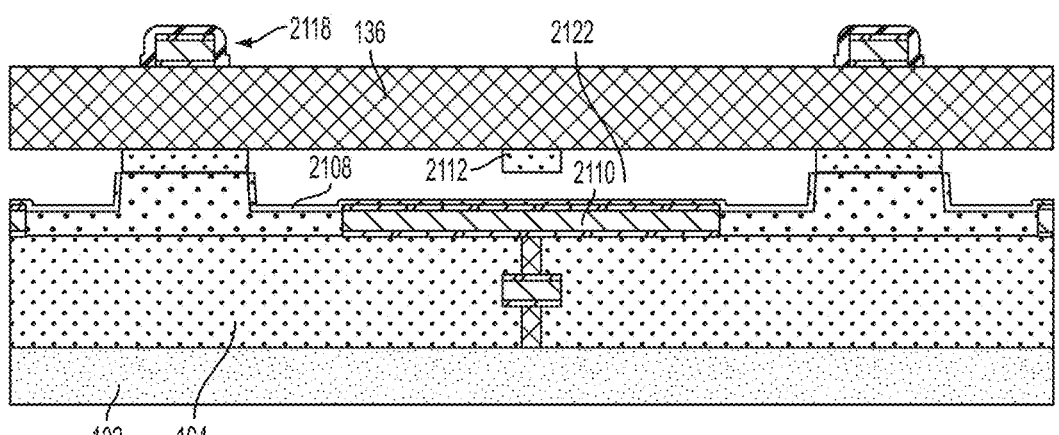

Electrical contacts 2116 may then be formed on the top side of the membrane 2114, for example by depositing and patterning a metallization layer, as shown in FIG. 21D. Subsequently, in FIG. 21E, a passivation layer 2118 may be deposited and patterned to passivate the electrical contacts 2116. The passivation layer 2118 may be formed of $SiO_2$ in some embodiments.

Figure 21F:
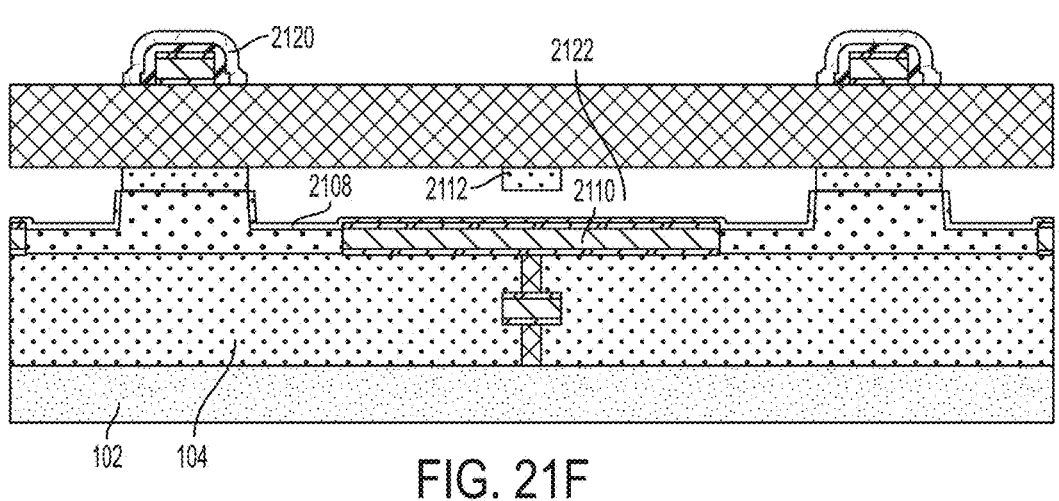

In FIG. 21F, a second passivation layer, for example formed of $Si_3N_4$, may be deposited and patterned over the electrical contacts 2116.

Thus, the CUT of FIG. 21F may include a membrane stop on a bottom side of the membrane with top side electrical contacts to the membrane. The process for forming the CUT may involve only low temperature processing, thus preserving structures formed on the CMOS wafer, such as ICs.

The structures described herein may have various dimensions suitable for use as ultrasonic transducers, for example in ultrasound imaging applications and/or HIFU applications. For example, the cavity sizes (e.g., widths, or aperture sizes more generally, and depths) may assume any suitable values to provide desired frequency characteristics. The membranes and piston membrane may likewise assume any suitable values. In some embodiments, the dimensions may be selected to make the CUTs suitable for low voltage operation, thus facilitating their integration with low voltage CMOS ICs, though not all embodiments are limited in this respect. For example, high voltage designs may also be used, for example in the context of CUTs operating to provide HIFU. When designed for low voltage operation, the CUTs may have suitable dimensions to operate at, for example, less than 70 V, less than 50 V, less than 30 V, less than 20 V, less than 10 V, between 2 V and 60 V, between 10 V and 30 V, between 15 V and 25 V, any voltage within those ranges, or any other suitable voltages. Operation at these lower voltages may be allowed, at least in part, by making the membranes sufficiently thin to flex suitably at these lower voltages. Non-limiting examples of membrane thicknesses achievable with embodiments of the present application are described further below.

As non-limiting examples, cavities of CUTs as described herein may have widths, or more generally apertures, between approximately 5 microns and approximately 500 microns, between approximately 20 microns and approximately 100 microns, may be approximately 30 microns, approximately 40 microns, approximately 50 microns, any width or range of widths in between, or any other suitable width. In some embodiments, the width may be selected to maximize the void fraction, i.e., the amount of area consumed by the cavities compared to the amount of area consumed by surrounding structures.

The cavities of CUTs described herein may have any suitable depths, for example, between approximately 0.05 microns and approximately 10 microns, between approximately 0.1 microns and approximately 5 microns, between approximately 0.5 microns and approximately 1.5 microns, any depth or range of depths in between, or any other suitable depth. In some embodiments, the cavity dimensions and/or the membrane thickness of any membrane overlying the cavity may impact the frequency behavior of the membrane, and thus may be selected to provide a desired frequency behavior (e.g., a desired resonance frequency of the membrane). For example, it may be desired in some embodiments to have an ultrasonic transducer with a center resonance frequency of between approximately 20 kHz and approximately 200 MHz, between approximately 1 MHz and approximately 10 MHz, between approximately 2 MHz and approximately 5 MHz, between approximately 50 kHz and approximately 200 kHz, of approximately 2.5 MHz, approximately 4 MHz, any frequency or range of frequencies in between, or any other suitable frequency. For example, it may be desired to use the devices in air, gas, water, or other environments, for example for medical imaging, materials analysis, or for other reasons for which various frequencies of operation may be desired. The dimensions of the cavity and/or membrane may be selected accordingly.

CUTs as described herein may have any suitable membrane thicknesses. For example, the membranes described herein may have a thickness (e.g., as measured in a direction generally parallel to a depth of a corresponding cavity) less than 100 microns, less than 50 microns, less than 40 microns, less than 30 microns, less than 20 microns, less than 10 microns, less than 5 microns, less than 1 micron, less than 0.1 microns, any range of thicknesses in between, or any other suitable thickness. The thickness may be selected in some embodiments based on a desired acoustic behavior of the membrane, such as a desired resonance frequency of the membrane.

When a piston membrane is formed, the center and outer portions of the piston membrane may have any suitable thicknesses and any suitable ratios of thicknesses. In some embodiments, the outer portion of the membrane (connecting the membrane to the CMOS wafer) may be made as thin as possible (e.g., between approximately 50 nm and approximately 100 nm, as non-limiting examples). The center portions of the piston membranes may have any thickness in accordance with those previously described for membranes. In some embodiments, both the outer and center portions of the piston membranes may have thicknesses between approximately 1 micron and approximately 100 microns, between approximately 10 microns and approximately 50 microns, any value with such ranges, or any other suitable values.

Figure 26:
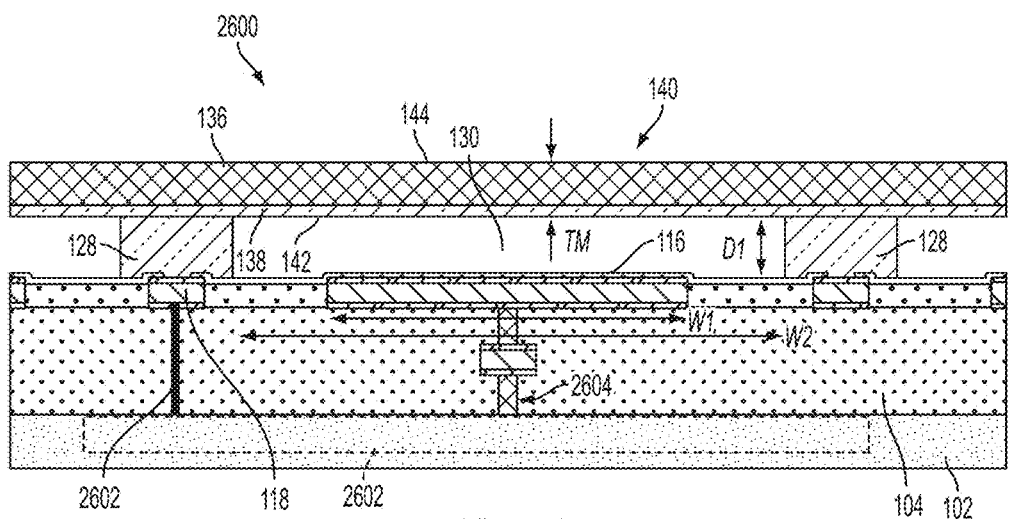
FIG. 26 illustrates the ultrasonic transducer of FIG. 1K connected to an integrated circuit in the CMOS wafer, with the integrated circuit disposed beneath the ultrasonic transducer.

As described previously, an aspect of the present application provides an ultrasonic transducer cell integrated with CMOS circuitry where the circuitry is disposed beneath the transducer. FIG. 26 illustrates a non-limiting example of a such a device, using the ultrasonic transducer of FIG. 1K.

As shown, the device 2600 may include the ultrasonic transducer of FIG. 1K with the addition of an integrated circuit 2602. The integrated circuit may be formed in the base layer 102 of the CMOS wafer. For example, the base layer may be a bulk silicon layer, and the integrated circuitry may include one or more active silicon circuit elements (e.g., MOS transistors having doped source and drain regions in the silicon), capacitors, resistors, or other circuit components. The integrated circuit 2602 may be suitable to operate the ultrasonic transducer in transmit and/or receive modes.

As shown, both the electrode 116 and the contact 118 may be connected to the integrated circuit 2602. The electrode 116 may be connected by the illustrated via 2604 which may, for example, directly contact a doped source/drain terminal of a MOS transistor in the base layer 102. The contact 118 may be connected to the integrated circuit 2602 by a conductive line 2606, which may be a via in some embodiments. Other manners of making connection from the electrode 116 and the contact 118 to the integrated circuit 2602 are also possible.

As previously described and as shown in FIG. 26, in some embodiments local connection may be made to the membrane of a CUT rather than global connection. For example, contact 118 provides for local connection to the membrane of the illustrated CUT. Such local connection may be beneficial to reduce unwanted electrical behavior in biasing the membrane (e.g., unwanted capacitances which can arise with long signal lines), among other potential benefits provided by local connections.

In some embodiments, the membrane of the CUT may be biased, and in some such embodiments the contact 118 may be used to supply the bias signal. In such situations, the contact 118 may be connected to the integrated circuit 2602 via a capacitor (not shown) for providing or maintaining a desired bias level. Other biasing configurations are also possible.

In some embodiments, the electrode 116 may be driven, and thus the integrated circuit 2602 may be suitably connected to drive the electrode. In some embodiments, the electrode 116 may be biased, rather than the membrane.

Thus, it should be appreciated that various operating scenarios are possible for the ultrasonic transducer. The integrated circuit 2602 may include suitable circuitry (e.g., switching circuitry, capacitors, etc.) to allow for the various modes of operation, including driving the membrane, driving the electrode 116, or other modes of operation.

Various examples of transfer wafers have been described herein for use with various embodiments. In some embodiments, traditional SOI wafers may be used, having a silicon bulk wafer as a handle layer, buried oxide layer, and monocrystalline silicon layer. However, as previously described, some embodiments implement alternative types of transfer wafers, including transfer wafers having polysilicon or amorphous silicon layers. Since the transfer wafers may be used to form membranes, pistons, and/or membrane stops rather than being used to provide silicon layers for supporting high quality circuitry, Applicants have appreciated that high quality monocrystalline silicon layers need not be used in all embodiments. Rather, as previously described, membranes, pistons, and membrane stops may be formed of polysilicon, amorphous silicon, oxides, TiN, or other suitable materials. Thus, Applicants have appreciated that transfer wafers having such materials may be implemented in some embodiments instead of traditional SOI wafers, and that such alternative types of transfer wafers may be fabricated with significantly less effort and cost than required for form traditional SOI wafers. Accordingly, use of such relatively simple multi-layer transfer wafers may significantly simplify production of CUTs and may allow for cost effective large scale production of CUTs.

Non-limiting examples of how to fabricate some of the transfer wafers described herein are now described. For example, in those embodiments in which the transfer wafer 131 has polysilicon (e.g., doped polysilicon) or amorphous silicon as the layer 136, the transfer wafer may be fabricated starting with a silicon bulk wafer as base layer 132, the depositing a layer of SiO$_2$ as insulating layer 134, and then depositing polysilicon or amorphous silicon. Next, the layer 138 (e.g., TiN) may be deposited. Performing these steps may require significantly less precision than those used to form traditional SOI wafers, and thus fabricating transfer wafer 131 in this manner may simplify the overall process for forming a CUT and reduce the cost of the same.

FIGS. 23A-23D illustrate a process sequence for fabricating the transfer wafer 1803 of FIGS. 9A and 18A, having a piston formed therein, according to a non-limiting embodiment of the present application.

Figure 23A:
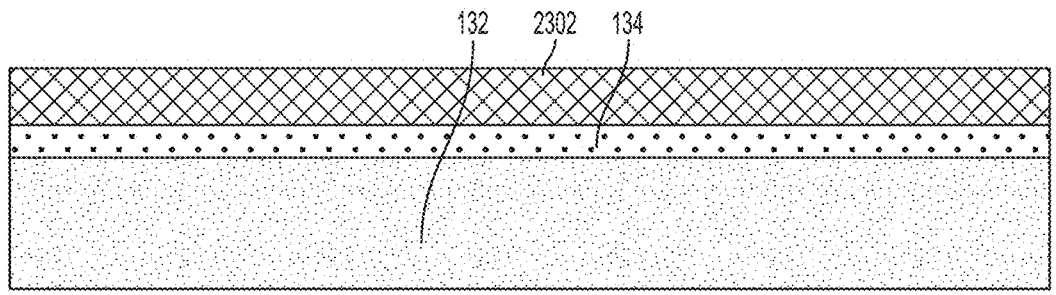
FIGS. 23A-23D illustrate a process sequence for fabricating a transfer wafer having a piston formed therein, according to a non-limiting embodiment of the present application.

Starting with the base layer 132 (e.g., silicon), the insulating layer 134 (e.g., SiO$_2$) may be deposited, followed by deposition of a layer 2302 as shown in FIG. 23A. The layer 2302 may form part of the piston 202 previously described, and thus may be made of the material desired for the piston. For example, the layer 2302 may be doped polysilicon in some embodiments, or may be amorphous silicon in some embodiments.

Figure 23B:
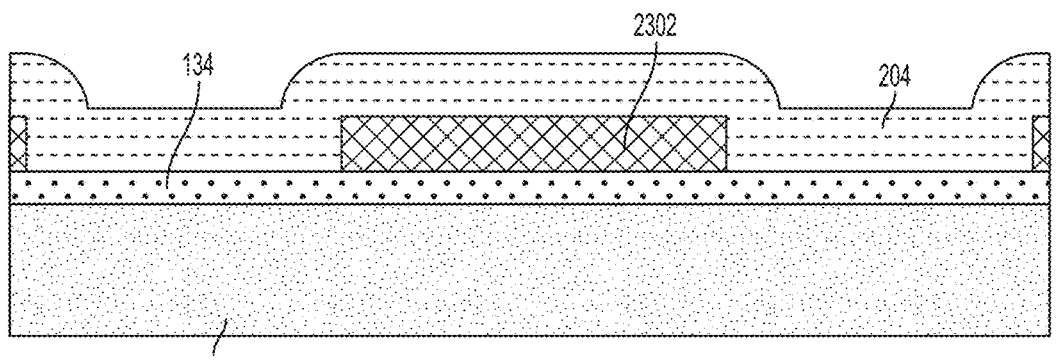

As shown in FIG. 23B, the layer 2302 may be patterned and layer 204, previously described, may be deposited. The layer 204 may be an insulating material, such as SiO$_2$ formed by TEOS or other suitable insulating material. CMP may be performed and the wafer may be planarized.

Figure 23C:
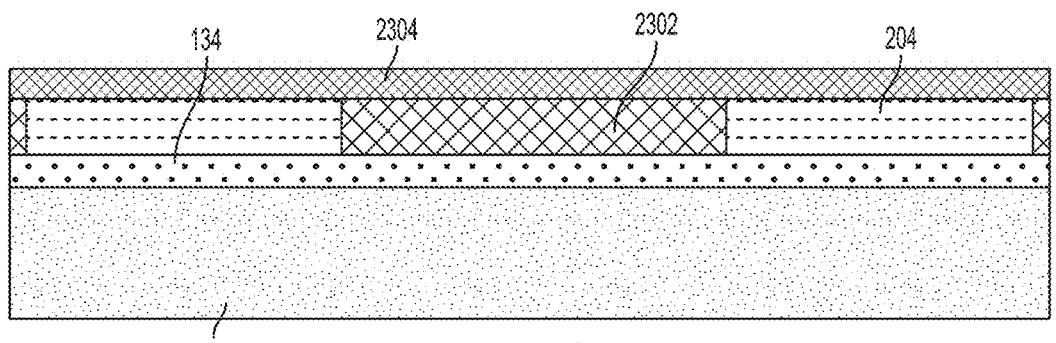

Then, as shown in FIG. 23C, a layer 2304 may be deposited. The layer 2304 may form part of the piston 202 and thus may be formed of the material desired for the piston. For example, the layer 2302 may be doped polysilicon in some embodiments, or may be amorphous silicon in some embodiments. CMP may then be performed.

Figure 23D:
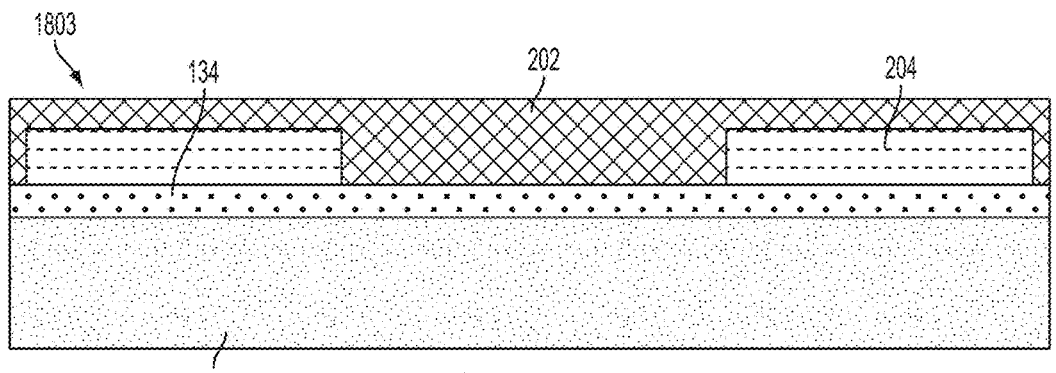

At the stage of processing illustrated in FIG. 23C, the layers 2302 and 2304 which will make up the piston 202 are in place. However, they do not define a unitary body since they have been deposited in separate steps, as reflected by the horizontal line between the two layers. Thus, to achieve the transfer wafer 1803 with the piston 202 representing a unitary body, an anneal may be performed, thus producing the finalized transfer wafer 1803 as shown in FIG. 23D. The anneal need not be a low temperature anneal, though it could be, since the transfer wafer is fabricated separately from the CMOS wafers described herein and therefore fabrication of the transfer wafer may include processing steps at temperatures which would damage CMOS circuitry if performed on a CMOS wafer. Moreover, it should be appreciated that the described steps for forming the transfer wafer 1803 are relatively simple compared to those required to form a traditional SOI wafer.

Optionally, the transfer wafer 1803 shown in FIG. 23D may be further processed by depositing previously described layer 138 (e.g., TiN), to produce the transfer wafer 201 of FIG. 2A.

Figure 24A:
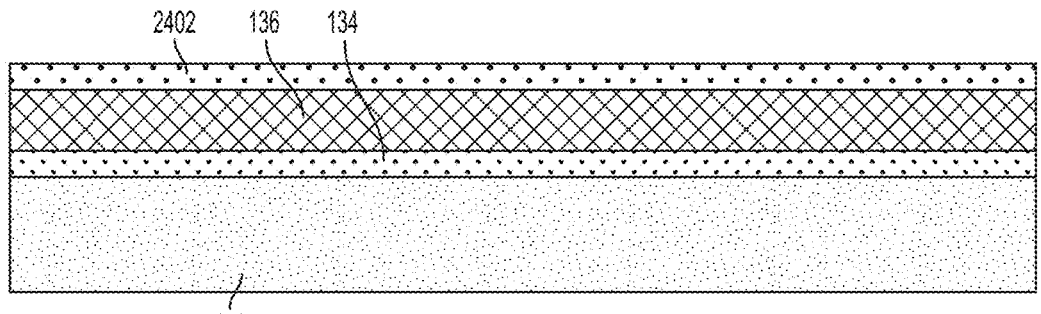
FIGS. 24A-24B illustrate a process sequence for fabricating a transfer wafer having a membrane stop, according to a non-limiting embodiment of the present application.
Figure 24B:
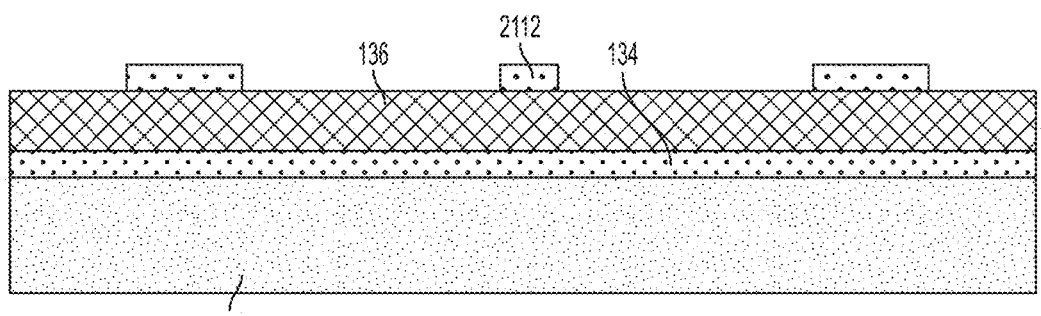

FIGS. 24A-24B illustrate a process sequence for fabricating a transfer wafer of the type shown in FIG. 21B, having a membrane stop, according to a non-limiting embodiment of the present application. Starting with the base layer 132 (e.g., silicon), the insulating layer 134 (e.g., SiO$_2$) may be deposited. Then previously described layer 136 may be deposited. An insulating layer 2402 may then be deposited to produce the structure of FIG. 24A. The insulating layer 2402 may be SiO$_2$, and may be formed by TEOS or other suitable deposition method.

As shown in FIG. 24B, the insulating layer 2402 may be patterned to form the membrane stop 2112. Thus, it should be appreciated that fabrication of the transfer wafer of the type shown in FIG. 24B may be relatively simple compared to fabrication of traditional SOI wafers in those embodiments in which layer 136 is not monocrystalline silicon.

Figure 25A:
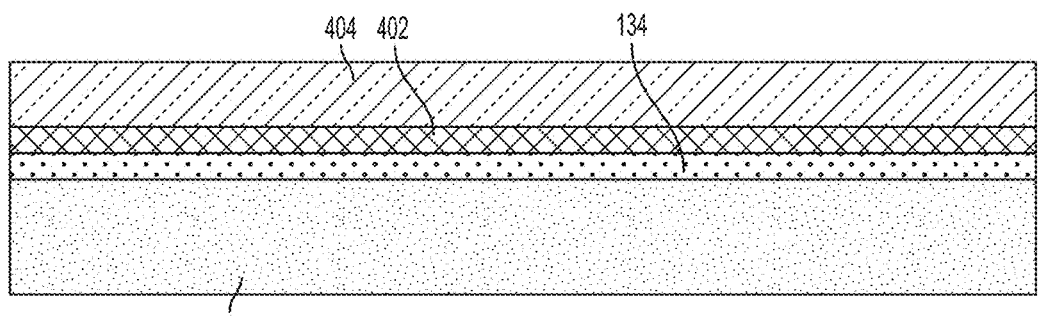
FIGS. 25A-25B illustrate an alternative process sequence for fabricating a transfer wafer having a piston formed therein, according to a non-limiting embodiment of the present application.
Figure 25B:
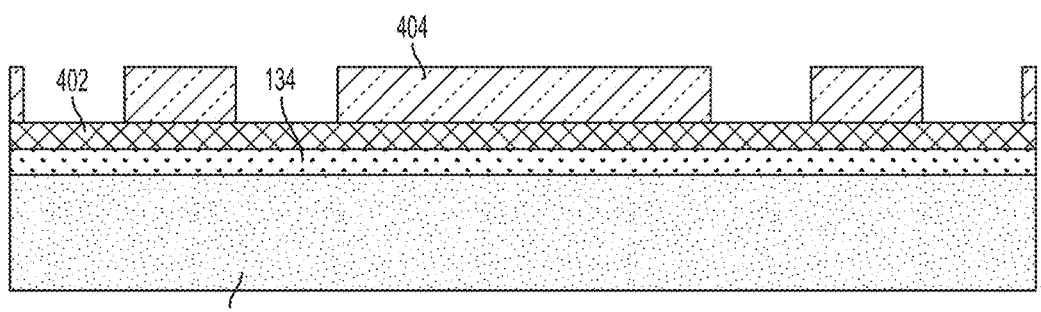

FIGS. 25A-25B illustrate an alternative process sequence for fabricating a transfer wafer having a piston formed therein, according to a non-limiting embodiment of the present application. The transfer wafer may be the type previously described in connection with FIG. 4A.

The base layer 132 may be bulk silicon. Insulating layer 134 (e.g., SiO$_2$) may be deposited on the silicon. Then layer 402 may be deposited on the insulating layer 134. In some embodiments, the layer 402 may be polysilicon or amorphous silicon, although single crystal silicon may be used in some embodiments. Next, layer 404 may be deposited to provide the structure shown in FIG. 25A.

Subsequently, as shown in FIG. 25B, the layer 404 may be patterned to provide a piston configuration. Thus, it should be appreciated that the illustrated transfer wafer may be fabricated by relatively simple deposition and etching steps, and may be relatively simple to fabricate compared to fabrication of traditional SOI wafers in those embodiments in which the layer 402 is not single crystal silicon.

The foregoing discussion has focused on single CUTs and formation of the same for purposes of simplicity. It should be appreciated, however, that the various aspects of the present application are not limited to single CUTs. Rather, the methods disclosed herein may be performed at the wafer level and thus may be used to fabricate multiple CUTs of the types described herein, i.e., aspects of the present application provide for wafer-level processing of CUTs. For example, a single substrate (e.g., a single CMOS wafer) may have tens, hundreds, thousands, tens of thousands, hundreds of thousands, or millions of CUTs formed therein.

According to an aspect of the present application, the CUTs described herein may be fabricated using a full reticle. Such capability may facilitate fabrication of large numbers of CUTs on a single chip.

Moreover, aspects of the present application may provide for larger numbers of ultrasonic transducers per a given chip area than previously attainable. As has been described, aspects of the present application provide for formation of smaller ultrasonic transducers than conventionally possible. The membranes may be made thinner than those of conventional ultrasonic transducers (e.g., than conventional CMUTs) because of the wide variety of types of materials which may be used for membranes according to aspects of the present application and because of the manners in which the membranes may be formed from the transfer wafers described herein. Because transducer behavior may depend at least in part on the relationship between the membrane thickness and the cavity size (e.g., the transducer aperture), making thinner membranes may allow for making smaller transducers than were previously possible. Accordingly, more transducers may be created on a single chip than previously possible.

When multiple CUTs are formed, they may be electrically interconnected in various manners to form a desired device. A single CUT may be referred to herein as a cell. In some embodiments, multiple CUTs may be interconnected to form an element, i.e., an element may include one or more CUT cells. Cells and/or elements may be arranged and electrically connected suitably to form, for example, an ultrasound transducer arrangement operable for ultrasound imaging and/of HIFU. Thus, for example, the cells and/or elements may be arranged and electrically connected suitably to provide desired frequency behavior (e.g., bandwidth, center frequency, etc.) for an ultrasound imaging and/or HIFU device. The grouping or connection of CUT cells into multi-cell elements may be achieved through suitable connection of the CUTs to ICs of the CMOS wafer, in some embodiments.

While various aspects and embodiments have been described as providing monolithically integrated ultrasonic transducers and CMOS wafers having ICs formed therein, not all aspects and embodiments are limited in this respect. For example, some aspects of the present application may also apply to flip-chip bonded and multi-chip configurations. For example, making electrical contact to the bottom side of a membrane may be performed in flip-chip bonded configurations. Other aspects may also apply to non-monolithic devices.

The aspects of the present application may provide one or more benefits, some of which have been previously described. Now described are some non-limiting examples of such benefits. It should be appreciated that not all aspects and embodiments necessarily provide all of the benefits now described. Further, it should be appreciated that aspects of the present application may provide additional benefits to those now described.

Aspects of the present application provide manufacturing processes suitable for formation of monolithically integrated ultrasonic transducers and CMOS structures (e.g., CMOS ICs). In at least some embodiments, the processes may be relatively inexpensive to perform, and may be scalable to large quantities of ultrasonic transducers. Aspects of the present application provide processes for manufacturing suitably sized ultrasonic transducers for operation in connection with low voltage CMOS ICs. Aspects of the present application provide robust processes for making ultrasonic transducers of various configurations. Other benefits may also be provided in accordance with one or more aspects of the present application.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present application involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Elements other than those specifically identified by the "and/or" clause may optionally be present, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasonic transducer apparatus, comprising:
   a substrate comprising an integrated circuit;
   a membrane bonded to the substrate such that a sealed cavity exists between an uppermost portion of the substrate and the membrane, thereby defining, at least in part, an ultrasonic transducer, with the sealed cavity disposed between the membrane and the substrate, the membrane comprising a first layer on a bottommost portion of the membrane, a second layer coupled to the first layer, and a buried oxide layer coupled to the second layer, the second layer comprising silicon; and
   one or more first standoff structures disposed on the uppermost portion of the substrate, wherein the one or more first standoff structures create a standoff between the substrate and the membrane and comprise a same material as the first layer on the bottommost portion of the membrane.

2. The ultrasonic transducer apparatus of claim 1, wherein the one or more first standoff structures comprise sidewalls of the sealed cavity.

3. The ultrasonic transducer apparatus of claim 1, wherein the substrate comprises a metal electrode aligned with the sealed cavity.

4. An ultrasonic transducer apparatus, comprising:
a substrate comprising an integrated circuit;
a membrane bonded to the substrate such that a sealed cavity exists between an uppermost portion of the substrate and the membrane, thereby defining, at least in part, an ultrasonic transducer, with the sealed cavity disposed between the membrane and the substrate, the membrane comprising a first layer on a bottommost portion of the membrane and a second layer coupled to the first layer, the second layer comprising silicon; and
one or more first standoff structures disposed on the uppermost portion of the substrate, wherein the one or more first standoff structures create a standoff between the substrate and the membrane and comprise a same material as the first layer on the bottommost portion of the membrane,
wherein the membrane comprises one or more second standoff structures contacting the one or more first standoff structures.

5. The ultrasonic transducer apparatus of claim 4, wherein the one or more second standoff structures are bonded to the one or more first standoff structures.

6. The ultrasonic transducer apparatus of claim 5, wherein the one or more second standoff structures are bonded to the one or more first standoff structures such that the one or more second standoff structures are aligned with the one or more first standoff structures.

7. The ultrasonic transducer apparatus of claim 4, wherein the one or more second standoff structures comprise a same material as the one or more first standoff structures.

8. The ultrasonic transducer apparatus of claim 4, wherein the substrate comprises a metal electrode aligned with the sealed cavity.

9. The ultrasonic transducer apparatus of claim 4, wherein the one or more first standoff structures comprise sidewalls of the sealed cavity.

10. A method, comprising:
forming one or more first standoff structures on an uppermost portion of a substrate comprising an integrated circuit; and
bonding the substrate with a membrane such that a sealed cavity exists between the uppermost portion of the substrate and the membrane, thereby defining, at least in part, an ultrasonic transducer, with the sealed cavity disposed between the membrane and the substrate, wherein the membrane comprises a first layer on a bottommost portion of the membrane, a second layer coupled to the first layer, and a buried oxide layer coupled to the second layer, the second layer comprising silicon,
wherein the one or more first standoff structures create a standoff between the substrate and the membrane and comprise a same material as the first layer on the bottommost portion of the membrane.

11. The method of claim 10, wherein the one or more first standoff structures comprise sidewalls of the sealed cavity.

12. The method of claim 10, wherein the substrate comprises a metal electrode aligned with the sealed cavity.

13. A method, comprising:
forming one or more first standoff structures on an uppermost portion of a substrate comprising an integrated circuit; and
bonding the substrate with a membrane such that a sealed cavity exists between the uppermost portion of the substrate and the membrane, thereby defining, at least in part, an ultrasonic transducer, with the sealed cavity disposed between the membrane and the substrate, wherein the membrane comprises a first layer on a bottommost portion of the membrane and a second layer coupled to the first layer, the second layer comprising silicon,
wherein:
the one or more first standoff structures create a standoff between the substrate and the membrane and comprise a same material as the first layer on the bottommost portion of the membrane,
the membrane comprises one or more second standoff structures, and
bonding the substrate with the membrane comprises bonding the one or more first standoff structures with the one or more second standoff structures.

14. The method of claim 13, wherein bonding the one or more first standoff structures with the one or more second standoff structures comprises aligning the one or more first standoff structures with the one or more second standoff structures.

15. The method of claim 13, wherein the one or more second standoff structures comprise a same material as the one or more first standoff structures.

16. The method of claim 13, wherein the substrate comprises a metal electrode aligned with the sealed cavity.

17. The method of claim 13, wherein the one or more first standoff structures comprise sidewalls of the sealed cavity.

* * * * *